United States Patent
Park et al.

(10) Patent No.: US 10,610,178 B2
(45) Date of Patent: *Apr. 7, 2020

(54) X-RAY IMAGING APPARATUS, METHOD OF CONTROLLING THE SAME, AND X-RAY IMAGING SYSTEM

(71) Applicant: SAMSUNG ELECTRONICS CO., LTD., Suwon-si, Gyeonggi-do (KR)

(72) Inventors: Jong Seo Park, Yongin-si (KR); Sung Nam Kim, Seoul (KR); Ji Hye Kim, Seoul (KR); Jong Hyun Shin, Seoul (KR); Eun Jae Lee, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/257,821

(22) Filed: Jan. 25, 2019

(65) Prior Publication Data

US 2019/0167217 A1    Jun. 6, 2019

Related U.S. Application Data

(63) Continuation of application No. 14/886,168, filed on Oct. 19, 2015, now Pat. No. 10,219,766.

(30) Foreign Application Priority Data

Oct. 17, 2014  (KR) .................. 10-2014-0141076
Aug. 19, 2015  (KR) .................. 10-2015-0116691

(51) Int. Cl.
*A61B 6/00*    (2006.01)

(52) U.S. Cl.
CPC ............ *A61B 6/461* (2013.01); *A61B 6/4283* (2013.01); *A61B 6/4411* (2013.01); *A61B 6/465* (2013.01)

(58) Field of Classification Search
CPC ....... A61B 6/461; A61B 6/465; A61B 6/4411; A61B 6/4283
See application file for complete search history.

(56) References Cited

U.S. PATENT DOCUMENTS

| | | | |
|---|---|---|---|
| 10,219,766 B2 * | 3/2019 | Park | A61B 6/461 |
| 2003/0142859 A1 | 7/2003 | Okuzawa | |
| 2007/0165783 A1 | 7/2007 | Tabanjeh | |
| 2008/0292062 A1 | 11/2008 | Marar | |

(Continued)

FOREIGN PATENT DOCUMENTS

| | | |
|---|---|---|
| CN | 102293657 A | 12/2011 |
| CN | 102551760 A | 7/2012 |

(Continued)

OTHER PUBLICATIONS

Communication dated Nov. 24, 2017 by the European Patent Office in counterpart European Patent Application No. 15190383.8.

(Continued)

*Primary Examiner* — Courtney D Thomas
(74) *Attorney, Agent, or Firm* — Staas & Halsey LLP

(57) ABSTRACT

An x-ray imaging apparatus and a method of controlling the x-ray imaging apparatus are provided. The x-ray imaging apparatus includes x-ray detectors, and a user interface configured to display sizes of the x-ray detectors, and display a modality in which an x-ray detector, among the x-ray detectors, is usable, while a size of the x-ray detector is displayed.

19 Claims, 71 Drawing Sheets

(56) References Cited

U.S. PATENT DOCUMENTS

| | | | |
|---|---|---|---|
| 2009/0130983 | A1 | 5/2009 | Venturino et al. |
| 2011/0013220 | A1 | 1/2011 | Sabol et al. |
| 2011/0110494 | A1 | 5/2011 | Lee |
| 2011/0274251 | A1 | 11/2011 | Omernick et al. |
| 2012/0163542 | A1 | 6/2012 | Kitano et al. |
| 2012/0195407 | A1 | 8/2012 | Nenoki et al. |
| 2012/0321043 | A1 | 12/2012 | Yonekawa |
| 2013/0094628 | A1 | 4/2013 | Lalena et al. |
| 2013/0168568 | A1 | 7/2013 | Watanabe |

FOREIGN PATENT DOCUMENTS

| | | |
|---|---|---|
| CN | 203244404 U | 10/2013 |
| EP | 2277444 | 1/2011 |
| EP | 2390682 | 11/2011 |
| JP | H 7-313497 | 12/1995 |
| JP | 2010-57707 | 3/2010 |
| JP | 2011-67335 | 4/2011 |
| JP | 5151699 | 2/2013 |
| JP | 5697731 | 4/2015 |
| KR | 1020110018042 | 2/2011 |
| WO | WO 2009/031465 A1 | 3/2009 |
| WO | WO 2011142157 A1 | 11/2011 |

OTHER PUBLICATIONS

Communication dated Feb. 22, 2018 by the Korean Patent Intellectual Property Office in counterpart Korean Patent Application No. 10-2015-0116691.

Communication dated Sep. 28, 2017, issued by the Korean Intellectual Property Office in counterpart Korean Patent Application No. 10-2015-0116691.

Communication dated Apr. 9, 2017, issued by the Korean Intellectual Property Office in corresponding Korean Application No. 10-2015-0116691.

Communication dated Dec. 2, 2016 issued by the Korean Intellectual Property Office in counterpart Korean Patent Application No. 10-2015-0116588.

Communication dated Feb. 1, 2017 issued by the Korean Intellectual Property Office in counterpart Korean Patent Application No. 10-2015-0116588.

Communication dated Mar. 17, 2016, issued by the International Searching Authority in counterpart International Patent Application No. PCT/KR2015/010889 (PCT/ISA/210).

Communication dated Mar. 17, 2016 issued by the European Patent Office in counterpart European Patent Application 15189965.5.

Communication dated Jun. 28, 2016, issued by the Korean Intellectual Property Office in counterpart Korean Patent Application No. 10-2015-0116588.

Communication dated Aug. 9, 2016 issued by the European Patent Office in counterpart European Patent Application 15189965.5.

Communication dated Mar. 17, 2016, issued by the International Searching Authority in counterpart International Application No. PCT/KR2015/010886.

Communication dated Mar. 10, 2016, issued by the European Patent Office in counterpart European Application No. 15190383.8.

Office Action dated Jan. 30, 2019 in related U.S. Appl. No. 14/886,168.

Office Action dated Oct. 24, 2018 in related U.S. Appl. No. 14/886,168.

Office Action dated Sep. 27, 2018 in related U.S. Appl. No. 14/886,168.

Office Action dated Jun. 14, 2018 in related U.S. Appl. No. 14/886,168.

Office Action dated Mar. 14, 2018 in related U.S. Appl. No. 14/886,168.

Office Action dated Nov. 27, 2017 in related U.S. Appl. No. 14/886,168.

Office Action dated Jun. 29, 2017 in related U.S. Appl. No. 14/886,168.

U.S. Appl. No. 14/886,168, filed Oct. 19, 2015, Jong Seo Park et al., Samsung Electronics Co., Ltd.

Partial European Search Report dated Aug. 12, 2019 in corresponding European Patent Application No. 19170844.5.

Chinese Office Action dated Dec. 17, 2019 issued in Chinese Patent Application No. 201910438391.8.

European Office Action dated Feb. 1, 2020 issued in European Patent Application No. 19170844.5.

\* cited by examiner

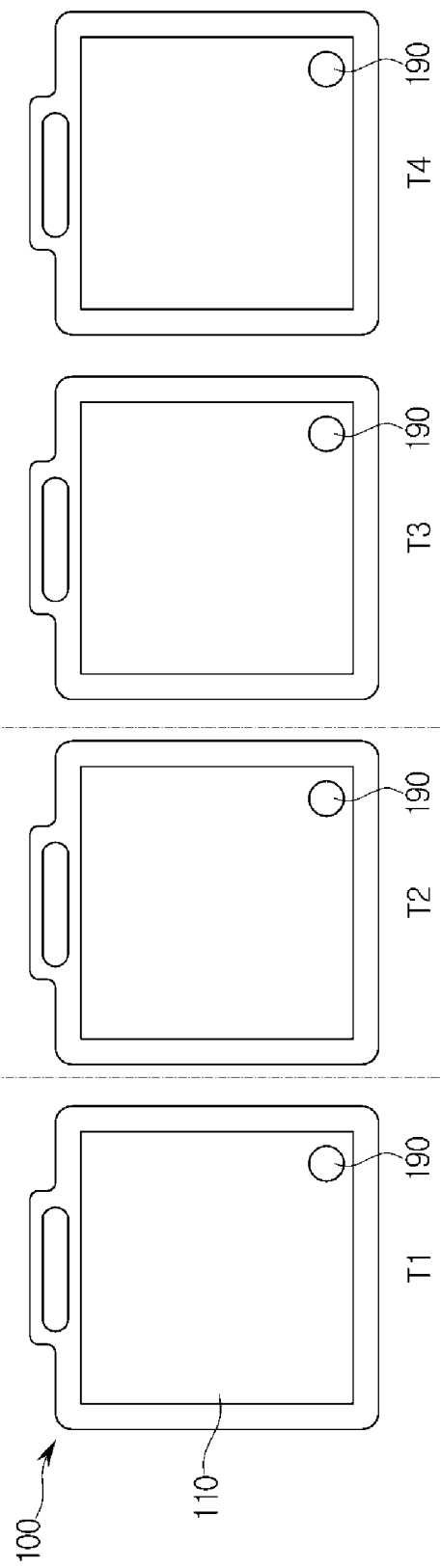

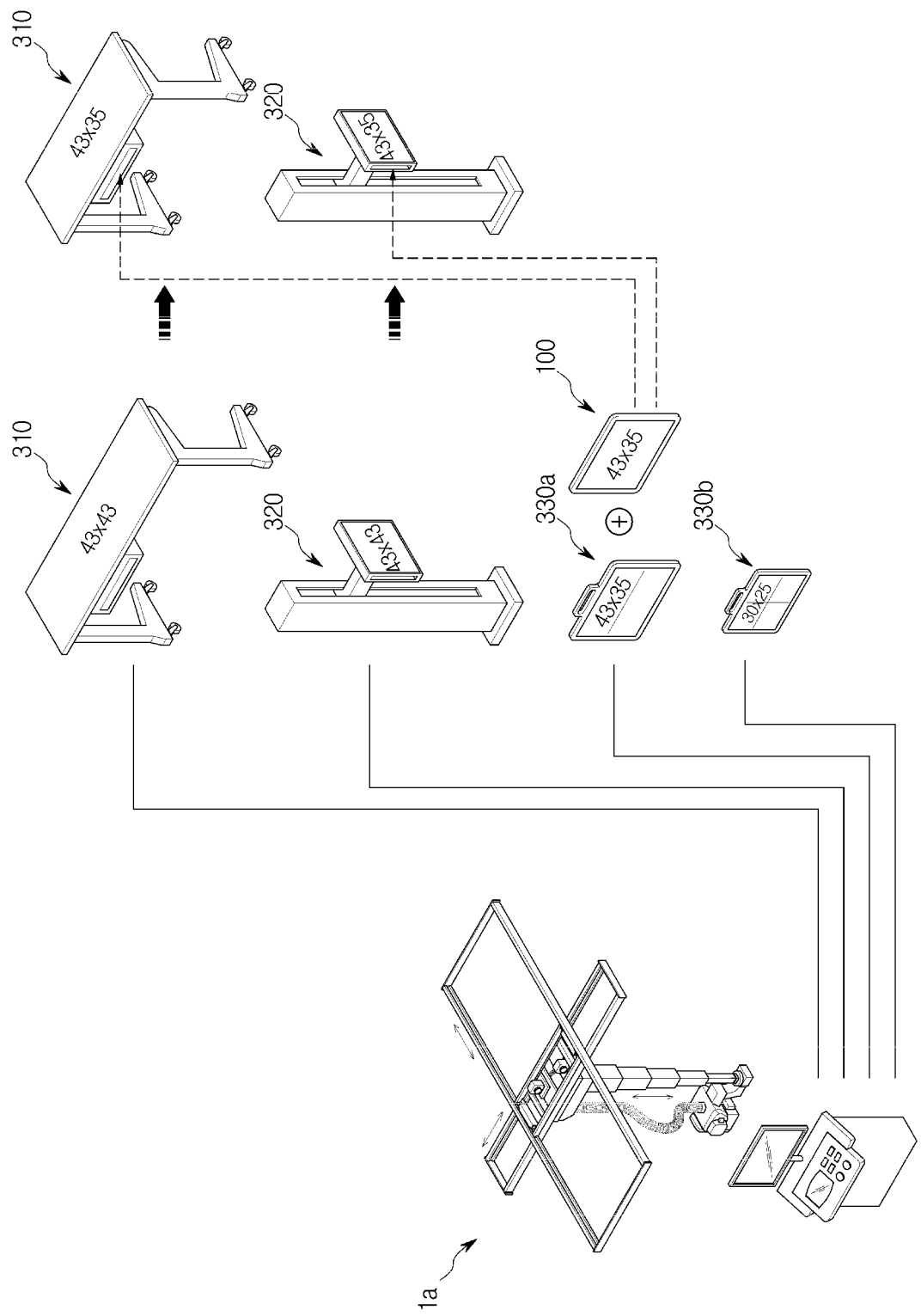

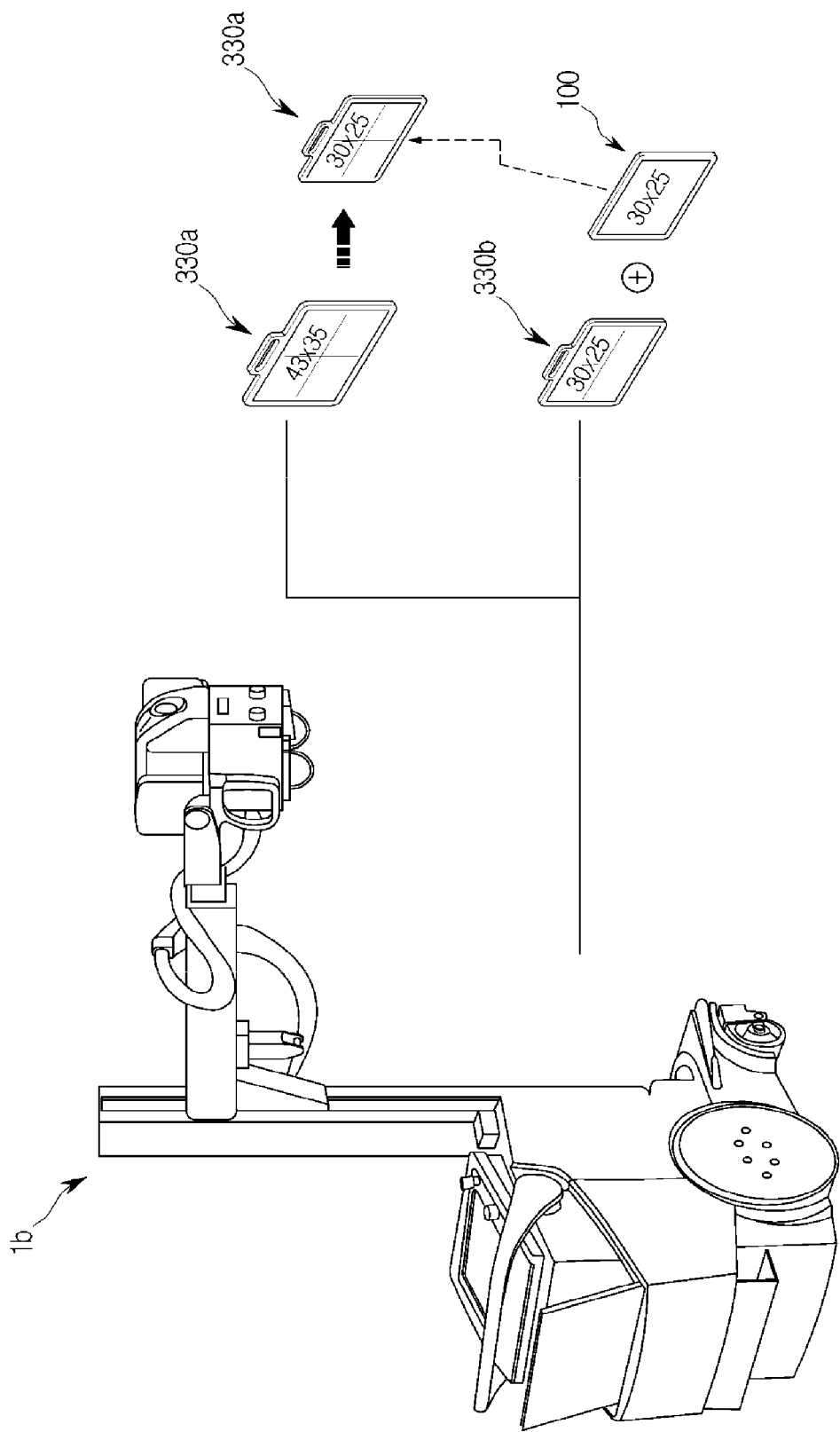

X-RAY IMAGING APPARATUS, METHOD OF CONTROLLING THE SAME, AND X-RAY IMAGING SYSTEM

CROSS-REFERENCE TO RELATED APPLICATIONS

This application is a continuation application of U.S. patent application Ser. No. 14/886,168, filed on Oct. 19, 2015, which claims priority from Korean Patent Application No. 10-2014-0141076, filed on Oct. 17, 2014, and Korean Patent Application No. 10-2015-0116691, filed on Aug. 19, 2015, in the Korean Intellectual Property Office, the disclosures of which are incorporated herein by reference in their entireties.

BACKGROUND

1. Field

Apparatuses and methods consistent with exemplary embodiments relate to an x-ray imaging apparatus, a method of controlling the same, and an x-ray imaging system.

2. Description of the Related Art

X-ray imaging apparatuses obtain an internal image of an object using x-rays. X-ray imaging apparatuses image an inside of an object using a noninvasive method of x-raying the object and detecting x-rays that penetrate the object. Accordingly, medical x-ray imaging apparatuses may be used to diagnose an injury or disease inside an object, which is not externally diagnosable.

X-ray imaging apparatuses each include an x-ray source that generates and emits x-rays to an object and an x-ray detector that detects x-rays that pass through the object. To image various parts of the object, the x-ray source is provided to be movable, and the x-ray detector may be mounted on an imaging table or an imaging stand or provided to be portable.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an x-ray imaging apparatus capable of setting communication of a detector and a mounting portion on which the detector is to be mounted using detector pairing data previously stored in a workstation or a server, a method of controlling the x-ray imaging apparatus, and an x-ray imaging system.

One or more exemplary embodiments provide an x-ray imaging apparatus for selecting a plurality of x-ray detectors depending on a size thereof and a mounting portion on which the selected x-ray detector is to be mounted, a method of controlling the x-ray imaging apparatus, and an x-ray imaging system.

According to an aspect of an exemplary embodiment, an x-ray imaging apparatus includes x-ray detectors, and a user interface configured to display sizes of the x-ray detectors, and display a modality in which an x-ray detector, among the x-ray detectors, is usable, while a size of the x-ray detector is displayed.

The apparatus may further include a mounting portion on which the x-ray detector is mountable, and the displayed modality may include the mounting portion.

The user interface may be further configured to, while the size of the x-ray detector is displayed, receive a selection of the x-ray detector, and receive a selection of the displayed mounting portion on which the x-ray detector is to be mounted.

A size of an area of the mounting portion in which the x-ray detector is mountable, may be adjusted, and in response to the size of the area of the mounting portion being adjusted, the user interface may be further configured to display the mounting portion based on the size of the x-ray detector, while the size of the x-ray detector is displayed.

The size of the x-ray detector may be displayed using at least one among a size of a text and a size of an icon.

The user interface may be further configured to display the sizes of the x-ray detectors one at a time.

The user interface may be further configured to display the sizes of the x-ray detectors at a same time.

The user interface may be further configured to display whether the x-ray detector is swapped, while the size of the x-ray detector is displayed.

The user interface may be further configured to display at least one among a color, a shape, resolution, a response time, and a diagnosis room of the x-ray detector, while the size of the x-ray detector is displayed.

The user interface may be further configured to display a mounting portion on which the x-ray detector is mounted, while the size of the x-ray detector is displayed.

The user interface may be further configured to receive a selection of the displayed modality in which the x-ray detector is to be used, while the size of the x-ray detector is displayed.

The user interface may be further configured to receive a condition to search for the x-ray detector, the condition including at least one among a size, a color, a shape, resolution, a response time, and a diagnosis room of the x-ray detector, and receive an input to search for the x-ray detector based on the received condition.

In response to there being no x-ray detector corresponding to the received condition among the x-ray detectors, the user interface may be further configured to display another x-ray detector corresponding to a condition similar to the received condition, among the x-ray detectors.

In response to there being no x-ray detector corresponding to the received condition including the diagnosis room, among the x-ray detectors, the user interface may be further configured to receive and display information of another diagnosis room in which another x-ray detector corresponding to another condition from a server is positioned.

The apparatus may further include at least one x-ray detector.

The x-ray detectors may include the at least one x-ray detector and at least one external x-ray detector.

The user interface may be further configured to receive a registration of the at least one external x-ray detector.

According to an aspect of another exemplary embodiment, an x-ray imaging apparatus includes x-ray detectors, and a user interface configured to display colors of the x-ray detectors, and display a mounting portion in which an x-ray detector, among the x-ray detectors, is mountable, while a color of the x-ray detector is displayed.

According to an aspect of another exemplary embodiment, an x-ray imaging apparatus includes x-ray detectors, and a user interface configured to display at least one among shapes, resolutions, and response times of the x-ray detectors, and display a modality in which an x-ray detector, among the x-ray detectors, is usable, while at least one among a shape, a resolution, and a response time of the x-ray detector is displayed.

According to an aspect of another exemplary embodiment, a method of controlling an x-ray imaging apparatus, includes displaying sizes of x-ray detectors, and displaying a modality in which an x-ray detector, among the x-ray detectors, is usable, while a size of the x-ray detector is displayed.

The displayed modality may include a mounting portion on which the x-ray detector is mountable.

The method may further include, while the size of the x-ray detector is displayed, receiving a selection of the x-ray detector, and receiving a selection of the displayed mounting portion on which the x-ray detector is to be mounted.

A size of an area of the mounting portion in which the x-ray detector is mountable, may be adjusted, and in response to the size of the area of the mounting portion being adjusted, the method may further include displaying the mounting portion based on the size of the x-ray detector, while the size of the x-ray detector is displayed.

The displaying the sizes of the x-ray detectors may include displaying the sizes of the x-ray detectors one at a time.

The displaying the sizes of the x-ray detectors may include displaying the sizes of the x-ray detectors at a same time.

The method may further include, while the size of the x-ray detector is displayed, displaying a mounting portion on which the x-ray detector is mounted.

The method may further include receiving a selection of the displayed modality in which the x-ray detector is to be used, while the size of the x-ray detector is displayed.

The method may further include receiving a condition to search for the x-ray detector, the condition including at least one among a size, a color, a shape, resolution, a response time, and a diagnosis room of the x-ray detector, and receiving an input to search for the x-ray detector based on the received condition.

The method may further include, in response to there being no x-ray detector corresponding to the received condition among the x-ray detectors, displaying another x-ray detector corresponding to a condition similar to the received condition, among the x-ray detectors.

The method may further include, in response to there being no x-ray detector corresponding to the received condition including the diagnosis room, among the x-ray detectors, receiving and displaying information of another diagnosis room in which another x-ray detector corresponding to another condition from a server is positioned.

A non-transitory computer-readable storage medium may store a program including instructions to cause a computer to perform the method.

According to an aspect of another exemplary embodiment, an apparatus includes a display, and a controller configured to control the display to display a size of a x-ray detector, and control the display to display a location at which the x-ray detector is mountable, in response to the display displaying the size of the x-ray detector.

BRIEF DESCRIPTION OF THE DRAWINGS

The above and/or other aspects will be more apparent by describing exemplary embodiments, with reference to the accompanying drawings, in which:

FIG. 6 is a front view of the detector including a detector display according to an exemplary embodiment;

FIG. 7B is a conceptual view illustrating an x-ray detector compatible through changing a size of a mounting portion in the ceiling type x-ray imaging apparatus according to an exemplary embodiment;

FIG. 8B is a conceptual view illustrating that an x-ray detector is compatible through changing a size of a mounting portion in the mobile type x-ray imaging apparatus according to an exemplary embodiment;

DETAILED DESCRIPTION

Figure 1:
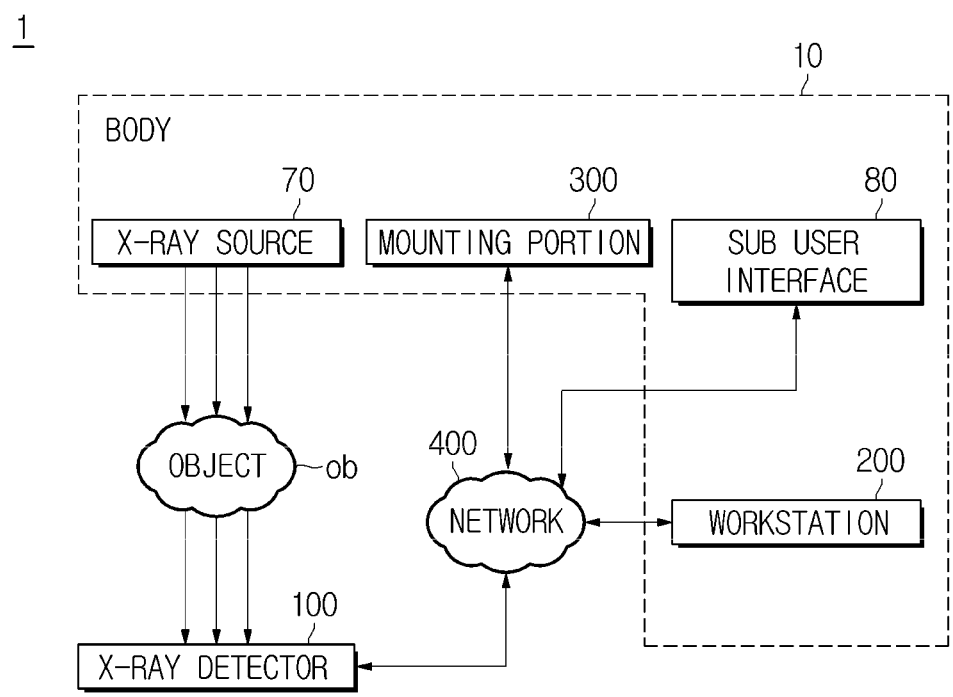
FIG. 1 is a schematic block diagram illustrating an x-ray imaging apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

It will be understood that the terms "comprises" and/or "comprising" used herein specify the presence of stated features or components, but do not preclude the presence or addition of one or more other features or components. In addition, the terms such as "unit", "-er (-or)", and "module" described in the specification refer to an element for performing at least one function or operation, and may be implemented in hardware, software, or the combination of hardware and software.

Throughout the specification, an x-ray imaging apparatus described below includes one x-ray source provided per x-ray imaging apparatus to set one x-ray detector but is not limited thereto. It is possible to set x-ray detectors as the number of x-ray sources included in one x-ray imaging apparatus.

Hereinafter, the x-ray imaging apparatus and a method of controlling the same according to exemplary embodiments will be described with reference to the attached drawings.

Figure 2:
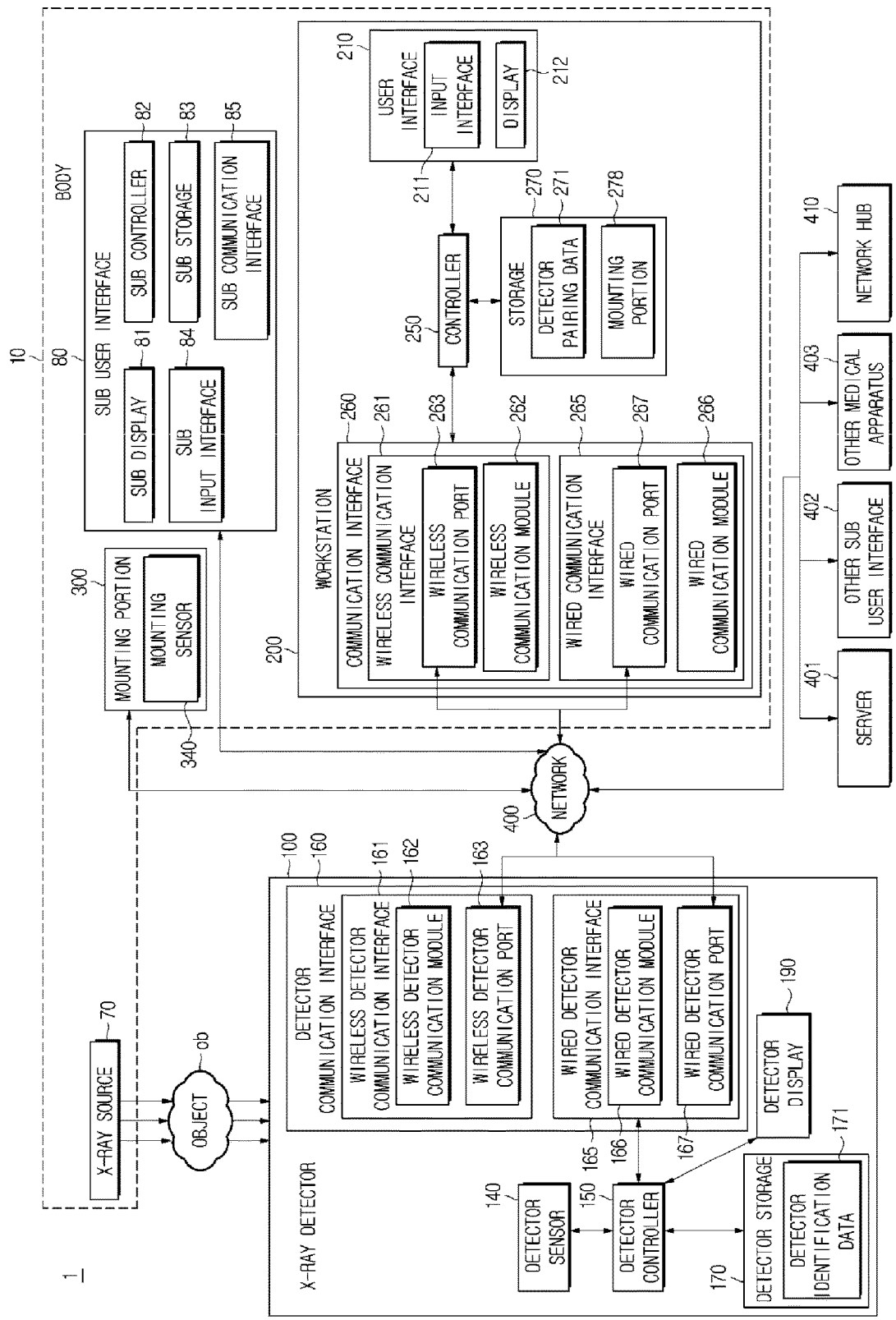
FIG. 2 is a detailed block diagram illustrating the x-ray imaging apparatus according to an exemplary embodiment.
Figure 3:
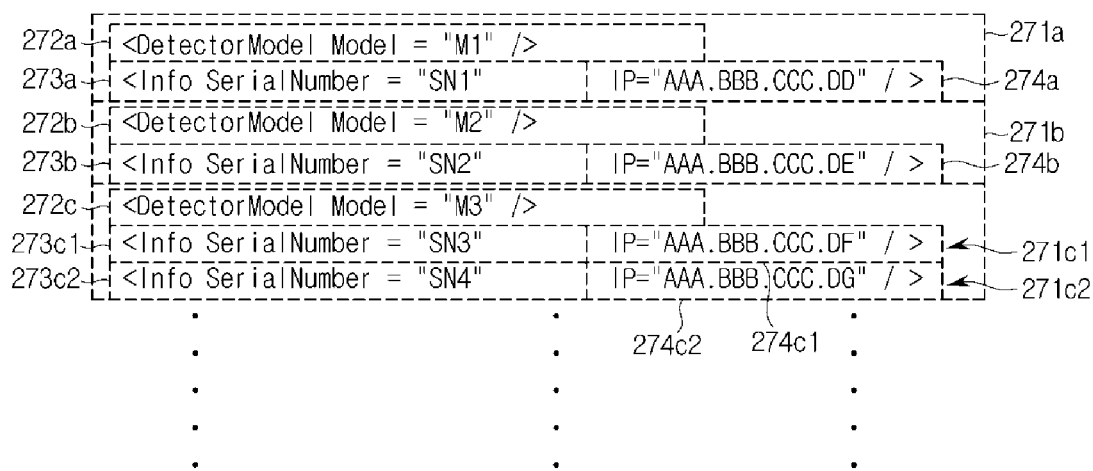
FIG. 3 is a view illustrating detector pairing data according to an exemplary embodiment.
Figure 4:
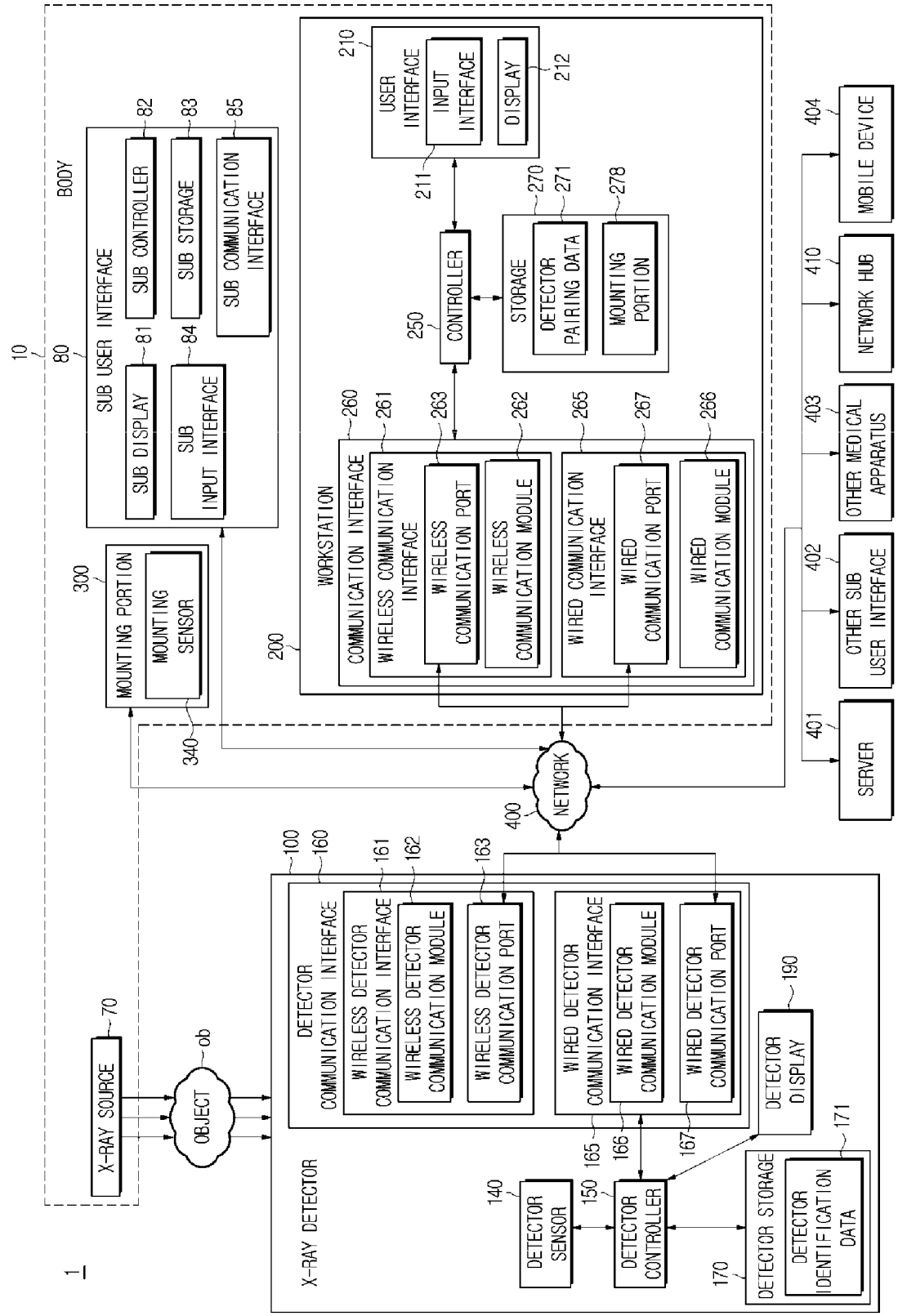
FIG. 4 is another block diagram illustrating the x-ray imaging apparatus according to an exemplary embodiment.

FIGS. 1, 2, and 4 are block diagrams of an x-ray imaging apparatus 1. FIG. 3 is a view illustrating an example of detector pairing data 271 stored in a workstation 200.

The x-ray imaging apparatus 1 includes an x-ray detector 100 and a body 10. Also, the body 10 includes an x-ray source 70, the workstation 200, a mounting portion 300, and a sub user interface 80.

The x-ray detector 100 is a device which detects x-rays which are emitted from the x-ray source 70 and pass through an object ob. The detection of x-rays is performed at a sensing panel inside the x-ray detector 100. The sensing panel may include a plurality of pixels which respond x-rays and may be arranged in a matrix shape. Also, the sensing panel converts detected x-rays into electric signals to allow an internal x-ray image of the object.

The sensing panel may be classified according to a method of forming materials, a method of converting detected x-rays into electric signals and a method of obtaining the electric signals.

First, the sensing panel is divided into a case of being formed in a single device and a case of being formed in a combined device depending on the method of forming materials.

In the case of being formed in the single device, a portion which detects x-rays and generates electric signals and a portion which reads and processes the electric signals are formed of semiconductors having a single material or manufactured through a single process. For example, a charge coupled device (CCD) or a complementary metal oxide semiconductor (CMOS) which is a light receiving element is used singly.

In the case of being formed in the combined device, a portion which detects x-rays and generates electric signals and a portion which reads and processes the electric signals are formed of different materials, respectively, or manufactured through different processes. For example, there are a case in which x-rays are detected using a light receiving element such as a photo diode, CCD, cadmium zinc telluride (CdZnTe) and electrical signals are read and processed using a CMOS read out integrated circuit (ROIC), a case in which x-rays are detected using a strip detector and electric signals are read and processed using a CMOS ROIC, and a case in which amorphous silicon (a-Si) or amorphous selenium (a-Se) flat panel system is used.

Also, the sensing panel is divided into a direct conversion type and an indirect conversion type depending on the method of converting x-rays into electric signals.

In the direct conversion type, when x-rays are emitted, electron-hole pairs are instantaneously formed inside a light receiving element and electrons move to an anode and holes move to a cathode due to an electric field applied to both ends of the light receiving element in such a way that the sensing panel converts such movement into electric signals. As a material used for the light receiving element in the direct conversion type, there are a-Se, CdZnTe, HgI2, PbI2, etc.

In the indirect conversion type, x-rays emitted from the x-ray source 70 react with a scintillator and emit photons having a wavelength in a visible ray area and then the light receiving element senses and converts the photons into electric signals. As a material used for the light receiving element in the indirect conversion type, there is a-Si. As the scintillator, a thin plate type gadolinium oxysulfide (GADOX) scintillator, a micropillar type or needle type CSI(T1), etc. are used.

Also, the sensing panel is divided, according to the method of obtaining an electric signal, into a charge integration mode of storing charges for a time and obtaining a signal therefrom and a photon counting mode of counting whenever a signal is generated by a single x-ray photon.

Even though any one of the methods described above may be applied to the sensing panel, hereinafter, for convenience of description, it will be described that the direct conversion type of directly obtaining electrical signals from x-rays, a hybrid type of coupling a sensor chip which detects x-rays with a readout circuit chip, and the photon counting mode are applied.

Also, the x-ray detector 100 includes a detector sensor 140, a detector storage 170, a detector communication interface 160, a detector display 190, and a detector controller 150.

The detector sensor 140 may sense a position of the x-ray detector 100 when the x-ray detector 100 is used while not being mounted on the mounting portion 300. The detector sensor 140 may be provided on a rear surface or a side surface of the x-ray detector 100 or may be provided inside the x-ray detector 100. That is, without having an effect on x-ray detection of the x-ray detector 100, there is no limitation in the position of the detector sensor 140.

The detector storage 170 stores detector identification data 171 for specifying a type of the corresponding x-ray detector 100.

Here, the detector identification data 171 is information for identifying one of a plurality of such x-ray detectors 100. In detail, the detector identification data 171 may include a detector model, a serial number, and a detector IP. The detector model may be a model name of a detector of a manufacturer. The serial number is information for identifying a plurality of detectors which are the same detector model and may be a manufacturing date or a serial number of a corresponding detector. The detector IP is information for identifying the plurality of detectors having the same detector model and serial number and may be a protocol set to communicate with the workstation 200.

The detector storage 170 may include a non-volatile memory such as a read-only memory (ROM), high-speed random access memory (RAM), a magnetic disk storage device, and a flash memory or another non-volatile semiconductor memory device.

For example, as the detector storage 170 that is a semiconductor memory device, there are a secure digital (SD) memory card, a secure digital high capacity (SDHC) memory card, a mini SD memory card, a mini SDHC memory card, a Trans-Flash (TF) memory card, a micro SD memory card, a micro SDHC memory card, a memory stick, a CompactFlash (CF) card, a multi-media card (MMC), an MMC micro, an extreme digital (XD) card, etc.

Also, the detector storage 170 may include a network-attached storage device which accesses through a network 400.

The detector communication interface 160 transmits and receives information for identifying and setting the corresponding x-ray detector 100. In detail, the detector communication interface 160 may transmit the detector identification data 171 stored in the detector storage 170 to the workstation 200 and may receive information on setting the corresponding x-ray detector 100 by the workstation 200. Also, the detector communication interface 160 may transmit electric signals converted from x-rays received by the x-ray detector 100 to the workstation 200. Also, the detector communication interface 160 may transmit a protocol set to communicate with the network 400 to the workstation 200 to recognize a diagnosis room in which the corresponding x-ray detector 100 is located. Also, the detector communication interface 160 may be connected to the network 400 wirelessly or over wires and may communicate with an external server 401, another sub user interface 402, another medical apparatus 403, or a network hub 410. Also, the detector communication interface 160 may data-communicate according to communication standards.

The detector communication interface 160 may transmit and receive data related to remote control through the network 400 and may transmit and receive an operation of the other medical apparatus 403. Further, the detector communication interface 160 may receive error correction information of the detector model from the server 401 to utilize for an operation of the x-ray imaging apparatus 1.

The detector communication interface 160 may be wired or wirelessly connected to the network 400 and may communicate with the server 401, the other sub user interface 402, the other medical apparatus 403, or the network hub 410. The detector communication interface 160 may include one or more components which communicate with the network 400. For example, the detector communication interface 160 includes a wireless detector communication interface 161 and a wired detector communication interface 165.

The wireless detector communication interface 161 is wirelessly connected to the network 400 and may transmit and receive information which is to be transferred to the workstation 200 from the x-ray detector 100 and information for setting the x-ray detector 100. The wireless detector communication interface 161 includes a wireless detector communication port 163 and a wireless detector communication module 162.

The wireless detector communication port 163 provides a path on which data to be transferred from the wireless detector communication module 162 to a wireless communication module 262 passes through a wireless communication port 263 and is transferred to the wireless communication module 262.

The wireless detector communication module 162 may pair with the wireless communication module 262 to transmit and receive information for identifying and setting the x-ray detector 100. The wireless detector communication module 162 includes an antenna system, a radio frequency (RF) transceiver, one or more amplifiers, a tuner, one or more oscillators, a digital signal processor, a codec chip set, a subscriber identity module (SIM) card, a memory 900, etc. but may include a well-known circuit which is not limited thereto to perform these functions.

Wireless communication may include global system for mobile communication (GSM), enhanced data GSM environment (EDGE), wideband code division multiple access (WCDMA), code division multiple access (CDMA), time division multiple access (TDMA), Bluetooth, Bluetooth low energy (BLE), near field communication (NFC), Zigbee, wireless fidelity (Wi-Fi, for example, IEEE802.11a, IEEE802.11b, IEEE802.11g and/or IEEE802.11n), voice over Internet protocol (VoIP), Wi-Max, Wi-Fi Direct (WFD), ultra wideband (UWB), infrared data association (IrDA), protocols for e-mail, instant messaging and/or short message service (SMS) or other appropriate communication protocols. In addition, various wireless communication methods may be used as an example of wireless communication.

The wired detector communication interface 165 is connected to the network 400 over wires and may transmit and receive information which is to be transferred to the workstation 200 from the x-ray detector 100 and information for setting the x-ray detector 100. The wired detector communication interface 165 includes a wired detector communication port 167 and a wired detector communication module 166.

The wired detector communication port 167 is connected to a wired communication port 267 through a communication cable and may transmit and receive information for identifying and setting the x-ray detector 100.

The wired detector communication port 167 may be connected with various types of communication cables. In detail, the wired detector communication port 167 may include a high-definition multimedia interface (HDMI) port, a digital video interface (DVI) port, a D-subminiature (D-sub) port, an unshielded twisted pair (UTP) cable port, and a universal serial bus (USB) port. Additionally, various communication ports for transmitting the detector identification data 171 and receiving information for setting the x-ray detector 100 may be used as an example of the wired detector communication port 167.

The wired detector communication module 166 may exchange information with a wired communication module 266 connected therewith through a communication cable. In detail, the wired detector communication module 166 may transmit a connection signal to the wired communication module 266 and may receive a response signal of the workstation 200, thereby setting both. Also, the wired detector communication module 166 may transmit the detector identification data 171 to the workstation 200 and may receive setting information of the corresponding x-ray detector 100 of the workstation 200.

Also, the wired detector communication module 166 refers to a module for communication using electric signals or optical signals. A wired communication technology may include pair cables, coaxial cables, optical fiber cables, and Ethernet cables but is not limited thereto.

When the corresponding x-ray detector 100 is selected at a graphic user interface G1 to set the corresponding x-ray detector 100 among the plurality of x-ray detectors 100 in the workstation 200, the detector display 190 may distinguish the corresponding x-ray detector 100 from the other x-ray detectors 100. That is, only the detector display 190 of the corresponding x-ray detector 100 may be turned on and the detector displays 190 of the other x-ray detectors 100 may be turned off. On the contrary, only the detector display 190 of the corresponding x-ray detector 100 may be turned off and the detector displays 190 of the other x-ray detectors 100 may be turned on.

Also, the detector display 190 may display the setting information of the x-ray detector 100. That is, the detector display 190 may display a type of the mounting portion 300 on which the corresponding x-ray detector 100 set through the workstation 200 is mounted and a communication type. Also, the detector display 190 may display x-ray images taken by the x-ray detector 100.

The detector controller 150 controls the overall operation of the x-ray detector 100. In detail, the detector controller 150 may receive and transmit the detector identification data 171 from the detector storage 170 to the workstation 200, may receive the setting information from the workstation 200 to set imaging conditions of the x-ray detector 100, and may set information in accordance with properties of the mounting portion 300 on which the corresponding x-ray detector 100 is mounted. Also, the detector controller 150 may control to transfer position information of the corresponding x-ray detector 100 sensed by the detector sensor 140 to the workstation 200 and to transfer a protocol of the corresponding x-ray detector 100 to the workstation 200. Also, the detector controller 150 may generate image signals by converting the image-taken x-rays into electric signals.

Also, the detector controller 150 performs a function of a central processing unit. The central processing unit may be a microprocessor. The microprocessor is a processing unit in which an arithmetic and logic unit, a register, a program counter, a command decoder, a control circuit, etc. are provided on at least one silicon chip.

Also, the microprocessor may include a graphic processing unit (GPU) for processing an image or video to be graphics. The microprocessor may be provided as a system-on-chip (SoC) which includes a core and the GPU. The microprocessor may include a single core, dual cores, triple cores, quad cores, and multiple cores.

Also, the detector controller 150 may include a graphic processing board which includes a GPU, a RAM, or ROM on a separate circuit board electrically connected to the microprocessor.

The body 10 may generate and emit x-rays to an object and may convert electrical signals converted at the x-ray detector 100 into image signals. Also, the body 10 may include the x-ray source 70, the workstation 200, the mounting portion 300, and the sub user interface 80.

The x-ray source 70 is a device which generates and emits x-rays to the object and may include an x-ray tube to generate x-rays. The x-ray tube may be provided as a diode which includes an anode and a cathode and a shell thereof may be a glass tube formed of silicic acid hard glass.

The workstation 200 may be connected to the plurality of x-ray detectors 100 to control the x-ray detectors 100 and may receive and display taken image signals. Also, the workstation 200 includes a storage 270, a communication interface 260, a user interface 210, and a controller 250.

The storage 270 stores and transmits the detector pairing data 271 and mounting portion data 278 to the controller 250. Also, a type and a storage method of the storage 270 may be identical to or differ from those of the detector storage 170 described above.

Here, the detector pairing data 271 is a group of information on the x-ray detectors 100 usable for the x-ray imaging apparatus 1. In detail, the detector pairing data 271 may include information corresponding to the detector identification data 171 stored in the plurality of x-ray detectors 100 to identify the x-ray detector 100 and may include information for setting the corresponding x-ray detector 100 in addition to the information for identifying the plurality of x-ray detectors 100. Also, the detector pairing data 271 may include feature information on a x-ray detector such as information on a size and imaging conditions of the x-ray detector 100.

Figure 15:
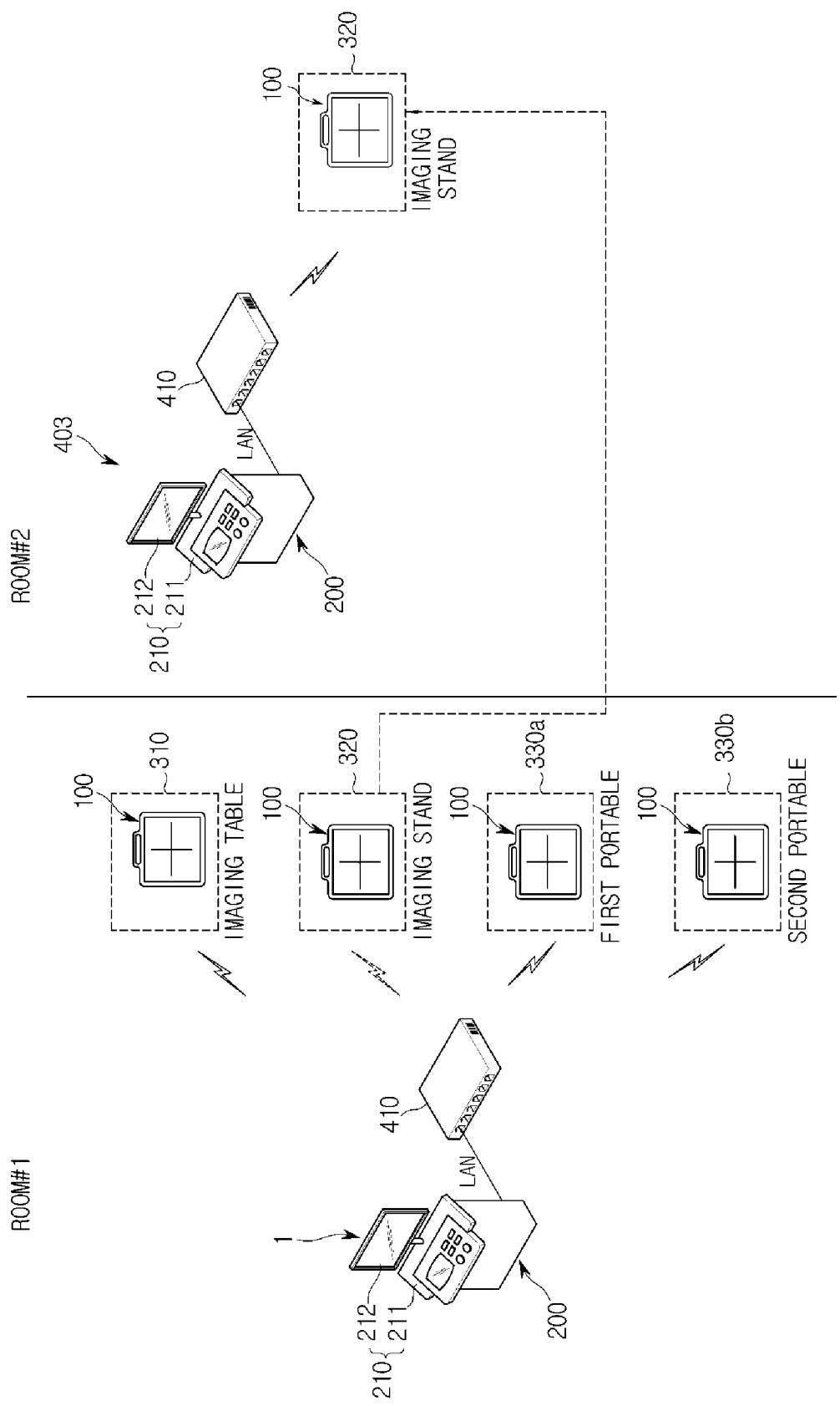
FIG. 15 is a conceptual view illustrating that a detector located in one diagnosis room is moved to another diagnosis room to connect the detector to a workstation according to an exemplary embodiment.

Also, the detector pairing data 271 may be stored in the storage 270. As shown in FIG. 15, the detector pairing data 271 may include detector models, serial numbers, and detector IPs of the plurality of x-ray detectors 100.

Referring to FIG. 3, detector models 272 may be a model name of a detector of a manufacturer. Serial numbers 273 are information for identifying a plurality of detectors which are the same detector model and may be a manufacturing date or a serial number of a corresponding detector. Detector IPs 274 are information for identifying the plurality of detectors having the same detector model and serial number and may be a protocol set to communicate with the workstation 200.

For example, the detector pairing data 271 may include first detector pairing data 271a, second detector pairing data 271b, third detector pairing data 271c1, and fourth detector pairing data 271c2.

The first detector pairing data 271a is information on the x-ray detector 100 corresponding to the first detector pairing data 271a, in which a first detector model 272a is stored as M1, a first serial number 273a is stored as SN1, and a first detector IP 274a is stored as AAA.BBB.CCC.DD. Also, the second detector pairing data 271b is information on the x-ray detector 100 corresponding to the second detector pairing data 271*b*, in which a second detector model 272*b* is stored as M2, a second serial number 273*b* is stored as SN2, and a second detector IP 274*b* is stored as AAA.BBB.C-CC.DE. Also, the third detector pairing data 271*c*1 is information on the x-ray detector 100 corresponding to the third detector pairing data 271*c*1, in which a third detector model 272*c* is stored as M3, a third serial number 273*c*1 is stored as SN3, and a third detector IP 274*c*1 is stored as AAA.BBB.CCC.DF. Also, the fourth detector pairing data 271*c*2 is information on the x-ray detector 100 corresponding to the fourth detector pairing data 271*c*2, in which the third detector model 272*c* is stored as M3, a fourth serial number 273*c*2 is stored as SN4, and a fourth detector IP 274*c*2 is stored as AAA.BBB.CCC.DG.

Here, when the third detector models 272*c* is used for the third detector pairing data 271*c*1 and the fourth detector pairing data 271*c*2, the x-ray detector 100 corresponding to the third detector pairing data 271*c*1 and the x-ray detector 100 corresponding to the fourth detector pairing data 271*c*2 may be detectors of the same type. However, the x-ray detector 100 corresponding to the third detector pairing data 271*c*1 and the x-ray detector 100 corresponding to the fourth detector pairing data 271*c*2 differ from each other in the detector IPs 274*c*1 and 274*c*2 to communicate with the workstation 200 and may be identified through the same.

Referring again to FIGS. 2 and 4, various types of such detector pairing data 271 usable for the x-ray imaging apparatus 1 may be stored in the storage 270 or the server 401.

Also, the detector pairing data 271 may include feature information. The feature information may be information on features of the x-ray detector 100 matching with the detector identification data. In detail, the feature information may include information on imaging conditions such as color calibration of the x-ray detector 100 arranged for each detector identification information) of the x-ray detector 100 connectable to an x-ray imaging system and a size, a color, a shape, resolution, and a response time of the x-ray detector 100.

The mounting portion data 278 may include imaging conditions different for each mounting portion 300 and correction values for control the imaging conditions among the x-ray detectors 100. In detail, because a table mounting portion 310, a stand mounting portion 320, and a portable mounting portion 330 have different imaging portions and imaging conditions, images taken based on the same setting value may differ. Accordingly, the workstation 200 may set the corresponding x-ray detector 100 by using the mounting portion data 278 corresponding to the mounting portion 300 selected when setting the corresponding x-ray detector 100.

The communication interface 260 receives the detector identification data 171 from the x-ray detector 100 and transmits the setting information of the x-ray detector 100 and a control signal for the x-ray detector 100 to the x-ray detector 100. Also, the communication interface 260 may obtain information on detectors not stored in the workstation 200 by updating the detector pairing data 271 through the server 401. Here, the server 401 is a system which transmits and receives information related to medical apparatuses. For example, the server 401 may be a medical picture archiving communication system (PACS). Also, the server 401 may store the detector pairing data 271 which includes identification information and setting information of the x-ray detector 100 connectable to the body 10.

Also, the communication interface 260 may set and control the x-ray detector 100 located in another diagnosis room in which the workstation 200 is not located through communication with the network hub 410 or the other medical apparatus 403.

Referring to FIG. 2 again, the communication interface 260 includes a wireless communication interface 261 and a wired communication interface 265. Also, the wireless communication interface 261 includes the wireless communication port 263 and the wireless communication module 262 and the wired communication interface 265 includes the wired communication port 267 and the wired communication module 266. Here, communication modes and types of the wireless communication port 263, the wireless communication module 262, the wired communication port 267, and the wired communication module 266 may be identical to or differ from those of the wireless detector communication port 163, the wireless detector communication module 162, the wired detector communication port 167, and the wired detector communication module 166.

The user interface 210 may display taken x-ray images and a graphic user interface for setting the x-ray detector 100 and may allow a control command for taking x-ray images and a command for setting the x-ray detector 100 to be input. Hereinafter, the graphic user interface which is displayed on the user interface 210 and receives a selection of a user will be described in detail with reference to FIGS. 16 to 64.

The controller 250 controls overall operations of the workstation 200. In detail, the controller 250 may search for information corresponding to the detector identification data 171 among the detector pairing data 271 by comparing a plurality of pieces of such received detector identification data 171 with the detector pairing data 271. Also, the controller 250 may control to search for, arrange, and display the x-ray detectors 100 connectable with the workstation 200 on the graphic user interface. Also, the controller 250 may control to select one of the connectable x-ray detectors 100, to store setting information thereof, and to transfer the stored setting information to the x-ray detector 100. Also, the controller 250 may control a setting value of the mounting portion 300 to be used to the x-ray detector 100 selected based on the mounting portion data 278. Also, the controller 250 may control the user interface 210 to provide a graphic user interface for selecting the x-ray detector 100 to be set, selecting the mounting portion 300 on which the corresponding x-ray detector 100 is to be mounted, and setting the x-ray detector 100 and the mounting portion 300. Also, the controller 250 may control the detector display 190 to distinguish the x-ray detector 100 selected to be set from other x-ray detectors 100. In addition, the controller 250 may perform various control operations for controlling the x-ray imaging apparatus 1.

Also, a configuration of the controller 250 may be identical to or differ from that of the detector controller 150 described above.

The mounting portion 300 fixes the x-ray detector 100 to allow the x-ray detector 100 to be located and to take x-ray images. Also, the mounting portion 300 includes a mounting sensor 340 to sense and transmit on which mounting portion 300 the x-ray detector 100 is mounted to the workstation 200. Also, the mounting portion 300 will be described in detail with reference to FIGS. 5 to 8.

The sub user interface 80 may be provided on one side of an x-ray source and may input various pieces of information or may operate respective apparatuses while taking x-ray images of an object ob. Also, the sub user interface 80 may include a mobile user interface.

The sub user interface 80 includes a sub display 81, a sub controller 82, a sub storage 83, a sub input interface 84, and a sub communication interface 85. The sub display 81, the sub controller 82, the sub storage 83, the sub input interface 84, and the sub communication interface 85 may perform the same operations of a display 212, the controller 250, the storage 270, an input interface 211, and the communication interface 260 of the workstation 200 described above. For example, the sub user interface 80 may receive identification information from the x-ray detector 100, may search for data matching with the identification information among detector pairing data, and may display a feature of the x-ray detector 100 based on the searched data. Also, the sub user interface 80 may perform the described operation performed by the workstation 200 which communicates with the x-ray detector 100. The names of the sub display 81, the sub controller 82, the sub storage 83, the sub input interface 84, and the sub communication interface 85 are to distinguish from the components of the workstation 200. When it is unnecessary to distinguish from the workstation 200, it is possible to designate them as the display 81, the controller 82, the storage 83, the input interface 84, and the communication interface 85.

Otherwise, operations such as storing detector pairing data and searching for information corresponding to detector identification data among the detector pairing data, that is, operations which have been described as being performed by the controller 250 may be performed by the workstation 200 and operations such as displaying information on the x-ray detector 100 connectable with the workstation 200 or a feature of the x-ray detector 100 and receiving a command from the user, that is, operations which have been described as being performed by the user interface 210 may be performed by the sub display 81 and the sub input interface 84 of the sub user interface 80.

Also, as shown in FIG. 4, a mobile device 404 able to communicate such as a smart phone, tablet personal computer (PC), and a personal digital assistant (PDA) may perform some of the operations of the workstation 200 described above. For example, the operation which have been described as being performed by the controller 250 may be performed by the workstation 200 or the sub user interface 80 and the operations which have been described as being performed by the user interface 210 may be performed by the mobile device 404. Also, the mobile device 404 may perform both the operations which have been described as being performed by the controller 250 and the operations which have been described as being performed by the user interface 210. In this case, a communication interface provided in the mobile device 404 may perform communication with the workstation 200 and obtain information for performing the operations.

Figure 5:
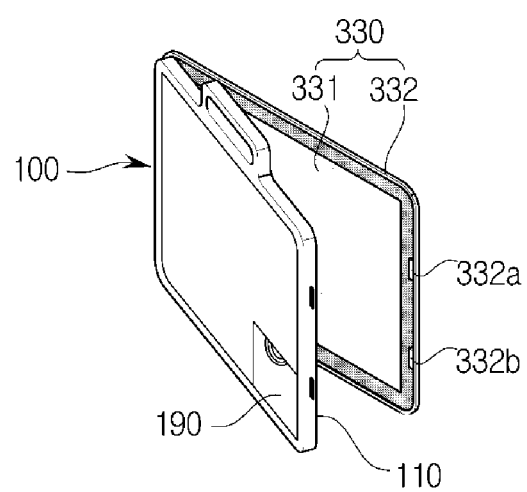
FIG. 5 is a view of an x-ray detector provided to be portable according to an exemplary embodiment.

FIG. 5 is a view of the x-ray detector 100 provided to be portable according to an exemplary embodiment.

The x-ray detector 100 may be mounted on the portable mounting portion 330. The portable mounting portion 330 includes a grid 331, which reduces an amount of scattered rays which arrive at the x-ray detector 100, and a frame 332, which forms a circumference of the grid 331.

The grid 331 may be formed by mixing a material having a high x-ray absorption rate and a material having a low x-ray absorption rate. The grid 331 may be formed in a shape which includes one or more thin plates having a high x-ray absorption rate and a material having a low x-ray absorption rate provided between the thin plates. The thin plate, that is, an absorbing pattern layer may be formed of one of lead, bismuth, gold, barium, tungsten, platinum, mercury, indium, thallium, palladium, tin, zinc, and an alloy thereof but is not limited thereto. The material having the low x-ray absorption rate may be formed of one of plastic, polymer, ceramic, graphite, and carbon fiber but is not limited thereto.

Also, the grid 331 may be provided as a focused grid in which the thin plates are arranged toward a focus at angles, a parallel grid in which the thin plates are arranged in parallel, or a crossed grid in a shape in which a plurality of parallel grids are stacked but is not limited thereto.

One or more protrusions 332*a* and 332*b* are formed on the frame 332, and the x-ray detector 100 may be coupled with the portable mounting portion 330 by fitting on the protrusions 332*a* and 332*b*. However, it is not limited thereto. The portable mounting portion 330 may have another structure in addition to a structure with protrusions or may employ another method in addition to the fitting method as long as the x-ray detector 100 can be coupled with the portable mounting portion 330. A plurality of such portable mounting portions 330 may be provided. The plurality of portable mounting portions 330 may have mutually different shapes. For example, one portable mounting portion 330 may have a handle as shown in FIG. 5 and another portable mounting portion 330 may have a selfie-mount and a selfie-pole.

The portable mounting portion 330 coupled with the x-ray detector 100 forms a cover of an incident surface 110. The grid 331 may be disposed in front of the incident surface 110 and may reduce a scattering amount of x-rays incident on the x-ray detector 100 or may prevent scattering of x-rays.

The x-ray detector 100 may move while being mounted on the portable mounting portion 330 and may be portably used. The x-ray detector 100 moves while being mounted on the portable mounting portion 330 and is allowed to take images of an object in or at various positions, directions, and angles.

As described above, the x-ray detector 100 may be mounted on the table mounting portion 310 or may be mounted on the stand mounting portion 320. Also, the x-ray detector 100 may not be mounted on the table mounting portion 310 or the stand mounting portion 320 to be portably provided or may be mounted on the portable mounting portion 330 to be portably provided. As such, depending on a position of mounting the x-ray detector 100 or whether the x-ray detector 100 is mounted, a table type, a stand type, and a portable type will be defined. The x-ray detector 100 to be mounted on the table mounting portion 310 is defined as a table type x-ray detector. The x-ray detector 100 to be mounted on the stand mounting portion 320 is defined as a stand type x-ray detector. The x-ray detector 100 which is not mounted on the table mounting portion 310 or the stand mounting portion 320 to be portably provided or is mounted on the portable mounting portion 330 to be portably provided is defined as a portable type x-ray detector.

Also, hereinafter, expressions 'being mounted on the table mounting portion 310', 'being embodied as a table type', and 'being provided as a table type' will be all the same. Likewise, expressions 'being mounted on the stand mounting portion 320', 'being embodied as a stand type', and 'being provided as a stand type' will be all the same. Also, 'being portably provided', 'being embodied as a portable type', and 'being provided as a portable type' will be all the same.

The x-ray detector 100 may be singularly provided. The single x-ray detector 100 may be embodied as a table type, a stand type, or a portable type. Also, the x-ray detector 100 may be provided in plural. The plurality of x-ray detectors 100 may be embodied as mutually different types. All or some of the plurality of x-ray detectors 100 may be embodied as the same type.

FIG. 6 is a front view of the x-ray detectors 100 which include the detector display 190.

As shown in FIG. 6, the x-ray detectors 100 are provided as T1, T2, T3, and T4. The plurality of x-ray detectors T1, T2, T3, and T4 each includes the detector display 190. When the x-ray detector T2 is selected for setting among the plurality of x-ray detectors T1, T2, T3, and T4, the detector display 190 of the x-ray detector T2 is turned on or maintains an on state. On the other hand, the detector displays 190 of the other x-ray detectors T1, T3, and T4 are turned off or maintain an off state. Depending on displaying on/off of the detector displays 190, the user may recognize that the x-ray detector T2 is a detector selected for setting.

The detector display 190, as shown in FIG. 3, is provided at a bottom end of the incident surface 110 but is not limited thereto as long as the user can recognize connection.

In the above, a configuration of the x-ray imaging apparatus has been described. Hereinafter, referring to FIGS. 7A to 13, a modality of the x-ray imaging apparatus will be described.

Figure 7A:
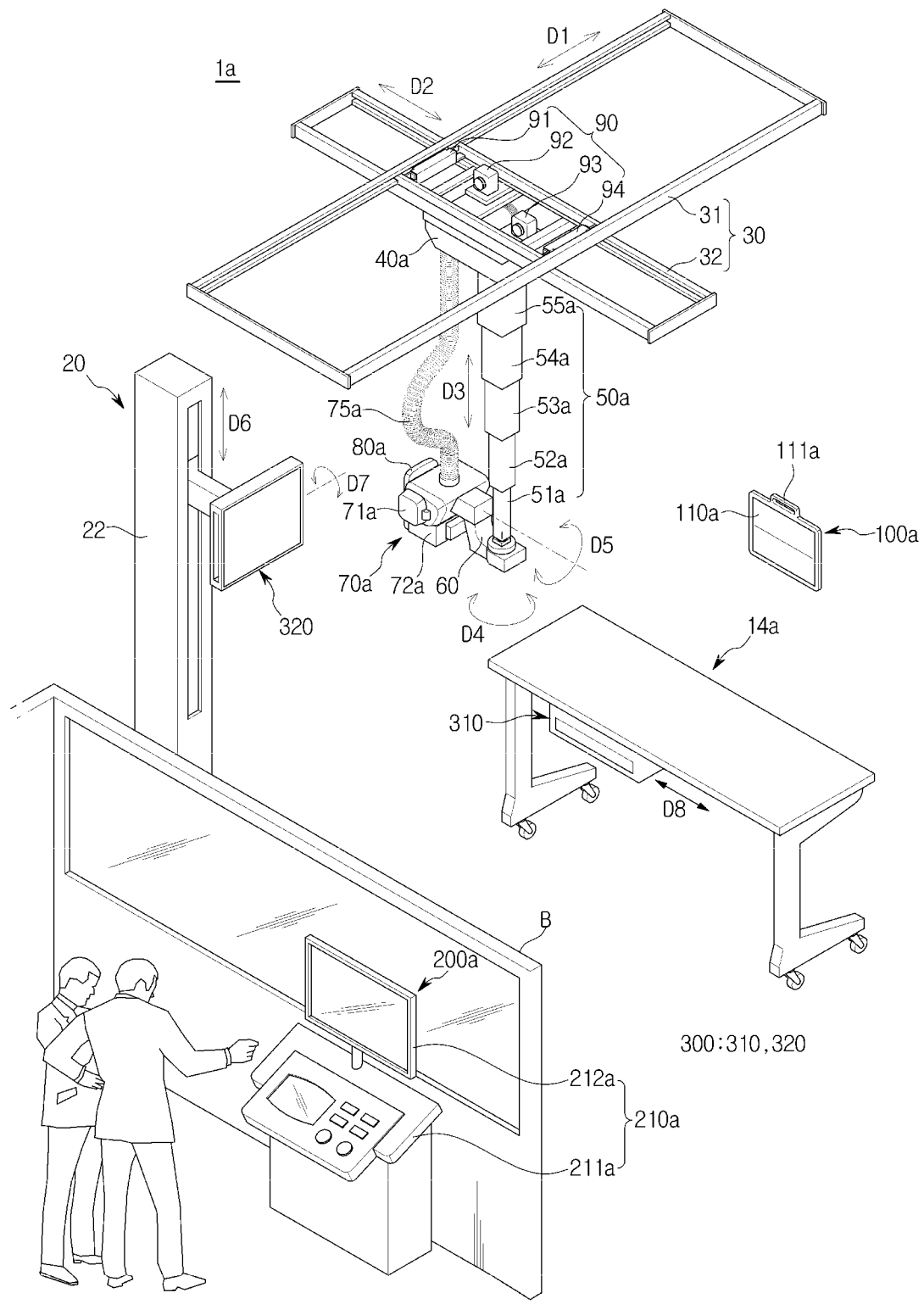
FIG. 7A is a perspective view of a ceiling type x-ray imaging apparatus according to an exemplary embodiment.

FIG. 7A illustrates an exterior of a ceiling type x-ray imaging apparatus 1a.

The x-ray imaging apparatus 1a may include a guide rail 30, a moving carriage 40a, a post frame 50a, motors 91, 92, 93, 94, and 95, an x-ray source 70a, an x-ray detector 100a, a sub user interface 80a, and a workstation 200a. The x-ray imaging apparatus 1a may further include an imaging table 10 and an imaging stand 20 on which the x-ray detector 100a may be mounted.

The guide rail 30, the moving carriage 40a, and the post frame 50a are provided to move the x-ray source 70a toward an object.

The guide rail 30 includes a first guide rail 31 and a second guide rail 32 installed to form an angle. The first guide rail 31 and the second guide rail 32 may extend in a direction of intersection.

The first guide rail 31 is installed on a ceiling of a diagnosis room in which the x-ray imaging apparatus 1a is disposed.

The second guide rail 32 is located below the first guide rail 31 and is slidably mounted on the first guide rail 31. A roller movable along the first guide rail 31 may be installed on the first guide rail 31. The second guide rail 32 may be connected to the roller and may move along the first guide rail 31.

A direction in which the first guide rail 31 extends is defined as a first direction D1, and a direction in which the second guide rail 32 extends is defined as a second direction D2. Accordingly, the first direction D1 and the second direction D2 may intersect with each other and may be in parallel with the ceiling of the diagnosis room.

The moving carriage 40a is disposed below the second guide rail 32 to be movable along the second guide rail 32. A roller provided to move along the second guide rail 32 may be installed on the moving carriage 40a. Accordingly, the moving carriage 40a may move together with the second guide rail 32 in the first direction D1 and may move along the second guide rail 32 in the second direction D2. The post frame 50a is fixed to the moving carriage 40a and located below the moving carriage 40a. The post frame 50a may include a plurality of posts 51a, 52a, 53a, 54a, and 55a.

The plurality of posts 51a, 52a, 53a, 54a, and 55a may be foldably connected with one another in such a way that the post frame 50a may increase or decrease in length in a vertical direction of the diagnosis room while being fixed to the moving carriage 40a.

The direction in which a length of the post frame 50a increases or decreases is defined as a third direction D3. Accordingly, the third direction D3 may intersect with the first direction D1 and the second direction D2.

The x-ray source 70a is an apparatus which emits x-rays to an object. The x-ray source 70a may include an x-ray tube 71a which generates x-rays and a collimator 72a which guides the generated x-rays toward the object. Here, the object may be a living body of a human or an animal but is not limited thereto. The object may be anything whose internal structure may be imaged by the x-ray imaging apparatus 1a.

Between the x-ray source 70a and the post frame 50a, a swivel joint 60 may be disposed.

The swivel joint 60 couples the x-ray source 70a with the post frame 50a and supports a load applied to the x-ray source 70a.

The swivel joint 60 may include a first swivel joint connected with a lower post 51a of the post frame 50a and a second swivel joint connected with the x-ray source 70a.

The first swivel joint is provided to be rotatable on a central axis of the post frame 50a which extends in the vertical direction of the diagnosis room. Accordingly, the first swivel joint may rotate on a plane perpendicular to the third direction D3. Here, a rotation direction of the first swivel joint 61 may be newly defined. A fourth direction D4 newly defined is a rotation direction of an axis parallel to the third direction D3.

The second swivel joint is rotatably provided on a plane perpendicular to the ceiling of the diagnosis room. Accordingly, the second swivel joint may rotate in a rotation direction of an axis parallel to the first direction D1 or the second direction D2. Here, a rotation direction of the second swivel joint may be newly defined. A fifth direction D5 newly defined is a rotation direction of an axis which extends in the first direction D1 or the second direction D2. The x-ray source 70a may be connected to the swivel joint 60 and may rotatively move in the fourth direction D4 and the fifth direction D5. Also, the x-ray source 70a may be connected to the post frame 50a by the swivel joint 60 and may linearly move in the first direction D1, the second direction D2, and the third direction D3.

A motor 90 may be provided to move the x-ray source 70a in the first direction D1 to the fifth direction D5. The motor 90 may be an electrically driven motor and may include an encoder.

The motor 90 may include first, second, third, fourth, and fifth motors 91, 92, 93 and 94 corresponding to the respective directions.

The respective motors 91, 92, 93 and 94 may be disposed in various positions considering convenience of design. For example, the first motor 91 which moves the second guide rail 32 in the first direction D1 may be disposed around the first guide rail 31, the second motor 92 which moves the moving carriage 40a in the second direction D2 may be disposed around the second guide rail 32, and the third motor 93 which increases or reduces the length of the post frame 50a in the third direction D3 may be disposed in the moving carriage 40a. Also, the fourth motor 94 which rotates the x-ray source 70a in the fourth direction D4 may be disposed around the first swivel joint 61, and the fifth motor 95 which rotates the x-ray source 70a in the fifth direction D5 may be disposed around the second swivel joint 62.

The respective motors 90 may be connected with a power transfer unit to linearly or rotatively move the x-ray source 70a in the first direction D1 to the fifth direction D5. The power transfer unit may be a belt, a pulley, a chain, a sprocket, a shaft, etc.

On one side of the x-ray source 70a, the sub user interface 80a which provides a user interface is provided. Here, a user is a person who diagnoses the object using the x-ray imaging apparatus 1a and may be a medical staff including a doctor, a radiologic technician, a nurse, etc. but is not limited thereto. Anyone who uses the x-ray imaging apparatus 1a may be the user.

The user may input various types of information related to x-ray imaging or may operate various apparatuses through inputting the sub input interface 84 or touching the sub display 81.

For example, the user may input a moving direction and position of the x-ray source 70a through the sub input interface 84 or the sub display 81. According to an input of the user, the motor 90 is automatically driven and linearly moves the x-ray source 70a in the first direction D1, the second direction D2, or the third direction D3 or rotatively moves the x-ray source 70a in the fourth direction D4 or the fifth direction D5, thereby locating the x-ray source 70a in the input moving direction and position. This may be defined as an automatic moving mode.

The sub display 81 may be provided as one of a cathode ray tube (CRT), a digital light processing (DLP) panel, a plasma display panel (PDP), a liquid crystal display (LCD) panel, an electroluminescence (EL) panel, an electrophoretic display (EPD) panel, an electrochromic display (ECD) panel, a light emitting diode (LED) panel, and an organic light emitting diode (OLED) panel, but is not limited thereto.

The sub user interface 80a may include a central processing unit (CPU) embodied by a microprocessor, a graphic processing unit (GPU), and various types of storage devices. These may be provided on a built-in printed circuit board (PCB). Because the sub user interface 80a includes the PCB and is provided on one side of the x-ray source 70a, the sub user interface 80a may be referred to as a tube head board (THU).

Also, the sub user interface 80a includes a handle to allow the user to grip. That is, the user may linearly move the x-ray source 70a in the first direction D1 to the third direction D3 or may rotatively move the x-ray source 70a in the fourth direction D4 and the fifth direction D5 by gripping the handle of the sub user interface 80a and applying a force or torque thereto. This may be defined as an automatic moving mode.

Also, the workstation 200a includes a workstation user interface 210a to provide a user interface together with the sub user interface 80a. The workstation user interface 210a may include a workstation input interface 211a and a workstation display 212a, thereby receiving a user command for x-ray imaging or displaying various types of information related to the x-ray imaging. For example, the user may set imaging conditions according to an imaged portion through the workstation user interface 210a or may input a command for moving the moving carriage 40a or the x-ray source 70a or a command for starting x-ray imaging. Also, the user may check images obtained during an x-ray imaging process through the workstation user interface 210a.

The workstation input interface 211a may include various hardware input devices such as various buttons, switches, a keyboard, a mouse, a track-ball, various levers, a handle, or a stick for an input of the user. The workstation input interface 211a may be provided above the workstation 200a as shown in FIG. 7A, but may be provided below the workstation 200a when being embodied as a foot switch and a foot pedal.

Also, for user input, the workstation input interface 211a may include a graphical user interface (GUI) such as a touch pad, that is, a software input device. The touch pad may be provided as a touch screen panel (TSP) and may form a mutual layer structure together with the workstation display 212a.

The workstation display 212a, like the sub display 81 of the sub user interface 80a, may be provided as one of a CRT, a DLP panel, a PDP, an LCD panel, an EL panel, an EPD panel, an ECD panel, an LED panel, and an OLED panel but is not limited thereto.

As described above, when being configured as the TSP formed of the mutual layer structure together with the touch pad, the workstation display 212a may be used as an input device in addition to a display device.

Also, a PCB which includes various processing units such as CPU and GPU and various storage devices may be built in the workstation 200a. Accordingly, the workstation 200a may accommodate a primary component of the x-ray imaging apparatus 1a, for example, a controller to perform various types of determination for an operation of the x-ray imaging apparatus 1a or to generate various control signals.

A barrier B for preventing x-rays is provided between the workstation 200a and the diagnosis room in such a way that the user may input information or may operate the apparatus while not being exposed to x-rays due to the barrier B during an x-ray imaging process.

The x-ray detector 100a is an apparatus which detects x-rays which penetrate an object. An incident surface 110a on which x-rays which penetrate the object are incident is provided on a front surface of the x-ray detector 100a, and a sensing panel which detects the incident x-rays is provided in the x-ray detector 100a. A plurality of pixels which respond to x-rays may be arranged in a matrix shape in the sensing panel 120. A handle 111a may be provided in a middle of a top of the x-ray detector 100a to provide convenience to the user while moving or carrying the x-ray detector 100a.

A battery which supplies power to the sensing panel 120 and a detector sensor 140 to operate the x-ray detector 100a is provided on a rear surface of the x-ray detector 100a. The battery may include a chargeable secondary cell and may be detachably provided.

Also, the x-ray detector 100a may have various sizes. For example, the x-ray detector 100a may have sizes of 43×35 cm, 43×43 cm, and 30×25 cm.

The x-ray detector 100a may be mounted on the imaging table 10 or the imaging stand 20 during an x-ray imaging. To mount the x-ray detector 100a, the mounting portions 300 may be provided at the imaging table 10 and the imaging stand 20, respectively. Here, the mounting portion 300 provided at the imaging table 10 will be defined as a table mounting portion 310 and the mounting portion 300 provided at the imaging stand 20 will be defined as a stand mounting portion 320.

As shown in FIG. 7A, the stand mounting portion 320 may be provided to be movable in a longitudinal direction of a support 22 and to be rotatable in a rotation direction of an axis perpendicular to the longitudinal direction of the support 22. Also, the table mounting portion 310 may be provided to be movable in a longitudinal direction of the imaging table 10. Here, the longitudinal direction of the support 22 will be defined as a sixth direction D6, the rotation direction of the axis perpendicular to the sixth direction D6 will be defined as a seventh direction D7, and the longitudinal direction of the imaging table 10 will be defined as an eighth direction D8.

Also, a size of the mounting portion 300 may vary according to a size of the x-ray detector 100 to be used. Hereinafter, it will be described with reference to FIG. 7B.

FIG. 7B is a conceptual view illustrating the x-ray detector 100 compatible through changing a size of a mounting portion in the ceiling type x-ray imaging apparatus 1a according to an exemplary embodiment.

As shown in FIG. 7B, the ceiling type x-ray imaging apparatus 1a may change the size of the mounting portion, thereby changing the number of the mounting portions on which a x-ray detector 100 is mountable.

In detail, the ceiling type x-ray imaging apparatus 1a may include the table mounting portion 310, the stand mounting portion 320, a first portable mounting portion 330a, and a second portable mounting portion 330b. Here, a size of the x-ray detector 100 mountable on the table mounting portion 310 is 43×43 cm, a size of the x-ray detector 100 mountable on the stand mounting portion 320 is 43×43 cm, a size of the x-ray detector 100 mountable on the first portable mounting portion 330a is 43×35 cm, and a size of the x-ray detector 100 mountable on the second portable mounting portion 330b is 30×25 cm. Also, a size of the x-ray detector 100, selected through the user interface 210, is 43×35 cm.

In this case, because the size of the x-ray detector 100 selected through the user interface 210 is 43×35 cm, a mounting portion on which the selected x-ray detector 100 is mountable may be only the first portable mounting portion 330a.

However, to allow the selected x-ray detector 100 to be mountable not only on the first portable mounting portion 330a but also on the table mounting portion 310 and the stand mounting portion 320, sizes of the table mounting portion 310 and the stand mounting portion 320 may be adjusted. That is, the ceiling type x-ray imaging apparatus 1a may mount the selected x-ray detector 100 having the size of 43×35 cm on the table mounting portion 310 and the stand mounting portion 320 by adjusting sizes of areas of the table mounting portion 310 and the stand mounting portion 320, on which the x-ray detector 100 is to be mounted, from 43×43 cm to 43×35 cm. Accordingly, the x-ray detector 100 having the size of 43×35 cm, which is mounted on the first portable mounting portion 330a, may be mounted on the table mounting portion 310 and the stand mounting portion 320.

When the size of the mounting portion 300 is adjusted and then the size of the x-ray detector 100 mounted on the mounting portion 300 is changed, the x-ray imaging apparatus 1a may adjust a center or focus of x-rays emitted by the x-ray source 70a and signal arrangement of intensity of x-rays for each pixel received by the x-ray detector 100 according to the size of the x-ray detector 100. The adjustment may be performed based on the mounting portion data 278 stored in the storage 270.

Also, the mounting portion 300 may include a rail to adjust the size of the area in which the x-ray detector 100 is mounted. Also, the mounting portion 300 may be adjustable in the size of the area in which the x-ray detector 100 is mounted using a force applied by the user or a motor included in the mounting portion 300. Also, the mounting portion 300 may be adjusted in size according to an input of an additional button of the user interface 210 or the sub user interface 80 or may be displayed on the user interface 210 to be adjusted in size according to the graphic user interface which receives a command of the user. In addition, various methods of adjusting a mounting area for the x-ray detector 100 in the mounting portion 300 may be used as an example of adjusting the size of the mounting portion 300.

Figure 8A:
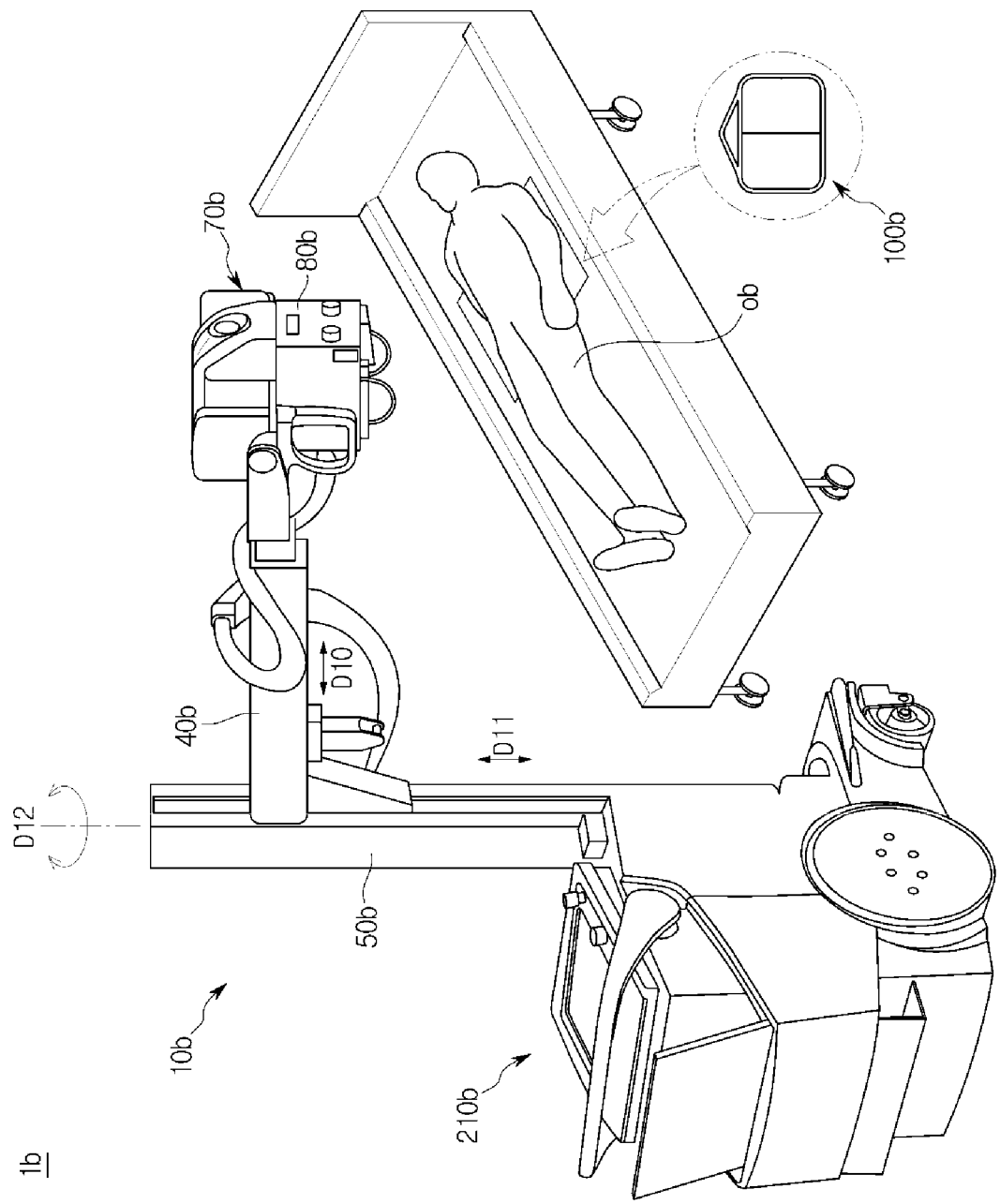
FIG. 8A is a perspective view of a mobile type x-ray imaging apparatus according to an exemplary embodiment.

FIG. 8A is a perspective view of a mobile type x-ray imaging apparatus 1b.

In the x-ray imaging apparatus 1b, both an x-ray source 70b and an x-ray detector 100b may be freely movable in a three-dimensional (3D) random space. In detail, the x-ray source 70b is mounted on a movable body 10b through a supporting arm and the supporting arm is rotatable and adjustable in height, thereby allowing the x-ray source 70b to freely move. Also, because the portable mounting portion 330 is used in the x-ray imaging apparatus 1b, the x-ray detector 100b may also be located in a random position in a 3D space.

The supporting arm is mounted on the movable body 10b of the x-ray imaging apparatus 1b, and the x-ray source 70b is mounted on an end of the supporting arm. The supporting arm is rotatable about a center thereof in a direction parallel to the ground.

The supporting arm includes a first supporting arm 40b on which the x-ray source 70b is mounted and a second supporting arm 50b mounted on the body 10b. The first supporting arm 40b and the second supporting arm 50b may meet and be connected to each other at a rail of the second supporting arm 50b. Also, the first supporting arm 40b may move along the rail of the second supporting arm 50b in a vertical direction D11 and may be adjusted in length in a direction D10 parallel to the first supporting arm 40b. Also, the second supporting arm 50b may rotate in a direction D12 parallel to the ground. Accordingly, the x-ray source 70b may freely move in the 3D random space.

Meanwhile, FIG. 8A illustrates an example of an exterior of the x-ray imaging apparatus 1b. The supporting arm may be integrally embodied, and a sub supporting arm which forms the supporting arm such as the first supporting arm 40b and the second supporting arm 50b may be additionally added.

The x-ray detector 100b, as shown in FIG. 8A, may transmit and receive generated signals with the body 10b through wireless communication but may communicate over wires through a cable physically connected therebetween.

The x-ray detector 100b described above may be applied as a film type cassette, a computed radiography (CR) cassette, a digital radiography (DR) cassette, etc. but is not limited thereto.

A plurality of casters are provided below the body 10b and a handle is provided on an upper portion of the body 10b, thereby fixing the x-ray imaging apparatus 1b to a position or moving the x-ray imaging apparatus 1b in a direction.

Also, a user interface 210b which receives a command of the user and displays images obtained during an x-ray diagnosis process may be provided in the upper portion of the body 10b.

Also, a mounting portion may be adjusted in size according to a size of an x-ray detector to be used. Hereinafter, it will be described with reference to FIG. 8B.

FIG. 8B is a conceptual view illustrating an x-ray detector compatible through changing a size of a mounting portion in the mobile type x-ray imaging apparatus 1b according to an exemplary embodiment.

As shown in FIG. 8B, the mobile type x-ray imaging apparatus 1b may change the size of the mounting portion, thereby changing the number of the mounting portions on which a x-ray detector 100 is mountable.

In detail, the mobile type x-ray imaging apparatus 1b may include the first portable mounting portion 330a and the second portable mounting portion 330b. Here, a size of the x-ray detector 100 mountable on the first portable mounting portion 330a is 43×35 cm, and a size of the x-ray detector 100 mountable on the second portable mounting portion 330b is 30×25 cm. Also, a size of the x-ray detector 100, selected through the user interface 210, is 30×25 cm.

In this case, because the size of the x-ray detector 100 selected through the user interface 210 is 30×25 cm, a mounting portion on which the selected x-ray detector 100 is mountable may be only the second portable mounting portion 330b.

However, the size of the first portable mounting portion 330a may be adjusted to mount the selected x-ray detector 100 not only on the second portable mounting portion 330b but also on the first portable mounting portion 330a. That is, the mobile type x-ray imaging apparatus 1b may mount the selected x-ray detector 100 having the size of 30×25 cm on the first portable mounting portion 330a by adjusting a size of an area of the first portable mounting portion 330a, on which the x-ray detector 100 is to be mounted, from 43×35 cm to 30×25 cm. Accordingly, the x-ray detector 100 having the size of 30×25 cm, which is mounted on the second portable mounting portion 330b, may be mounted on the first portable mounting portion 330a.

When the size of the mounting portion 300 is adjusted and then the size of the x-ray detector 100 mounted on the mounting portion 300 is changed, the x-ray imaging apparatus 1b may adjust a center or focus of x-rays emitted by the x-ray source 70b and signal arrangement of intensity of x-rays for each pixel received by the x-ray detector 100 according to the size of the x-ray detector 100. The adjustment may be performed based on the mounting portion data 278 stored in the storage 270.

Also, the mounting portion 300 may include a rail to adjust the size of the area in which the x-ray detector 100 is mounted. Also, the mounting portion 300 may adjust the size of the area in which the x-ray detector 100 is mounted using a force applied by the user or a motor included in the mounting portion 300. Also, the mounting portion 300 may be adjusted in size according to an input of an additional button of the user interface 210 or a sub user interface 80b or may be displayed on the user interface 210 to be adjusted in size according to the graphic user interface which receives a command of the user. In addition, various methods of adjusting a mounting area for the x-ray detector 100 in the mounting portion 300 may be used as an example of adjusting the size of the mounting portion 300.

Figure 9:
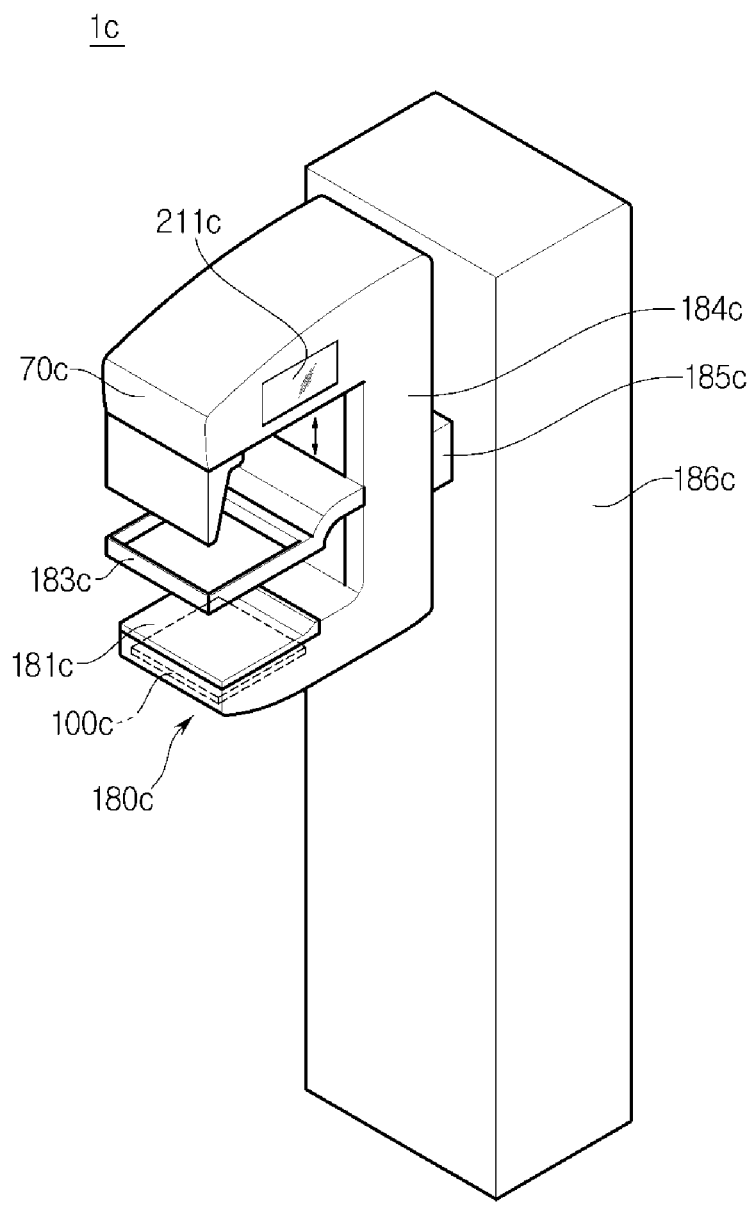
FIG. 9 is a perspective view of a mammography type x-ray imaging apparatus according to an exemplary embodiment.

FIG. 9 is a perspective view of a mammography type x-ray imaging apparatus 1c according to an exemplary embodiment.

An x-ray imaging apparatus may be used to take x-ray images of breasts.

An x-ray source 70c and a detector assembly 180c are connected to a frame 184c at positions facing each other. The frame 184c may be connected with a supporting portion 186c through an arm 185c and the arm 185c may vertically move to be adjusted in height according to the object ob or may rotate at an angle, thereby allowing the x-ray imaging apparatus 1c to obtain tomogram or 3D images of the object ob.

While x-ray imaging, the breasts which are the object ob are located between the x-ray source 70c and the detector assembly 180c to allow x-rays which penetrate the breasts, among x-rays emitted by the x-ray source 70c, to be detected by the detector assembly 180c.

Meanwhile, the detector assembly 180c may perform a function of a support or a table which supports the breasts.

In detail, the detector assembly 180c includes an x-ray detector 100c which detects x-rays therein and further includes a breast contact portion 181c to be in contact with the breasts. The breast contact portion 181c may be formed of a material having excellent ray transmittance and may be embodied, for example, in a carbon sheet.

When the breasts are put on the breast contact portion 181c, the user may operate an input interface 211c to vertically move a compressing paddle 183c.

The user may input a command with respect to a movement of the compressing paddle 183c through the input interface 211c. The input interface 211c may control the movement of the compressing paddle 183c by transmitting a control signal to a paddle driving unit. The paddle driving unit may include a motor and a drive and may further include a structure such as gears for transferring a driving force of the motor to the compressing paddle 183c.

The input interface 211c may be embodied as a foot button or a foot pedal. When the input interface 211c is embodied as the foot button, the user may adjust a position of the breasts, that is, the object ob using hands and may control the movement of the compressing paddle 183c using a foot, thereby efficiently performing compression of the breasts.

Figure 10:
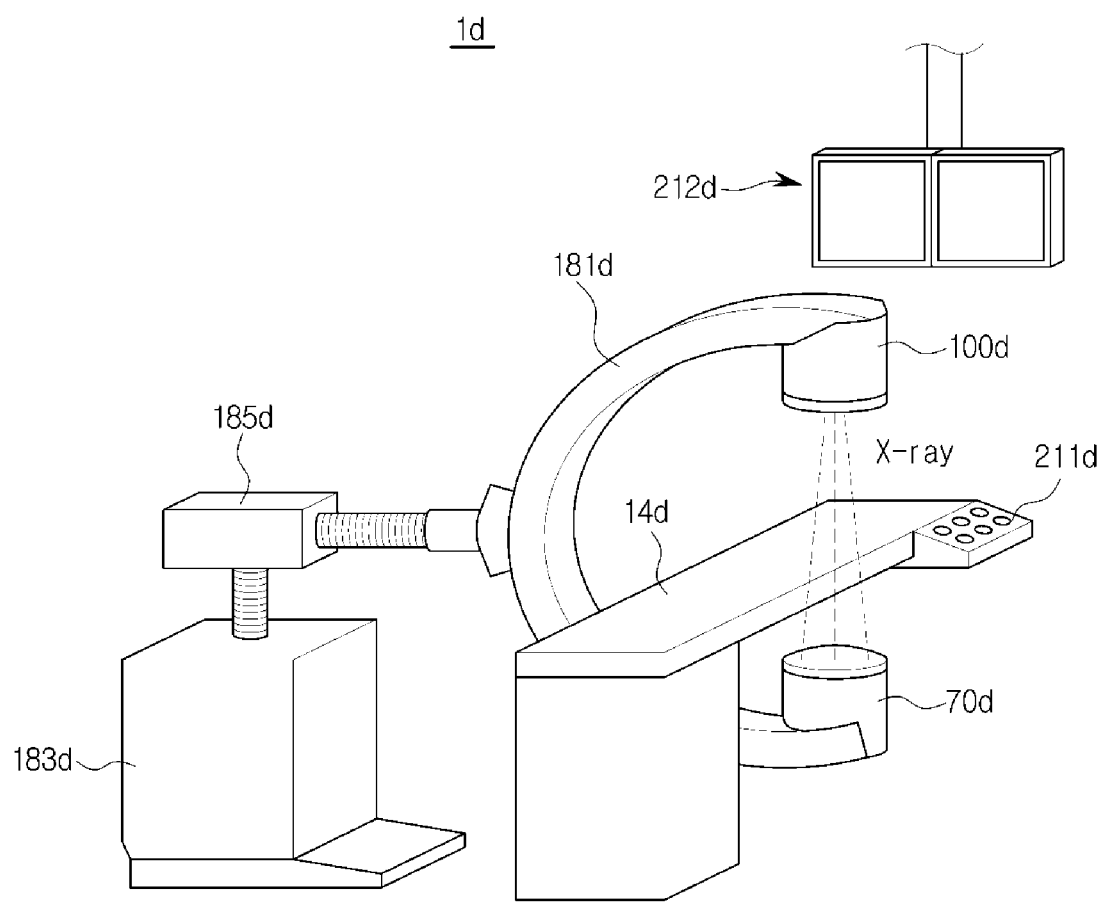
FIG. 10 is a perspective view of an angiography type x-ray imaging apparatus according to an exemplary embodiment.

FIG. 10 is a perspective view of an angiography type x-ray imaging apparatus 1d according to an exemplary embodiment.

The x-ray imaging apparatus 1d may have a C-arm structure. An x-ray source 70d and an x-ray detector 100d may be mounted on both ends of a C-shaped arm 181d, respectively. The C-shaped arm 181d is connected to a supporting portion 183d through a connecting shaft 185d and may rotate in an orbital direction.

In detail, the C-shaped arm 181d is mounted to be rotatable on a horizontal axis. Also, the C-shaped arm 181d may circularly or semicircularly rotate. Also, the C-shaped arm 181d may be mounted on the supporting portion 183d installed on the floor and the supporting portion 183d may rotate on a vertical axis. Accordingly, x-ray images may be obtained in various directions with respect to various regions of interest (ROI) of the object ob through rotations of the C-shaped arm 181d and the supporting portion 183d.

When a table 14d is located between the x-ray source 70d and the x-ray detector 100d and the object ob is located on the table 14d, the x-ray source 70d emits x-rays to the object ob and the x-ray detector 100d detects the emitted x-rays, thereby obtaining x-ray images of the object ob.

Because the x-ray imaging apparatus 1d may obtain real-time moving images of the object ob, the user may perform a medical procedure or diagnosis while looking at a display 212d which includes a plurality of screens and displays several images for the medical procedure or diagnosis and may input a command for controlling the x-ray imaging apparatus 1d through an input interface 211d.

As described above, the x-ray imaging apparatuses having different modalities have been described. Hereinafter, referring to FIGS. 11 to 13, examples of an x-ray imaging apparatus embodied in one diagnosis room will be described.

As described with reference to FIGS. 7A to 10, the x-ray imaging apparatus may use one modality in one diagnosis room but may use a plurality of modalities in one diagnosis room depending on an exemplary embodiment.

Figure 11:
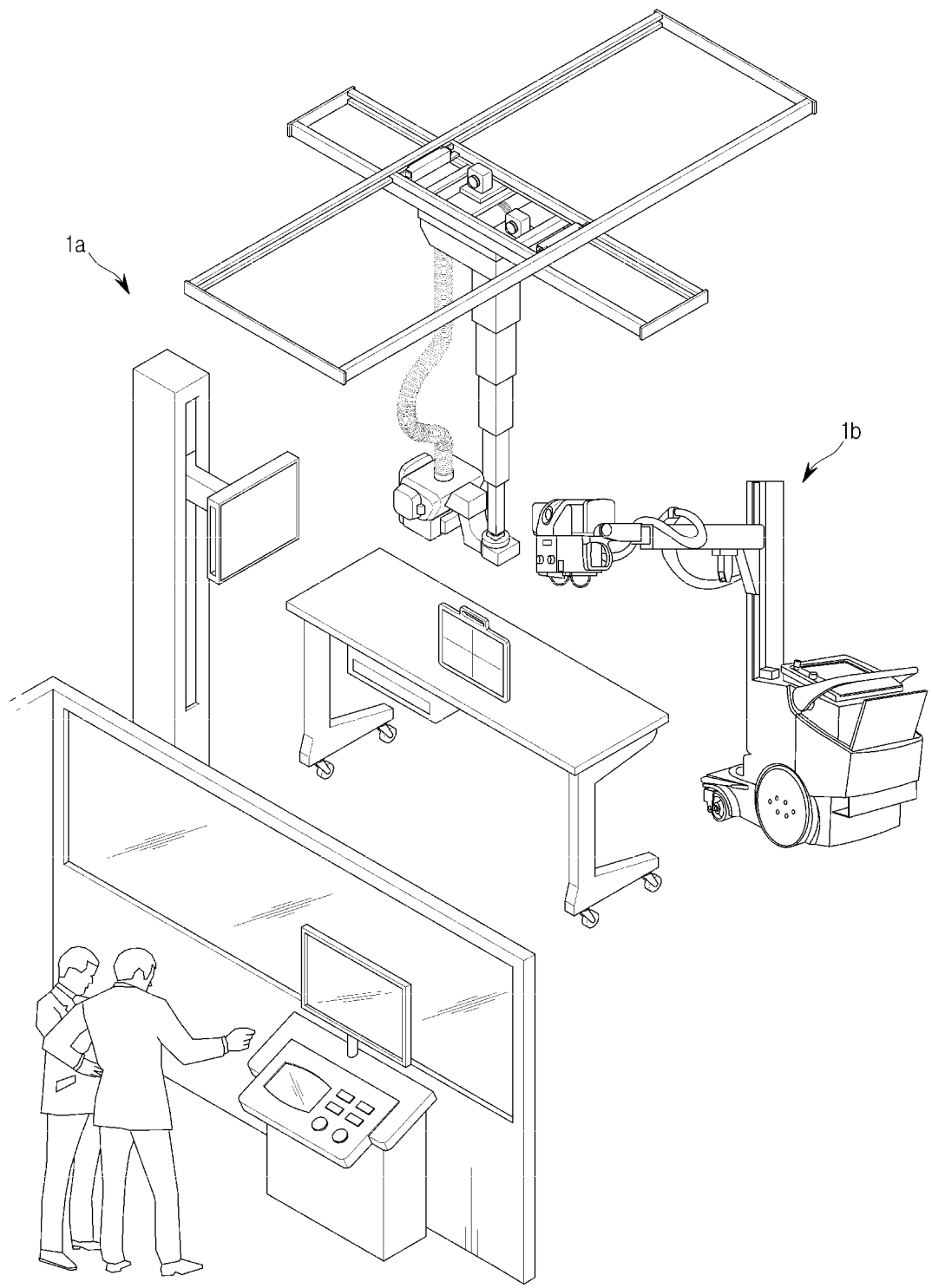
FIG. 11 is a perspective view of an x-ray imaging system using the ceiling type x-ray imaging apparatus and the mobile type x-ray imaging apparatus in one diagnosis room according to an exemplary embodiment.

FIG. 11 is a perspective view of an x-ray imaging system using the ceiling type x-ray imaging apparatus 1a and the mobile type x-ray imaging apparatus 1b in one diagnosis room.

As shown in FIG. 11, the user may use the ceiling type x-ray imaging apparatus 1a and the mobile type x-ray imaging apparatus 1b in one diagnosis room.

In this case, the user may obtain x-ray images of the object ob by primarily using the ceiling type x-ray imaging apparatus 1a. Also, to take images of another portion at the same time while taking images using the ceiling type x-ray imaging apparatus 1a, the mobile type x-ray imaging apparatus 1b may be secondarily used to obtain x-ray images of the object ob.

For example, the user may take images of a chest of the object ob using the stand mounting portion 320 of the ceiling type x-ray imaging apparatus 1a and may take images of a lower body of the object ob using the mobile type x-ray imaging apparatus 1b at the same time.

Figure 12:
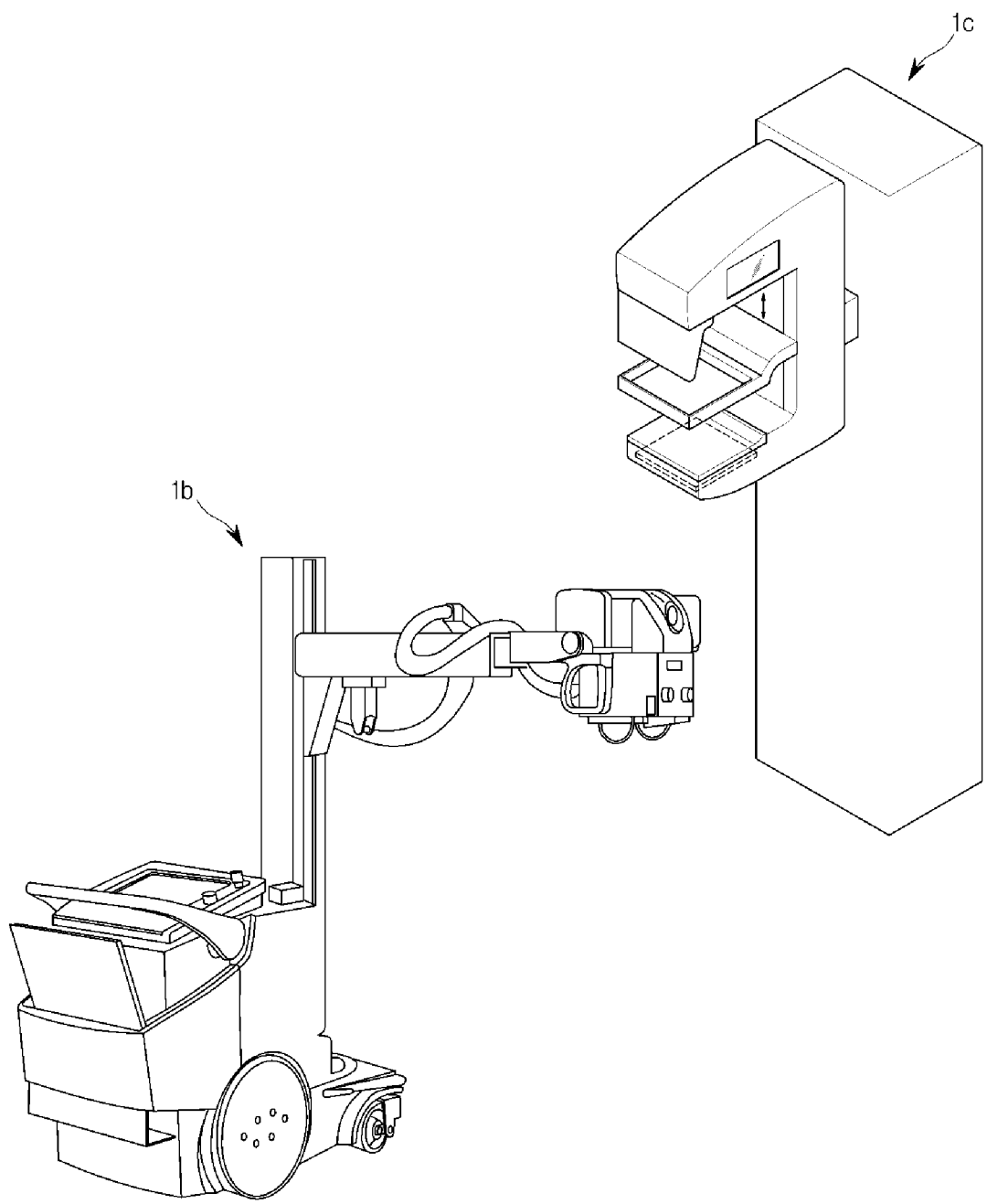
FIG. 12 is a perspective view of an x-ray imaging system using the mammography type x-ray imaging apparatus and the mobile type x-ray imaging apparatus in one diagnosis room according to an exemplary embodiment.

FIG. 12 is a perspective view of an x-ray imaging system using the mammography type x-ray imaging apparatus 1c and the mobile type x-ray imaging apparatus 1b in one diagnosis room.

As shown in FIG. 12, the user may use the mammography type x-ray imaging apparatus 1c and the mobile type x-ray imaging apparatus 1b in one diagnosis room.

In this case, the user may obtain x-ray images of the object ob by primarily using the mammography type x-ray imaging apparatus 1c. Also, to take images of another portion at the same time while taking images using the mammography type x-ray imaging apparatus 1c, the mobile type x-ray imaging apparatus 1b may be secondarily used to obtain x-ray images of the object ob.

For example, the user may take images of a chest of the object ob using the mammography type x-ray imaging apparatus 1c and may take images of a lower body of the object ob using the mobile type x-ray imaging apparatus 1b at the same time.

Figure 13:
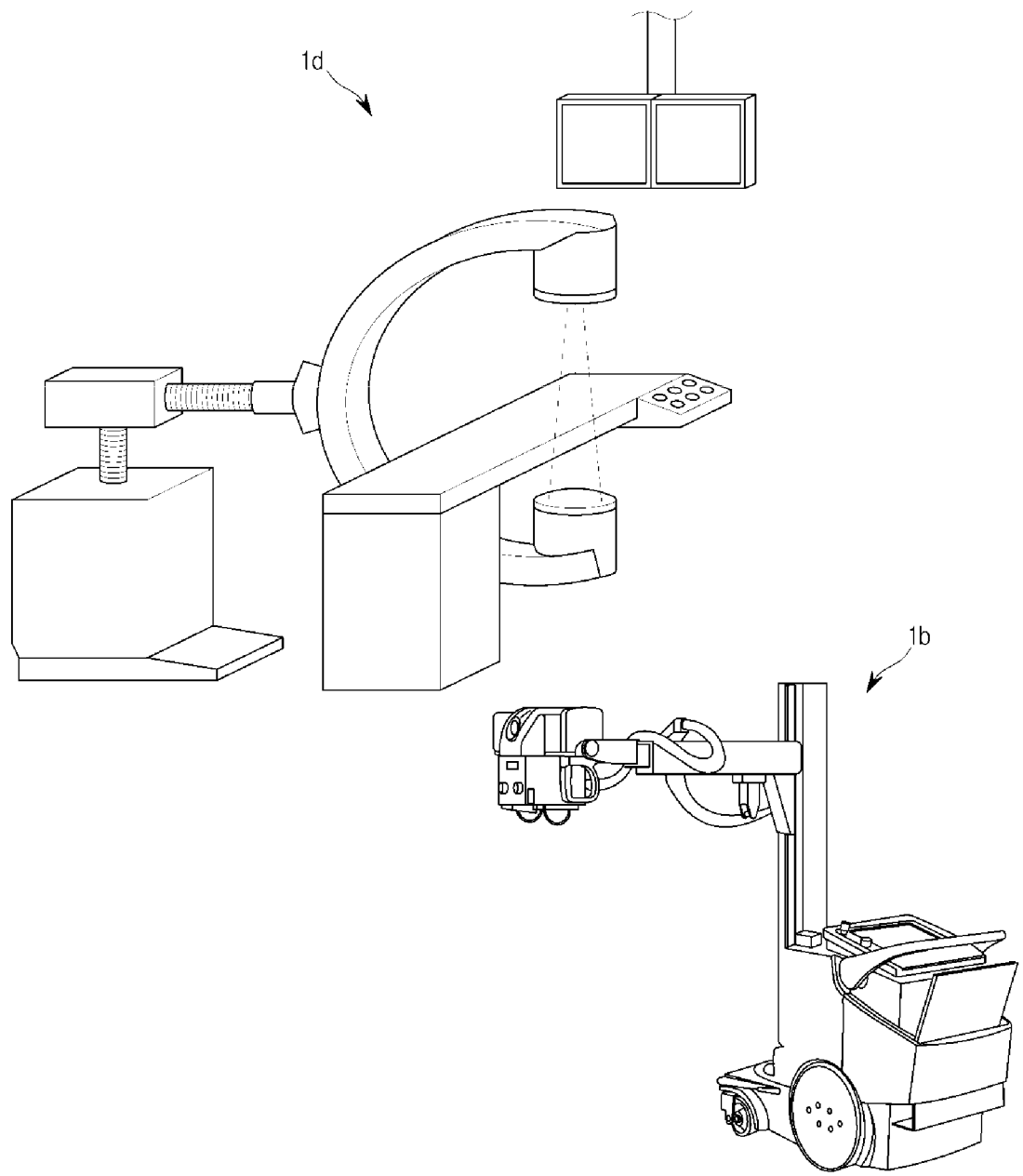
FIG. 13 is a perspective view of an x-ray imaging system using the angiography type x-ray imaging apparatus and the mobile type x-ray imaging apparatus in one diagnosis room according to an exemplary embodiment.

FIG. 13 is a perspective view of an x-ray imaging system using the angiography type x-ray imaging apparatus 1d and the mobile type x-ray imaging apparatus 1b in one diagnosis room.

As shown in FIG. 13, the user may use the angiography type x-ray imaging apparatus 1d and the mobile type x-ray imaging apparatus 1b in one diagnosis room.

In this case, the user may obtain x-ray images of the object ob by primarily using the angiography type x-ray imaging apparatus 1d. Also, to take images of another portion at the same time while taking images using the angiography type x-ray imaging apparatus 1d, the mobile type x-ray imaging apparatus 1b may be secondarily used to obtain x-ray images of the object ob.

For example, the user may take images of an upper body of the object ob using the angiography type x-ray imaging apparatus 1d in real time and may display x-ray images and may take images of a lower body of the object ob using the mobile type x-ray imaging apparatus 1b at the same time.

In addition to the cases of embodying the x-ray imaging apparatus 1 having a plurality of modalities in one diagnosis room described with reference to FIGS. 11 to 13, various combinations of modalities may be available. For example, the ceiling type x-ray imaging apparatus 1a, the mobile type x-ray imaging apparatus 1b, and the mammography type x-ray imaging apparatus 1c may be embodied in one diagnosis room. Also, the ceiling type x-ray imaging apparatus 1a, the mammography type x-ray imaging apparatus 1c, and the angiography type x-ray imaging apparatus 1d may be embodied in one diagnosis room. Also, the ceiling type x-ray imaging apparatus 1a, the mobile type x-ray imaging apparatus 1b, and the angiography type x-ray imaging apparatus 1d may be embodied in one diagnosis room. Also, the mobile type x-ray imaging apparatus 1b, the mammography type x-ray imaging apparatus 1c, and the angiography type x-ray imaging apparatus 1d may be embodied in one diagnosis room. Also, the ceiling type x-ray imaging apparatus 1a, the mobile type x-ray imaging apparatus 1b, the mammography type x-ray imaging apparatus 1c, and the angiography type x-ray imaging apparatus 1d may be embodied in one diagnosis room.

Hereinafter, referring to FIGS. 14 and 15, examples of moving a detector from one diagnosis room to another diagnosis room will be described.

The plurality of x-ray detectors 100 included in the x-ray imaging apparatus 1 are located in a diagnosis room in which the workstation 200 is located and connected to the workstation 200 to take x-ray images of the object ob. However, when there are a plurality of diagnosis rooms and it is impossible to use the x-ray detector 100 in an adjacent diagnosis room due to a failure, loss, and other causes, the x-ray detector 100 located in another diagnosis room may be temporarily used. This is referred to as room-sharing or a swap. It will be performed in various methods depending on a communication method between the x-ray detector 100 and the workstation 200.

Figure 14:
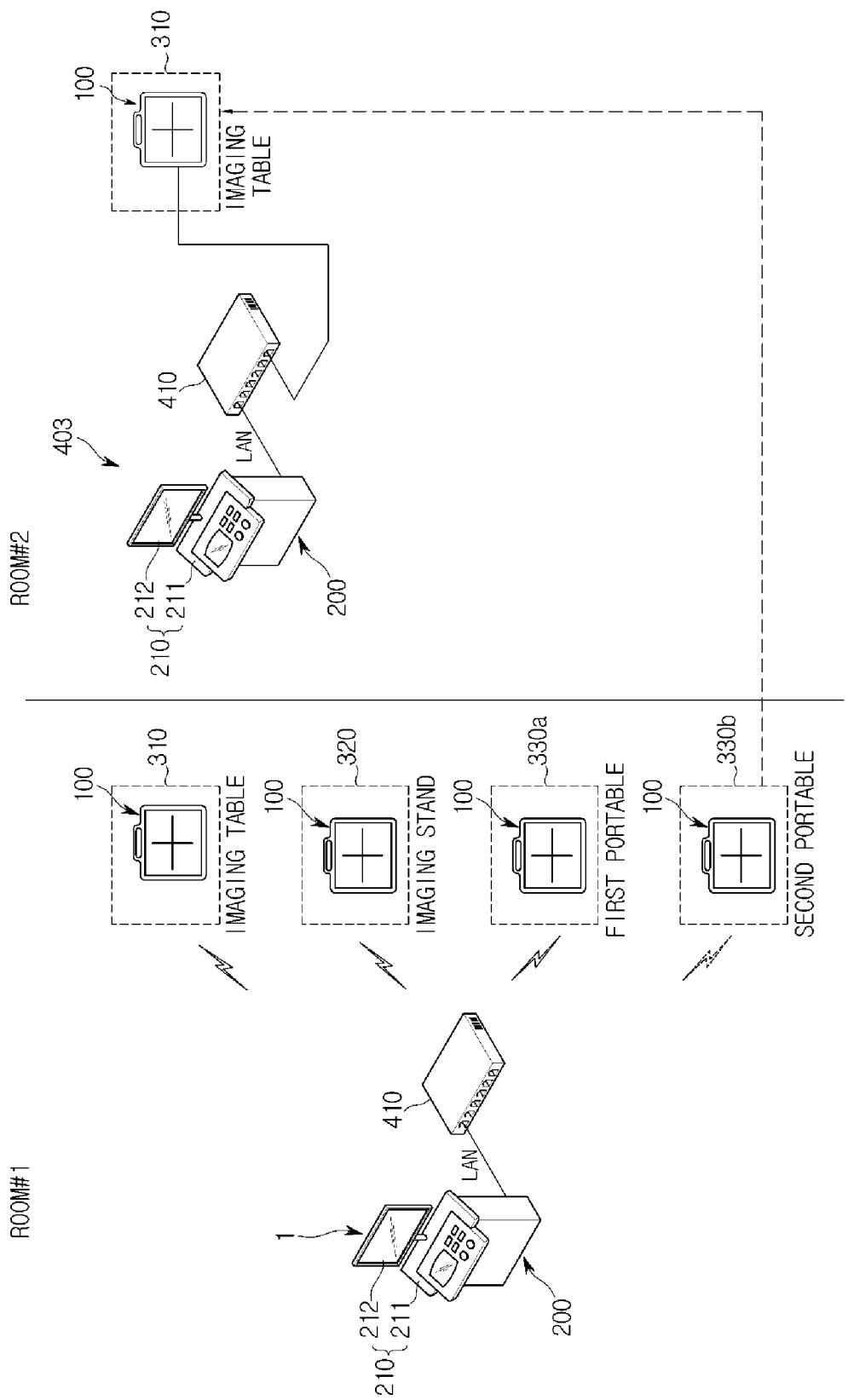
FIG. 14 is a conceptual view illustrating that a detector located in one diagnosis room is moved to another diagnosis room to connect the detector to a workstation according to an exemplary embodiment.

FIG. 14 is a conceptual view illustrating that a detector located in one diagnosis room is moved to another diagnosis room to connect the detector to a workstation according to an exemplary embodiment.

As shown in FIG. 14, the x-ray imaging apparatus 1 is provided in a first diagnosis room ROOM #1, and another medical apparatus 403 which takes x-ray images is provided in a second diagnosis room ROOM #2. When the x-ray detector 100 in the second diagnosis room ROOM #2 is not usable, the other medical apparatus 403 may bring the x-ray detector 100 of the x-ray imaging apparatus 1 to the second diagnosis room ROOM #2 and may temporarily use it.

As shown in FIG. 14, when the workstation 200 in the first diagnosis room ROOM #1 is wirelessly connected with the four x-ray detectors 100, the user may mount the x-ray detector 100 mounted on the second portable mounting portion 330b of the first diagnosis room ROOM #1 on the table mounting portion 310 of the second diagnosis room ROOM #2. In this case, the x-ray detector 100 mounted on the table mounting portion 310 of the second diagnosis room ROOM #2 may be connected with the other medical apparatus 403 through wired communication and may maintain wireless communication with the x-ray imaging apparatus 1. Also, the other medical apparatus 403 and the x-ray imaging apparatus 1 may be connected to each other through the network 400. Also, the other medical apparatus 403 may set the x-ray detector 100 mounted on the table mounting portion 310 based on the previously stored detector pairing data 271 or the setting information of the x-ray imaging apparatus 1.

FIG. 15 is a conceptual view illustrating that a detector located in one diagnosis room is moved to another diagnosis room to connect the detector to a workstation according to an exemplary embodiment.

As shown in FIG. 15, the x-ray imaging apparatus 1 is provided in the first diagnosis room ROOM #1, and the other medical apparatus 403 which takes x-ray images is provided in the second diagnosis room #2. When the x-ray detector 100 in the second diagnosis room ROOM #2 is not usable, the other medical apparatus 403 may bring the x-ray detector 100 of the x-ray imaging apparatus 1 to the second diagnosis room ROOM #2 and may temporarily use it.

As shown in FIG. 15, when the workstation 200 in the first diagnosis room ROOM #1 is wirelessly connected with the four x-ray detectors 100, the user may mount the x-ray detector 100 mounted on the stand mounting portion 320 of the first diagnosis room ROOM #1 on the stand mounting portion 320 of the second diagnosis room ROOM #2. In this case, the x-ray detector 100 mounted on the stand mounting portion 320 of the second diagnosis room ROOM #2 may be connected with the other medical apparatus 403 through wireless communication and may be disconnected from wireless communication with the x-ray imaging apparatus 1. Also, the other medical apparatus 403 and the x-ray imaging apparatus 1 may be connected to each other through the network 400. Also, the other medical apparatus 403 may set the x-ray detector 100 mounted on the stand mounting portion 320 based on the previously stored detector pairing data 271 or the setting information of the x-ray imaging apparatus 1.

Figure 16:
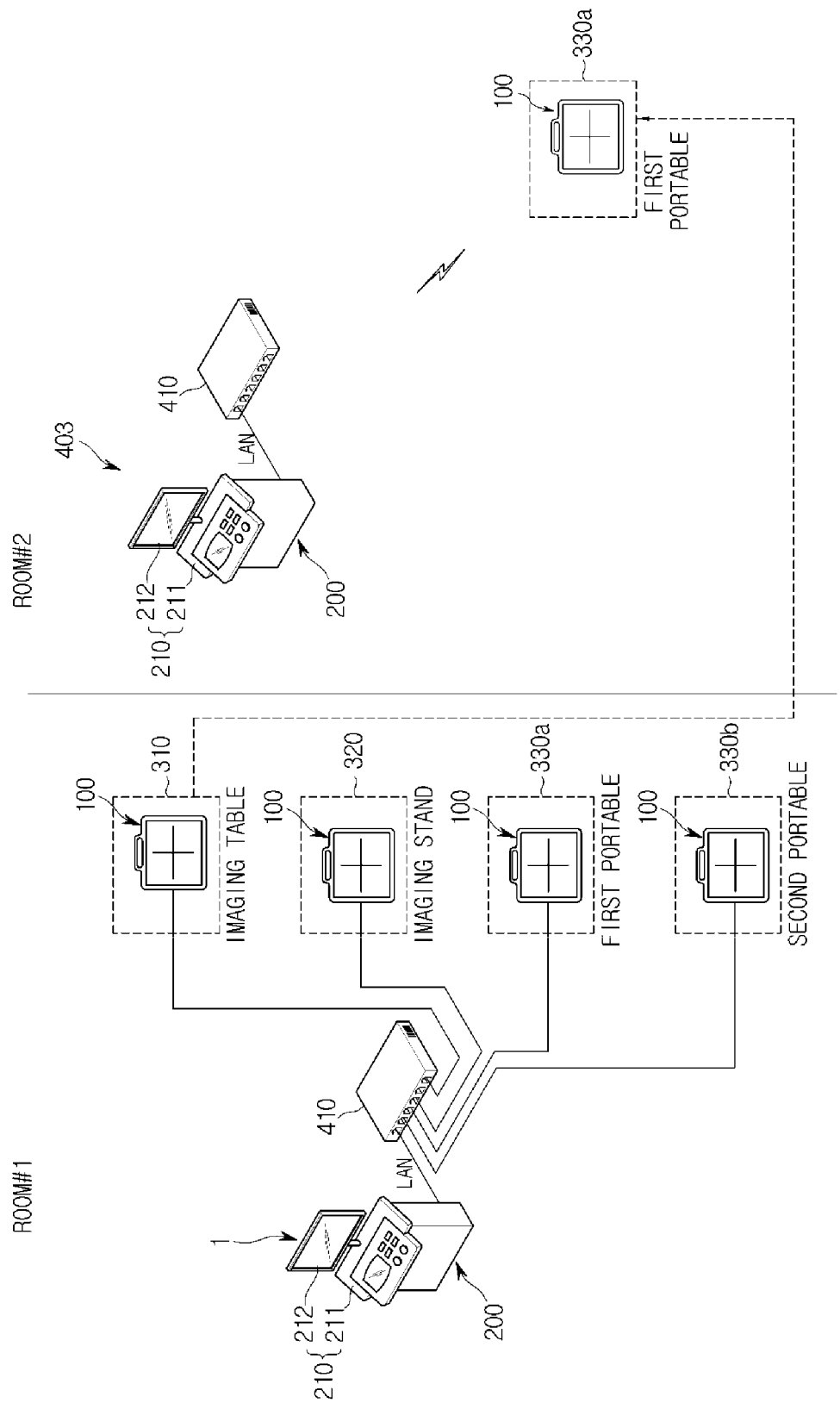
FIG. 16 is a conceptual view illustrating that a detector located in one diagnosis room is moved to another diagnosis room to connect the detector to a workstation according to an exemplary embodiment.

FIG. 16 is a conceptual view illustrating that a detector located in one diagnosis room is moved to another diagnosis room to connect the detector to a workstation according to an exemplary embodiment.

As shown in FIG. 16, the x-ray imaging apparatus 1 is provided in the first diagnosis room ROOM #1, and the other medical apparatus 403 which takes x-ray images is provided in the second diagnosis room #2. When the x-ray detector 100 in the second diagnosis room ROOM #2 is not usable, the other medical apparatus 403 may bring the x-ray detector 100 of the x-ray imaging apparatus 1 to the second diagnosis room ROOM #2 and may temporarily use it.

As shown in FIG. 16, when the workstation 200 in the first diagnosis room ROOM #1 is wirelessly connected with the four x-ray detectors 100, the user may mount the x-ray detector 100 mounted on the table mounting portion 310 of the first diagnosis room ROOM #1 on the first portable mounting portion 330*a* of the second diagnosis room ROOM #2. In this case, the x-ray detector 100 mounted on the first portable mounting portion 330*a* of the second diagnosis room ROOM #2 may be connected with the other medical apparatus 403 through wireless communication. Also, the x-ray detector 100 mounted on the first portable mounting portion 330*a* of the second diagnosis room ROOM #2 may maintain wired communication with the x-ray imaging apparatus 1 or may be disconnected from the x-ray imaging apparatus 1. Also, the other medical apparatus 403 and the x-ray imaging apparatus 1 may be connected to each other through the network 400. Also, the other medical apparatus 403 may set the x-ray detector 100 mounted on the first portable mounting portion 330*a* based on the previously stored detector pairing data 271 or the setting information of the x-ray imaging apparatus 1.

As described above, the configuration of the x-ray imaging apparatus 1 and the connection between the x-ray detector 100 and the workstation 200 have been described. Hereinafter, referring to FIGS. 17 to 65, a graphic user interface for setting the x-ray detector 100 will be described.

Figure 17:
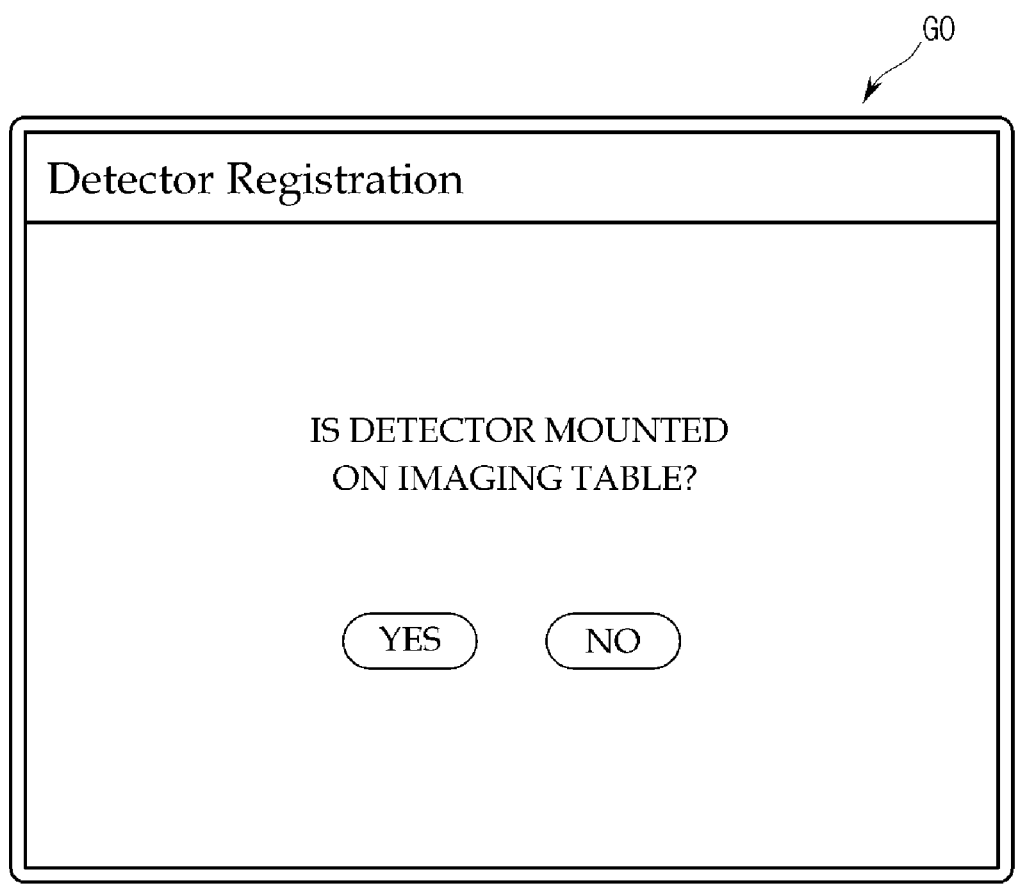
FIG. 17 is a view of a graphic user interface displayed when a mounting portion senses mounting of a detector according to an exemplary embodiment.

FIG. 17 is a view of a graphic user interface displayed when the mounting portion 300 senses mounting of the x-ray detector 100 according to an exemplary embodiment.

The mounting sensor 340 senses whether the x-ray detector 100 is mounted on a mounting portion 300, and the workstation 200 checks whether the mounted x-ray detector 100 is previously mounted before and setting information exists.

When the x-ray detector 100 is mounted on the mounting portion 300 and the mounted x-ray detector 100 is not the x-ray detector 100 previously mounted on the same mounting portion 300, the workstation 200 determines that new setting is used. Accordingly, the workstation 200 may display a screen which indicates that setting of the x-ray detector 100 newly mounted on the mounting portion 300 is used on a user interface to embody a graphic user interface G0.

In detail, as shown in FIG. 17, when the mounting sensor 340 of the table mounting portion 310 checks that the x-ray detector 100 is mounted and there is no setting information corresponding to the x-ray detector 100, the display 212 may display a text "Is a detector mounted on an imaging table?" and selection buttons of "YES" and "NO". When the user would like to set the corresponding x-ray detector 100, the user may push the selection button "YES" through the input interface 211 to operate a graphic user interface for setting the corresponding x-ray detector 100. However, when the user would not like to set the corresponding x-ray detector 100, the user may push the selection button "NO" through the input interface 211 and may not perform the setting of the corresponding x-ray detector 100.

Also, in the x-ray imaging apparatus 1, the mounting sensor 340 may set the x-ray detector 100 without sensing the x-ray detector 100 newly mounted on the mounting portion 300.

Figure 18:
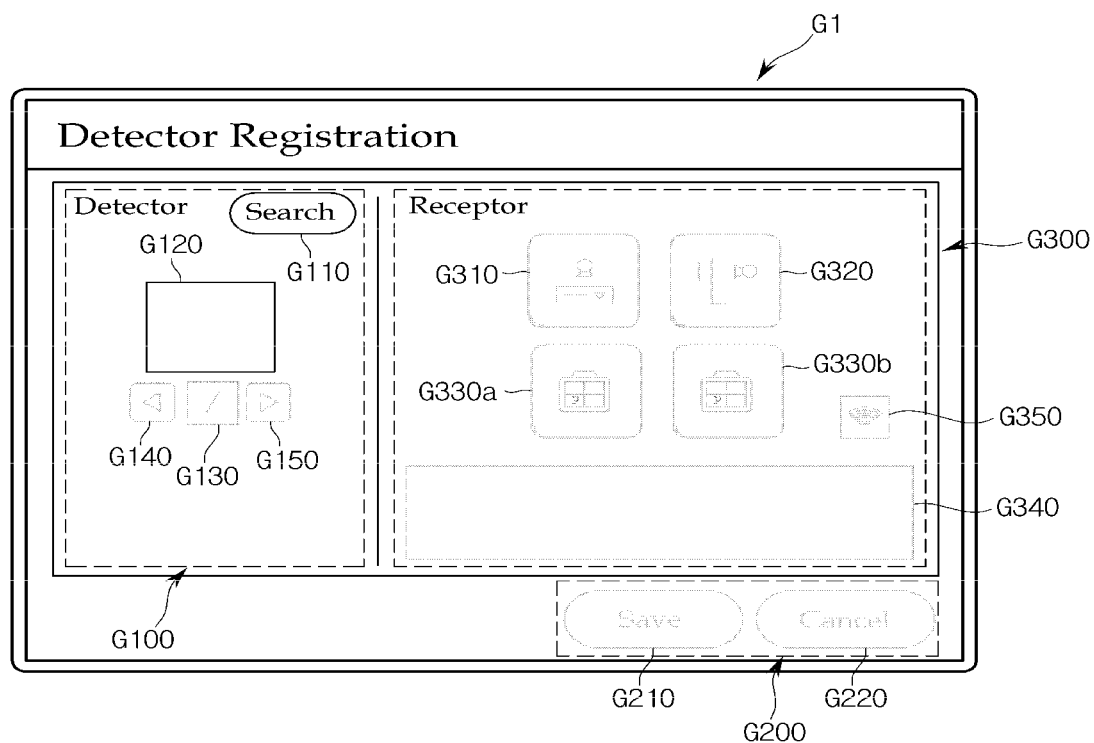
FIG. 18 is a view of a graphic user interface before searching for a detector according to an exemplary embodiment.
Figure 19:
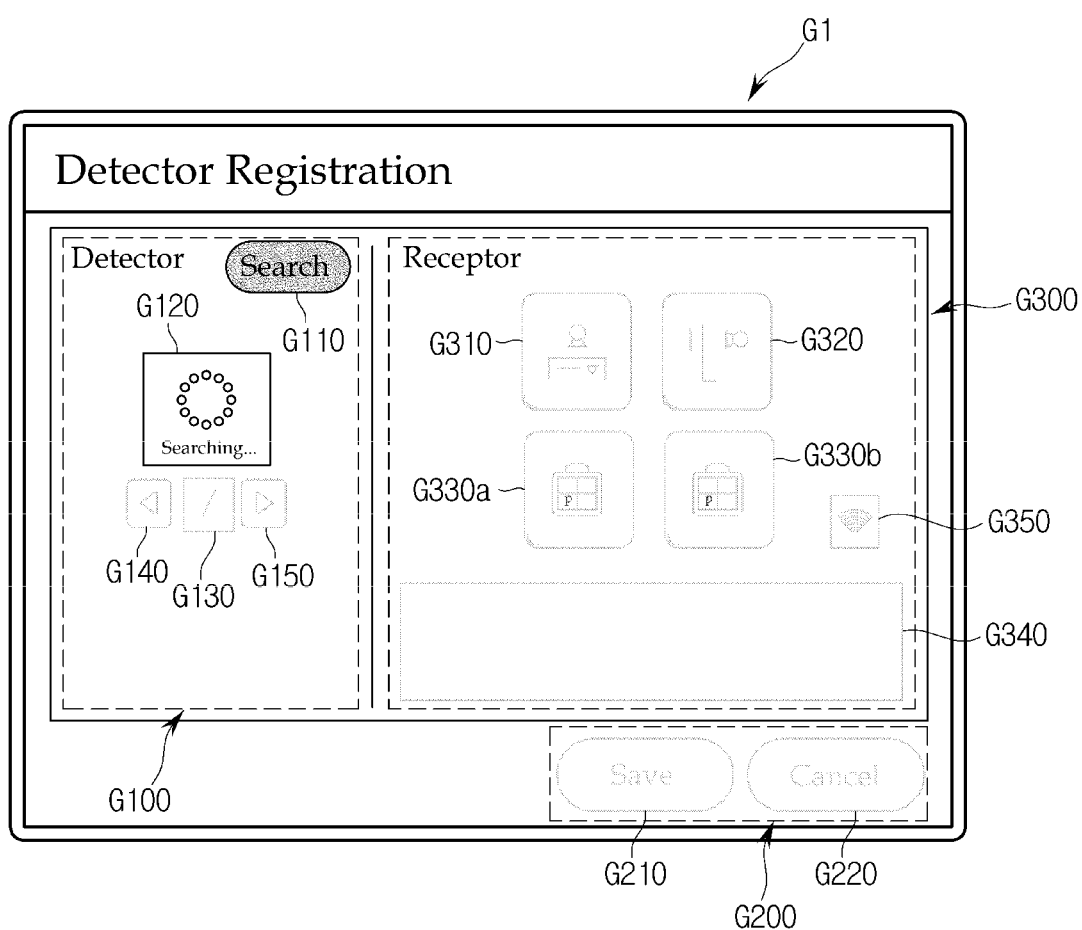
FIG. 19 is a view of a graphic user interface while searching for a detector according to an exemplary embodiment.

FIG. 18 is a view of a graphic user interface before searching for the x-ray detector 100. FIG. 19 is a view of a graphic user interface while searching for the x-ray detector 100.

When detector setting is selected, as shown in FIG. 18, a graphic user interface G1 is executed. The graphic user interface G1 is to set and save an environment for using the x-ray detector 100 and may include a detector screen G100, a mounting portion screen G300, and a setting saving screen G200.

The detector screen G100 is located in the left of the graphic user interface G1. Also, the detector screen G100 may provide a user interface for searching for the x-ray detector 100 presently usable for the x-ray imaging apparatus 1 and selecting the searched x-ray detector 100. Also, the detector screen G100 may include a search button G110 which gives a command for searching for the x-ray detector 100 usable for the x-ray imaging apparatus 1 on a right top end, a selected detector environment screen G120 which displays a type or size of the selected x-ray detector 100, a detector sequence screen G130 which displays a sequence of the presently selected x-ray detector 100 among a plurality of searched x-ray detectors 100, a previous ranking selection button G140 for selecting the x-ray detector 100 at a previous ranking among the plurality of searched x-ray detectors 100, and a next ranking selection button G150 for selecting the x-ray detector 100 at a next ranking among the plurality of searched x-ray detectors 100.

The mounting portion screen G300 is located in the right of the graphic user interface G1. Also, the mounting portion screen G300 may provide a user interface for displaying the mounting portion 300 on which the selected x-ray detector 100 is mountable and selecting the mounting portion 300 to mount. In detail, the mounting portion screen G300 may display the mountable mounting portion 300 based on a size of the selected x-ray detector 100 and a size of the mounting portion 300. Also, the mounting portion screen G300 may include a table selection button G310 which selects to allow the selected x-ray detector 100 to be mounted on the table mounting portion 310, a stand selection button G320 which selects to allow the selected x-ray detector 100 to be mounted on the stand mounting portion 320, a first portable selection button G330*a* which selects to allow the selected x-ray detector 100 to be mounted on the first portable mounting portion 330*a*, a second portable selection button G330b which selects to allow the selected x-ray detector 100 to be mounted on the second portable mounting portion 330b, a wireless communication selection button G350 which selects to allow the selected x-ray detector 100 to be connected to the workstation 200 through wireless communication, and an available mounting portion text screen G340 which displays the mounting portion 300 on which the selected x-ray detector 100 is mountable as a text.

Also, the first portable mounting portion 330a corresponding to the first portable selection button G330a and the second portable mounting portion 330b corresponding to the second portable selection button G330b may have the same structure or may have mutually different structures. For example, the first portable mounting portion 330a may have a shape having the handle and the second portable mounting portion 330b may have a shape having the selfie-mount and the selfie-pole.

The setting saving screen G200 is located at a right bottom of the graphic user interface G1. Also, the setting saving screen G200 may provide a user interface for saving and transferring a communication state of the selected x-ray detector 100 and information for setting a type of the mounting portion 300 to mount to the x-ray detector 100. Also, the setting saving screen G200 may include a saving button G210 which saves and transfers setting information on the x-ray detector 100 and the mounting portion 300 to the x-ray detector 100 in the left and a cancel button G220 which cancels the setting on the x-ray detector 100 and the mounting portion 300 in the right.

First, when the detector setting is selected, the graphic user interface G1 is executed and displayed while all buttons and screens are being deactivated except the search button G110 of the detector screen G100, as shown in FIG. 18. Accordingly, the user may search for the x-ray detector 100 presently usable for the x-ray imaging apparatus 1 by selecting the search button G110.

Also, when the search button G110 is selected, the workstation 200 may identify the respective x-ray detectors 100 by comparing the previously stored detector pairing data 271 with the identification information of the x-ray detectors 100 and may search for the usable x-ray detector 100. In the case of performing such a process described above, as shown in FIG. 20, the search button G110 of the detector screen G100 may be displayed while given with a shadow effect which indicates a selected state, and a detector environment screen may display that the x-ray imaging apparatus 1 is presently searching for the usable x-ray detector 100. Also, all the buttons and screens may be deactivated except the search button G110 and the detector environment screen of the detector screen G100.

After that, when the plurality of x-ray detectors 100 usable for the x-ray imaging apparatus 1 are searched, the graphic user interface G1 for selecting one of the searched x-ray detectors 100 and setting the communication state and the type of the mounting portion 300 to mount may be executed.

Figure 20:
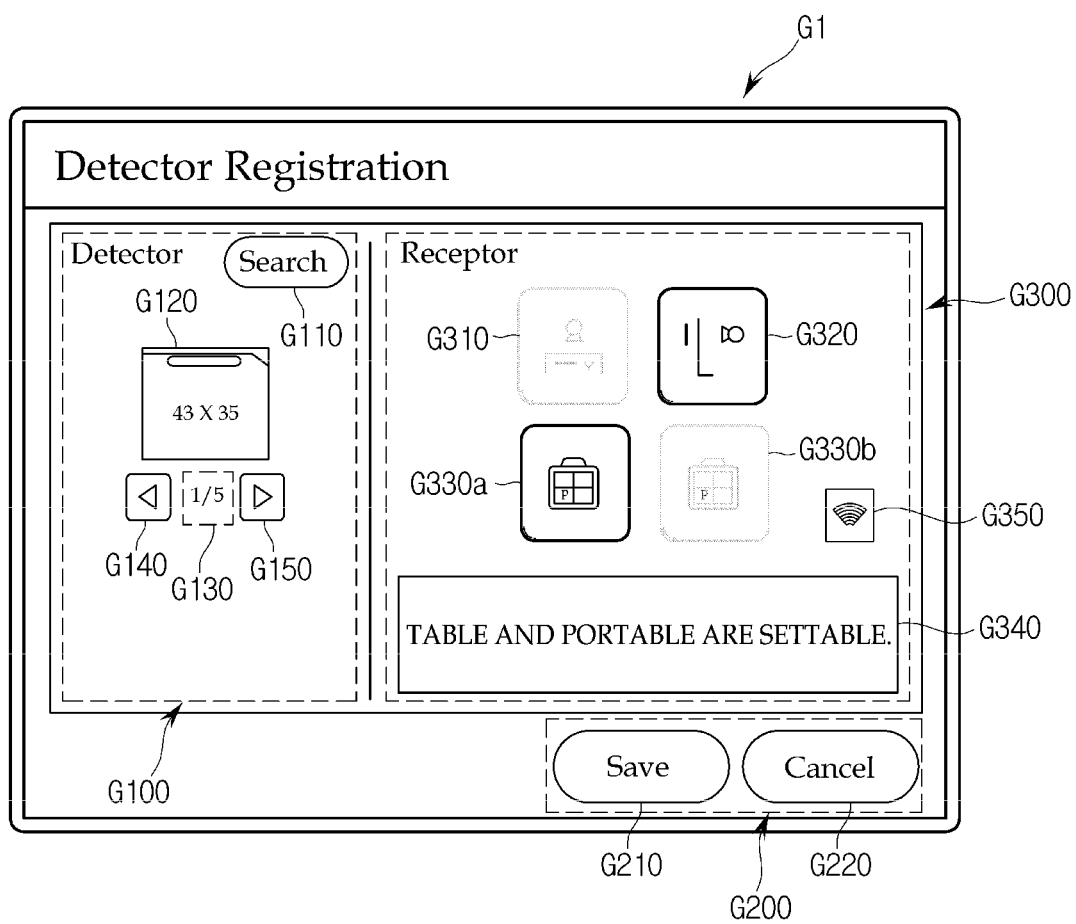
FIG. 20 is a view of a graphic user interface after searching for a detector according to an exemplary embodiment.
Figure 21:
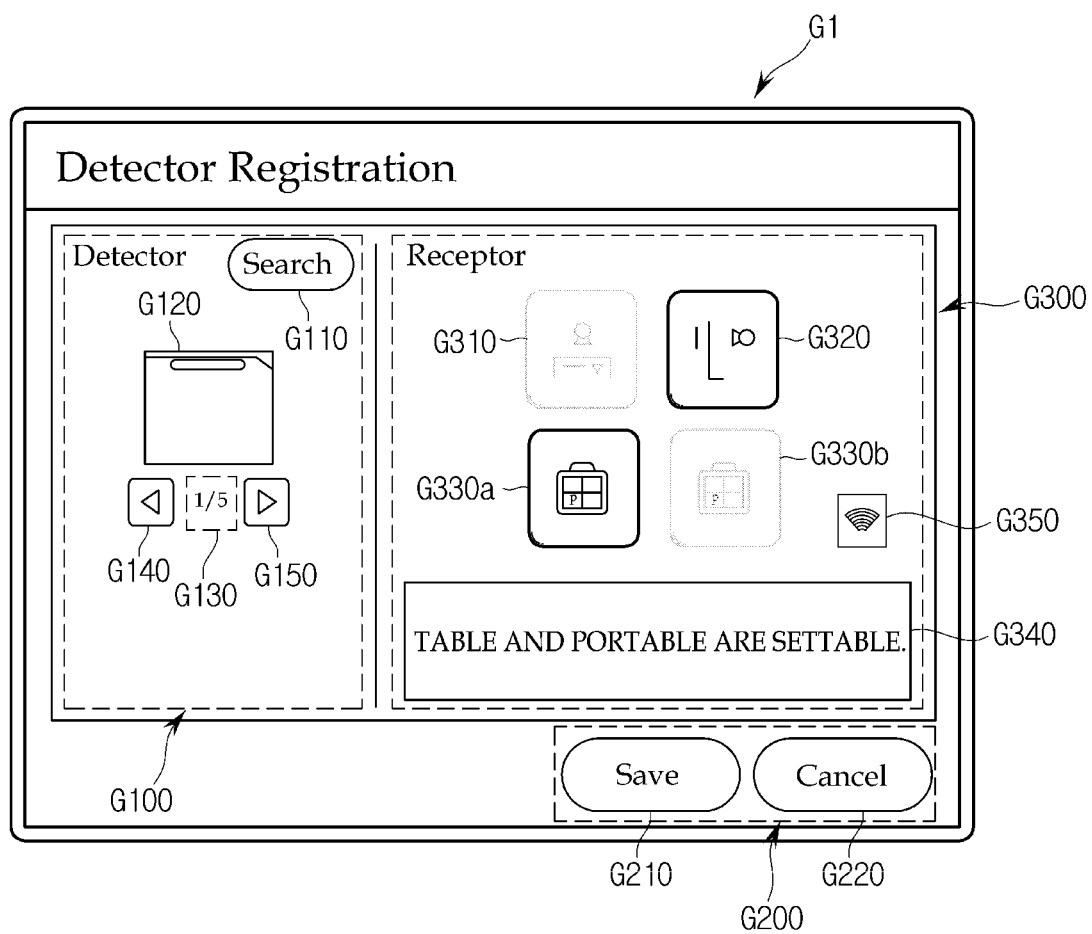
FIG. 21 is a view of a graphic user interface after searching for a detector according to an exemplary embodiment.
Figure 22:
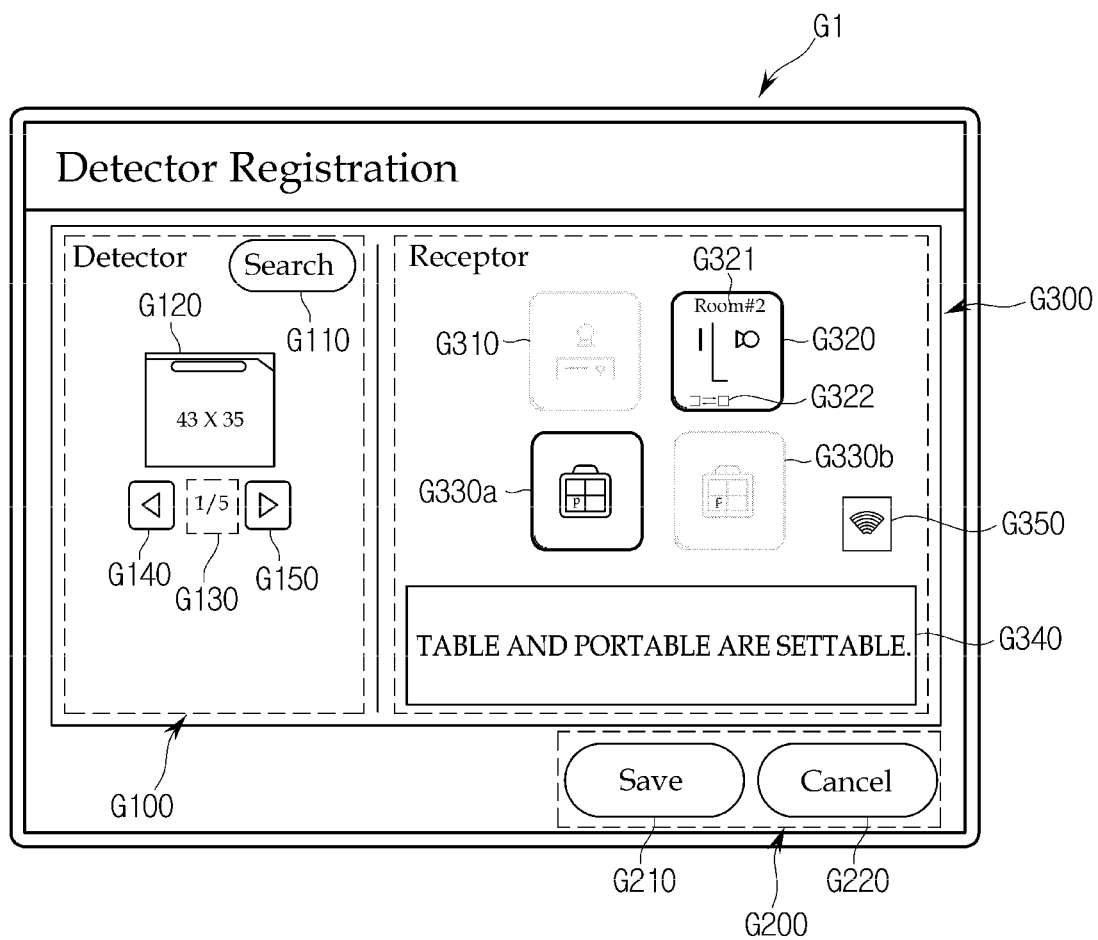
FIG. 22 is a view of a graphic user interface after searching for a detector according to an exemplary embodiment.
Figure 23:
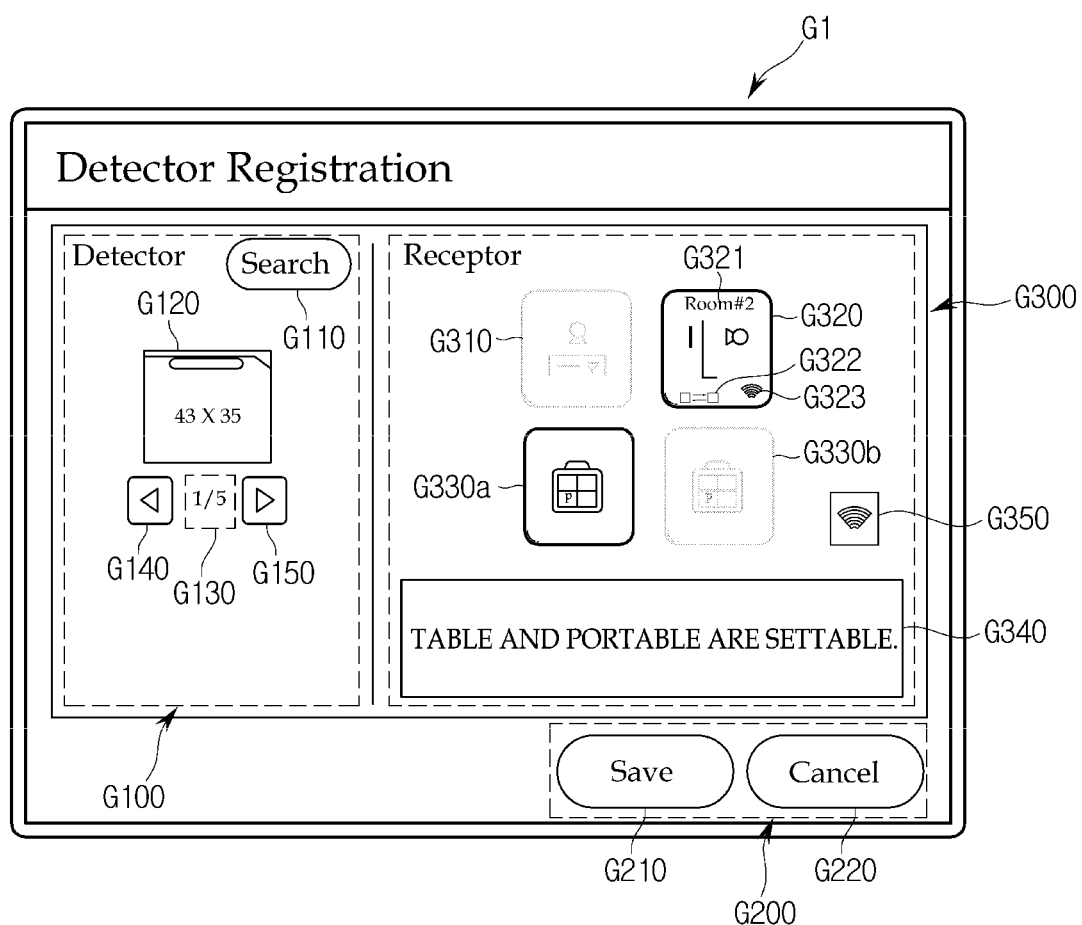
FIG. 23 is a view of a graphic user interface after searching for a detector according to an exemplary embodiment.

FIG. 20 is a view of a graphic user interface after searching for a detector according to an exemplary embodiment. FIG. 21 is a view of a graphic user interface after searching for a detector according to an exemplary embodiment. FIG. 22 is a view of a graphic user interface after searching for a detector according to an exemplary embodiment. FIG. 23 is a view of a graphic user interface after searching for a detector according to an exemplary embodiment.

As shown in FIG. 20, after searching for the x-ray detector 100 usable for the x-ray imaging apparatus 1, the graphic user interface G1 provides an interface for selecting one x-ray detector 100 among the plurality of x-ray detectors 100 and setting the selected x-ray detector 100.

In detail, a shadow of the search button G110 of the detector screen G100 disappears and the search button G110 returns to an activated state. Also, the selected detector environment screen G120 may display the presently selected detector to display that a size of the selected detector is 43×35 cm or may display a distinction sign displayed on the detector display 190 to distinguish the selected detector from other detectors.

Also, the selected detector environment screen G120 may display the size of the presently selected detector using a text shown in FIG. 20 or may adjust and display a size of an icon as shown in FIG. 21. For example, when the size of the detector is 43×35 cm, as shown in FIG. 21, the icon may be shown in a rectangular shape. When the size of the detector is 43×43 cm, the icon may be shown in a square shape. When the size of the detector is 30×25 cm, the icon may be shown in a smaller rectangular shape.

Also, the selected detector sequence screen G130 displays the number of the x-ray detectors 100 usable for the x-ray imaging apparatus 1 and a ranking of the presently selected x-ray detector 100. That is, the selected detector sequence screen G130 may display "1/5" which indicates that the number of the x-ray detectors 100 presently usable for the x-ray imaging apparatus 1 is 5 and the ranking of the presently selected x-ray detector 100 is the first. Also, the previous ranking selection button G140 and the next ranking selection button G150 may be activated to select one of the x-ray detectors 100 presently usable for the x-ray imaging apparatus 1.

Also, only one corresponding to the mounting portion 300 mountable based on the size of the selected x-ray detector 100 among the table selection button G310, the stand selection button G 320, the first portable selection button G330a, and the second portable selection button G330b is activated. For example, when the size of the selected x-ray detector 100 is 43×35 cm and the mounting portion 300 having a size to mount the selected x-ray detector 100 corresponds to the stand mounting portion 320 and the first portable mounting portion 330a, the graphic user interface G1 may deactivate the table selection button G310 and the second portable selection button G330b and may activate the stand selection button G320 and the first portable selection button G330a. That is, the user may select one of the stand selection button G320 and the first portable selection button G330a to determine the mounting portion 300 on which the selected x-ray detector 100 is to be mounted.

Also, when the mounting portion 300 corresponding to the activated stand selection button G320 and the first portable selection button G330a is located in the second diagnosis room ROOM #2 located adjacently to the first diagnosis room ROOM #1, a diagnosis room screen and a swap screen G322 may be displayed on a mounting portion selection button. For example, as shown in FIG. 22, when the stand mounting portion 320 is located in the second diagnosis room ROOM #2, a diagnosis room screen "ROOM #2" may be displayed above the stand selection button G320 and the swap screen G322 may be displayed below the stand selection button G320.

The wireless communication selection button G350 in the mounting portion screen G300 is a user interface for selecting the mounting portion 300 on which the selected x-ray detector 100 is to be mounted and then selecting a method of communicating between the selected x-ray detector 100 and the workstation 200. For example, when it is set to mount the selected x-ray detector 100 on the stand mounting portion 320 and the selected x-ray detector 100 is able to wirelessly communicate, the wireless communication selection button G350 is activated. Then, when to wirelessly connect the selected x-ray detector 100, the user may select the wireless communication selection button G350.

Also, it is possible to display a communication method of exchanging information with the workstation 200 in a case in which the x-ray detector 100 is mounted on the mounting portion 300 corresponding to the activated stand selection button G320 and the first portable selection button G330a. For example, as shown in FIG. 23, when the user would like to mount the selected x-ray detector 100 on the stand mounting portion 320 and to wirelessly connect the selected x-ray detector 100 with the workstation 200, a wireless communication screen G323 may be displayed below the stand selection button G320.

The available mounting portion text screen G340 in the mounting portion screen G300 may display the mounting portion 300 on which the selected x-ray detector 100 is mountable as a text. For example, when the size of the selected x-ray detector 100 is 43×35 cm and the mounting portion 300 having a size to mount the selected x-ray detector 100 corresponds to the stand mounting portion 320 and the first portable mounting portion 330a, the graphic user interface G1 may display a text "Table and Portable are settable." on the available mounting portion text screen G340.

To use conditions such as the communication state and the type of the mounting portion 300 set with respect to the selected x-ray detector 100, the user may give a command of saving and transferring set information to the x-ray detector 100 by selecting the saving button G210 on the setting saving screen G200. On the contrary, when the user would not like to use the conditions such as the communication state and the type of the mounting portion 300 set with respect to the selected x-ray detector 100, the user may give a command of cancellation by selecting the cancel button G220 on the setting saving screen G200.

Also, the graphic user interface G1 may display a state of the x-ray detector 100 presently selected by the command of the user. Hereinafter, it will be described with reference to FIGS. 24 to 28.

Figure 24:
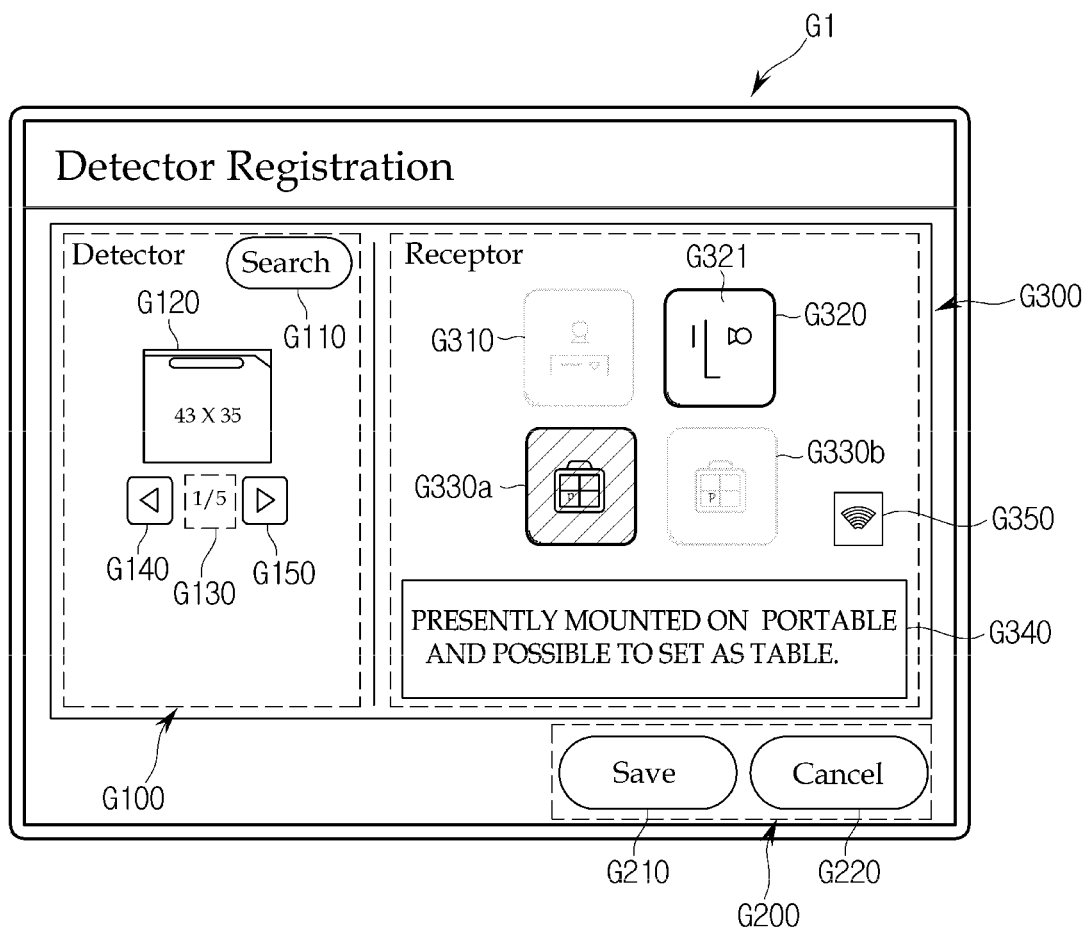
FIG. 24 is a view of a graphic user interface after searching for a detector according to an exemplary embodiment.

FIG. 24 is a view of a graphic user interface after searching for a detector according to an exemplary embodiment.

First, the graphic user interface G1 may display the type of the mounting portion 300 on which the x-ray detector 100 presently selected by the user is presently mounted.

For example, when the user selects a first x-ray detector having a size of 43×35 cm, the graphic user interface G1 may display the first portable selection button G330a in bold type to be distinguished from the stand selection button G320 to display the mounting portion 300 on which the first x-ray detector presently selected is mounted. Also, the graphic user interface G1 may display a text "Presently mounted on Portable and possible to set Table." on the available mounting portion text screen G340.

Figure 25:
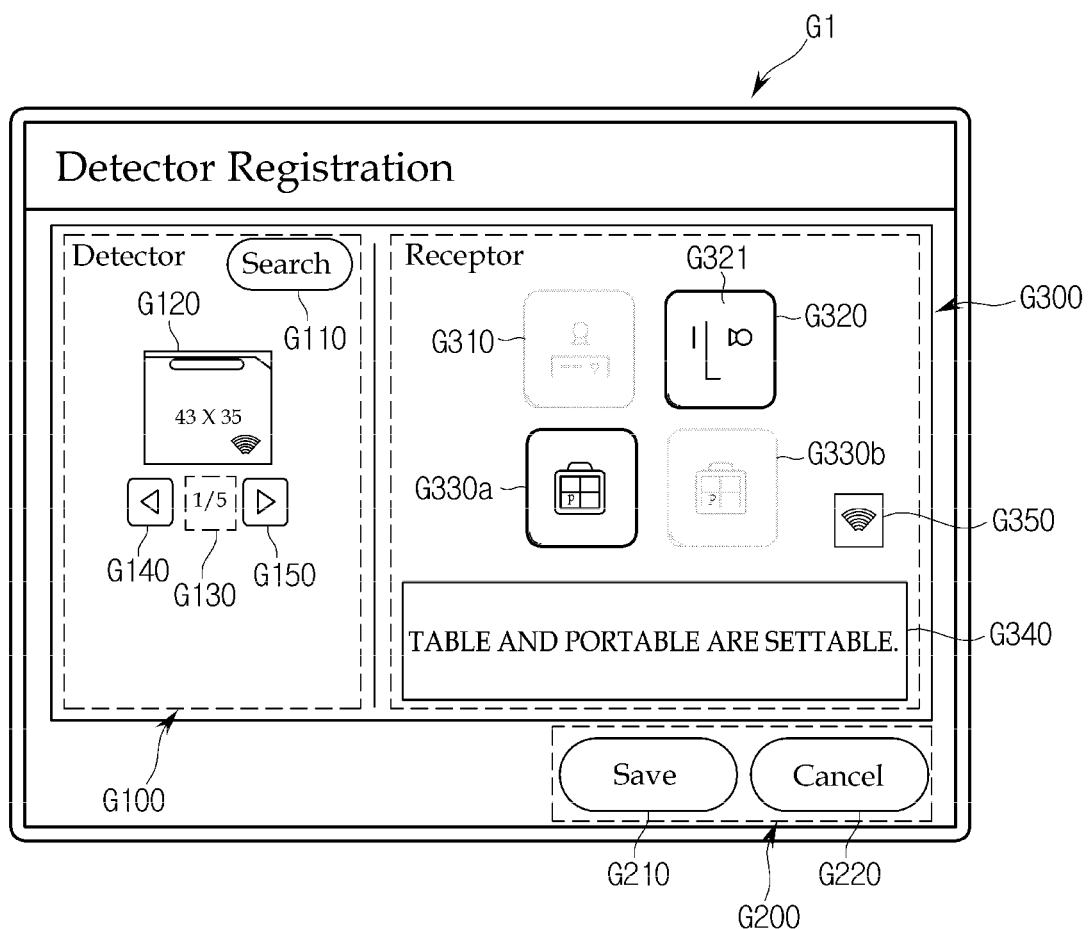
FIG. 25 is a view of a graphic user interface after searching for a detector according to an exemplary embodiment.

FIG. 25 is a view of a graphic user interface after searching for a detector according to an exemplary embodiment.

Also, the graphic user interface G1 may display a present communication state of the x-ray detector 100 presently selected by the user.

For example, when the user selects the first x-ray detector having the size of 43×35 cm, the graphic user interface G1 may display an icon which indicates wireless communication at a right bottom of the selected detector environment screen G120 as shown in FIG. 24 to display a method of communicating between the presently selected first x-ray detector and the communication interface 260 of the workstation 200.

Figure 26:
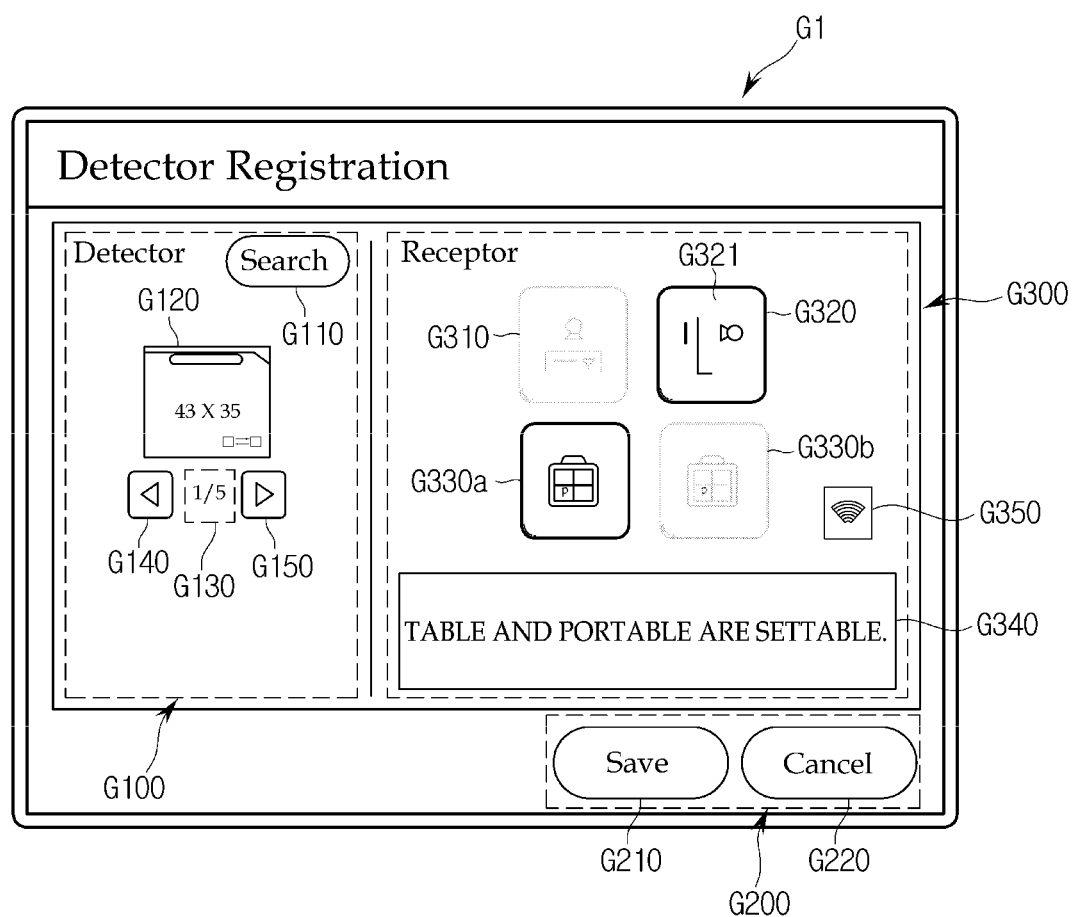
FIG. 26 is a view of a graphic user interface after searching for a detector according to an exemplary embodiment.

FIG. 26 is a view of a graphic user interface after searching for a detector according to an exemplary embodiment.

Also, the graphic user interface G1 may display whether the x-ray detector 100 presently selected by the user is swappable.

For example, when the user selects the first x-ray detector having the size of 43×35 cm, the graphic user interface G1 may display an icon which indicates a swap at the right bottom of the selected detector environment screen G120 as shown in FIG. 25 to display a method of communicating between the presently selected first x-ray detector and the communication interface 260 of the workstation 200.

Figure 27:
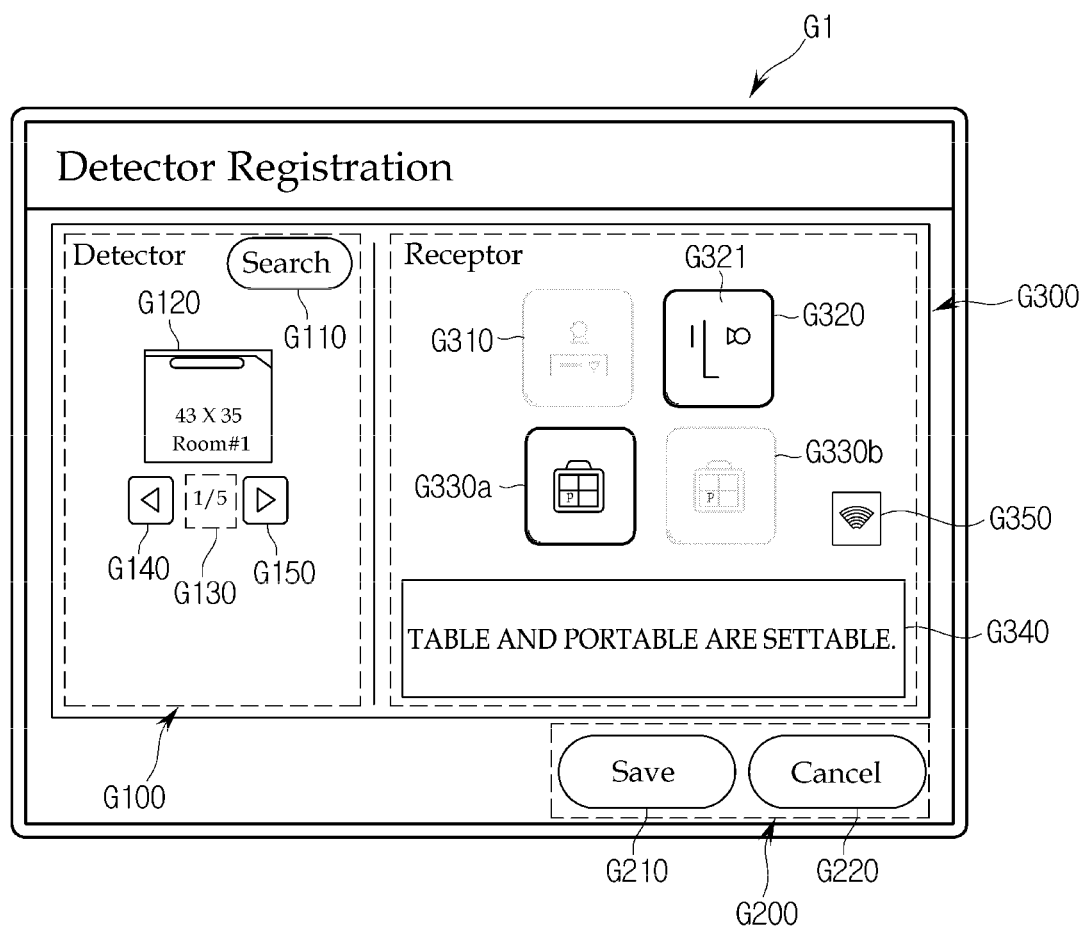
FIG. 27 is a view of a graphic user interface after searching for a detector according to an exemplary embodiment.

FIG. 27 is a view of a graphic user interface after searching for a detector according to an exemplary embodiment.

Also, the graphic user interface G1 may display a diagnosis room in which the x-ray detector 100 presently selected by the user is located.

For example, when the user selects the first x-ray detector having the size of 43×35 cm, the graphic user interface G1 may display a text "Room #1" which indicates the first diagnosis room at the right bottom of the selected detector environment screen G120 as shown in FIG. 26 to display a method of communicating between the presently selected first x-ray detector and the communication interface 260 of the workstation 200.

Figure 28:
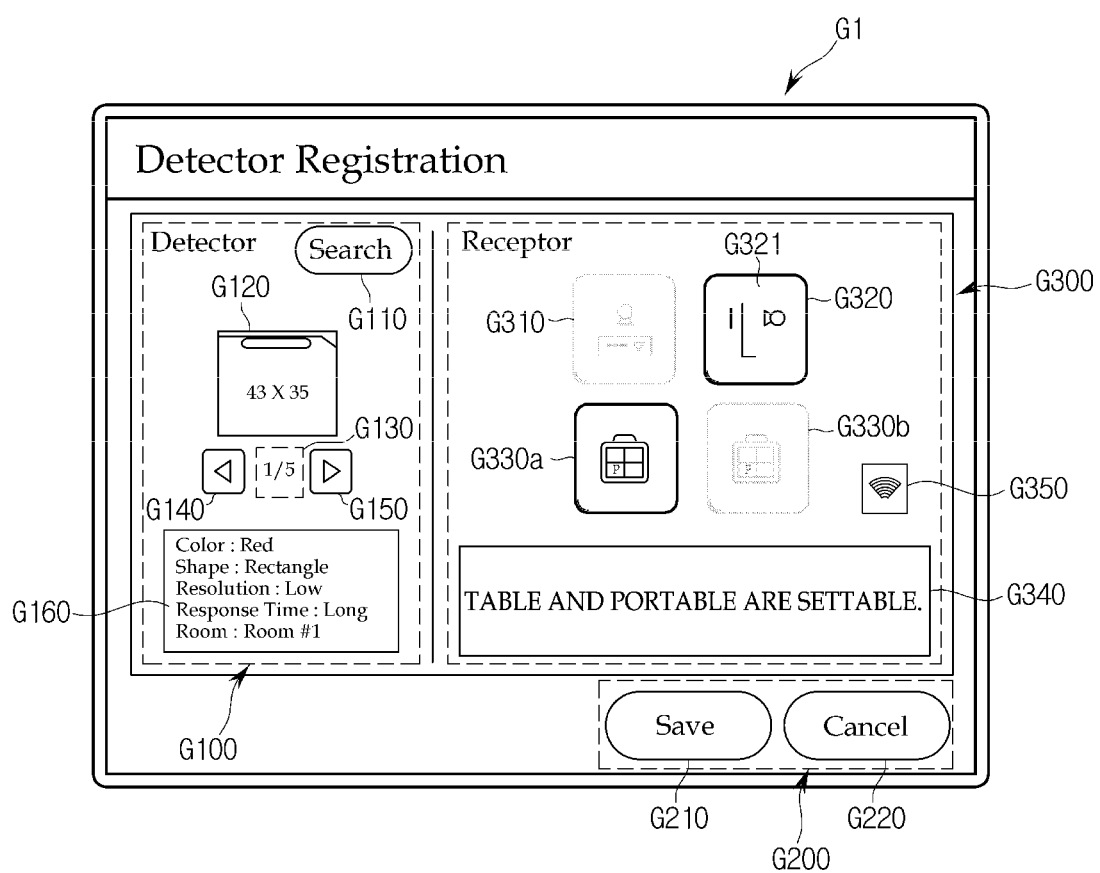
FIG. 28 is a view of a graphic user interface after searching for a detector according to an exemplary embodiment.

FIG. 28 is a view of a graphic user interface after searching for a detector according to an exemplary embodiment.

Also, the graphic user interface G1 may display state information of the x-ray detector 100 presently selected by the user.

For example, when the user selects the first x-ray detector having the size of 43×35 cm, the graphic user interface G1 may display a color, a shape, resolution, a response time, and a diagnosis room of the first x-ray detector presently selected. The detector screen G100 of the graphic user interface G1 may include a detector other state screen G160. That is, the detector other state screen G160 may display that the selected first x-ray detector has a red color, a rectangular shape, low resolution, and a slow response time and is located in the first diagnosis room. In detail, the detector other state screen G160 may display a text "Color: Red" to allow the user to recognize that the detector is red, may display a text "Shape: Rectangle" to allow the user to recognize that the detector has a rectangular shape, and may display a text "Resolution: Low" to allow the user to recognize that the detector has low resolution. Also, the detector other state screen G160 may display a text "Response time: Long" to allow the user to recognize that the response time of the detector is long and may display a text "Room: Room #1" to allow the user to recognize that the detector is located in the first diagnosis room.

Hereinafter, referring to FIGS. 29 to 31, examples of the graphic user interface G1 which displays a mounting portion on which a presently selected detector is mounted will be described.

Figure 29:
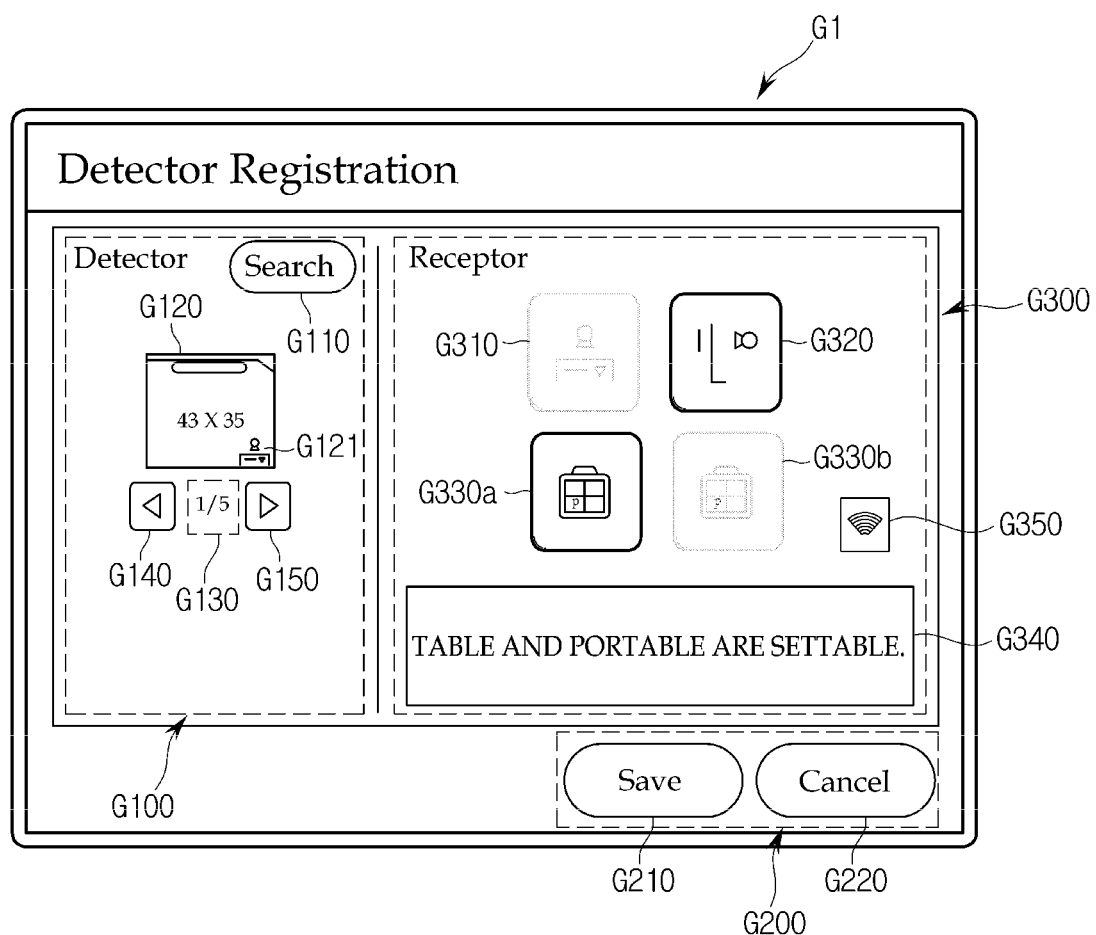
FIG. 29 is a view of a graphic user interface after searching for a detector according to an exemplary embodiment.

FIG. 29 is a view of a graphic user interface after searching for a detector according to an exemplary embodiment. FIG. 30 is a view of a graphic user interface after searching for a detector according to an exemplary embodiment. FIG. 31 is a view of a graphic user interface after searching for a detector according to an exemplary embodiment.

The graphic user interface G1 may display a mounting portion on which a selected detector is presently mounted.

In detail, as shown in FIG. 29, the selected detector environment screen G120 may include a present mounting portion icon G121 on which the detector is presently mounted. The present mounting portion icon G121 may display an icon which indicates a mounting portion on which a presently selected detector is mounted at a bottom of the selected detector environment screen G120. For example, as shown in FIG. 29, it may be displayed as an icon which indicates an imaging stand that the presently selected detector is mounted on the imaging stand.

Figure 30:
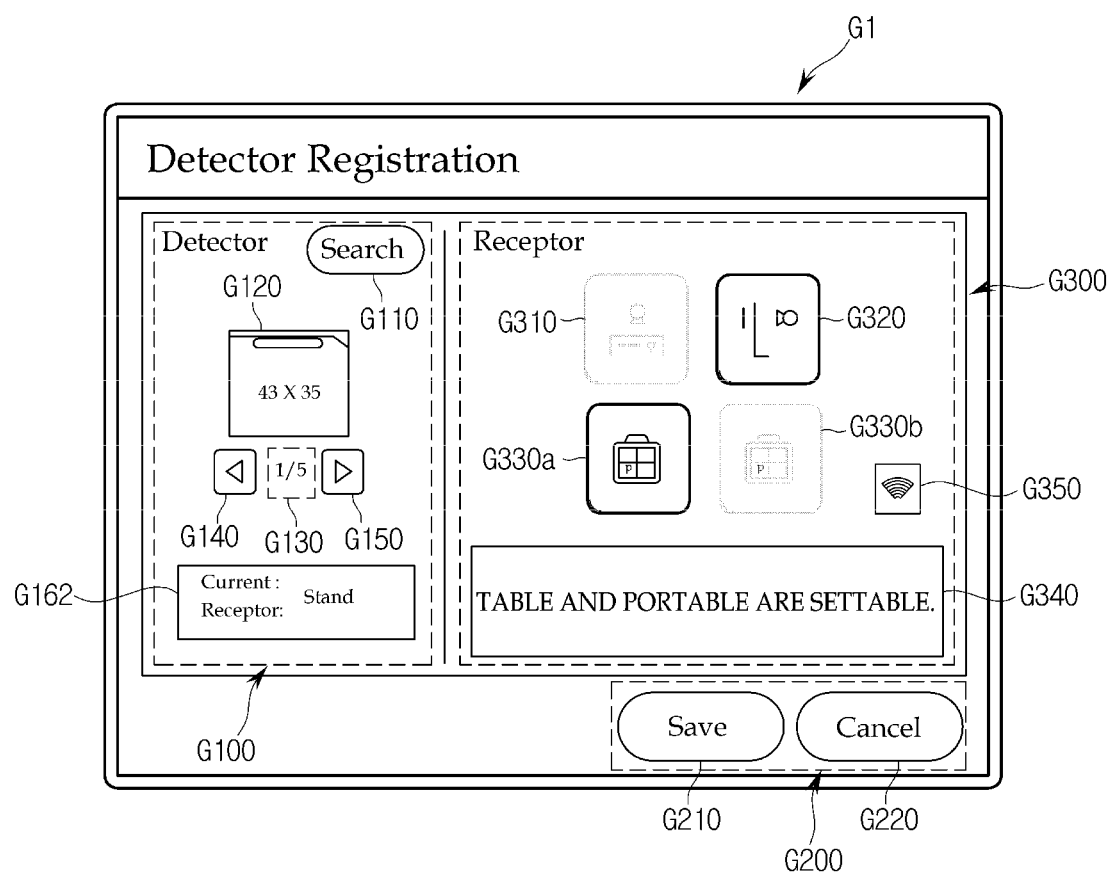
FIG. 30 is a view of a graphic user interface after searching for a detector according to an exemplary embodiment.

Also, as shown in FIG. 30, the graphic user interface G1 may display the mounting portion on which the selected detector is mounted through a present mounting portion text G162 on the detector other state screen G160. For example, when the mounting portion on which the selected detector is mounted is the imaging stand as shown in FIG. 30, the present mounting portion text G162 may be displayed as "Current Receptor: Stand".

Figure 31:
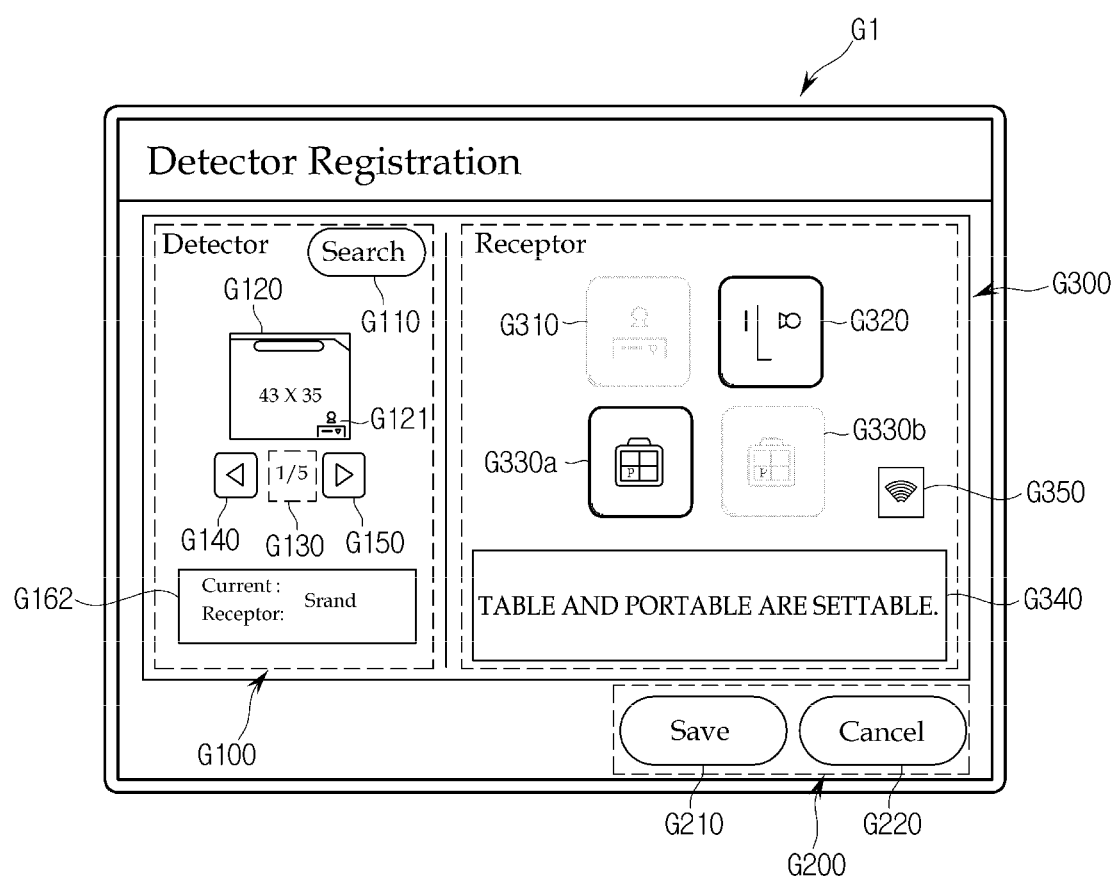
FIG. 31 is a view of a graphic user interface after searching for a detector according to an exemplary embodiment.

Also, as shown in FIG. 31, the graphic user interface G1 may include the present mounting portion icon G121 and the present mounting portion text G162 to display the mounting portion on which the selected detector is presently mounted as an icon and a text.

Hereinafter, referring to FIGS. 32 and 33, examples of the graphic user interface G1 which displays a modality that can be used by a presently selected detector will be described.

Figure 32:
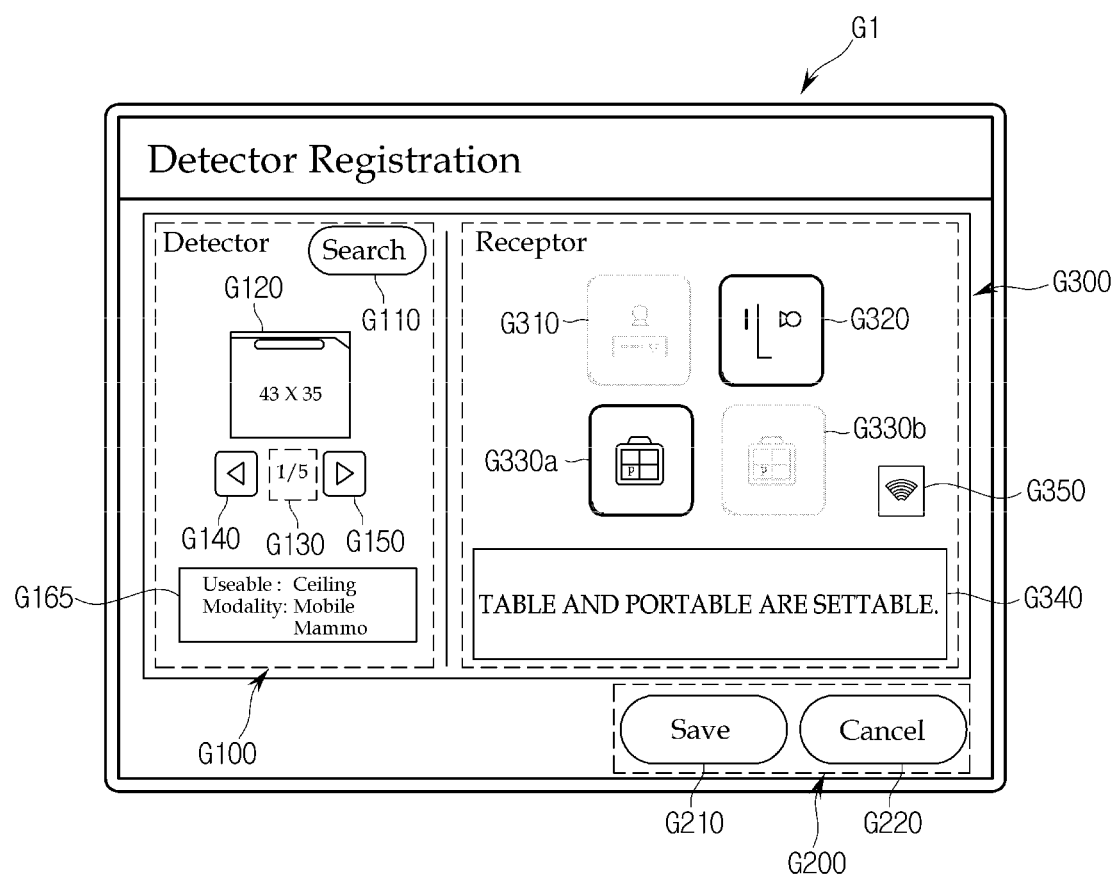
FIG. 32 is a view of a graphic user interface after searching for a detector according to an exemplary embodiment.

FIG. 32 is a view of a graphic user interface after searching for a detector according to an exemplary embodiment. FIG. 33 is a view of a graphic user interface after searching for a detector according to an exemplary embodiment.

The graphic user interface G1 may display a modality that can be used by a selected detector.

Figure 33:
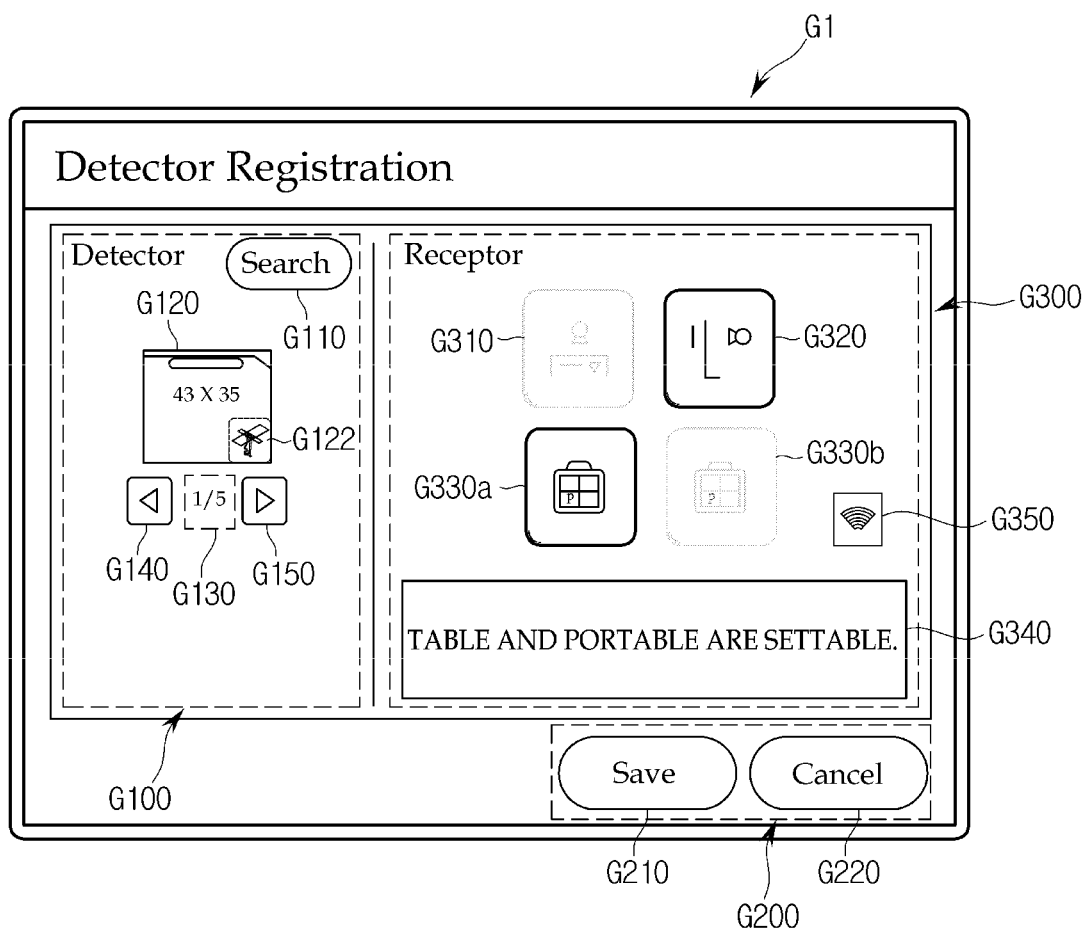
FIG. 33 is a view of a graphic user interface after searching for a detector according to an exemplary embodiment.

In detail, as shown in FIG. 33, the selected detector environment screen G120 may include a usable modality icon G122. The usable modality icon G122 may display a modality that can be used by a presently selected detector as an icon at the bottom of the selected detector environment screen G120. For example, as shown in FIG. 32, a modality that can be used by a selected detector may be displayed as an icon which indicates a ceiling type.

Also, as shown in FIG. 32, the graphic user interface G1 may display the modality that can be used by the selected detector through a usable modality text G165 on the detector other state screen G160. For example, when the modality that can be used by the selected detector is the ceiling type, a mobile type, and a mammography type, the usable modality text G165 may display a text "Usable Modality: Ceiling, Mobile, Mammo".

As described above, the examples of the graphic user interface G1 which classifies and selects the plurality of searched x-ray detectors 100 depending on sizes thereof have been described. Hereinafter, referring to FIGS. 34 to 38, examples of the graphic user interface G1 which classifies and selects the plurality of searched x-ray detectors depending on other factors except size will be described.

Figure 34:
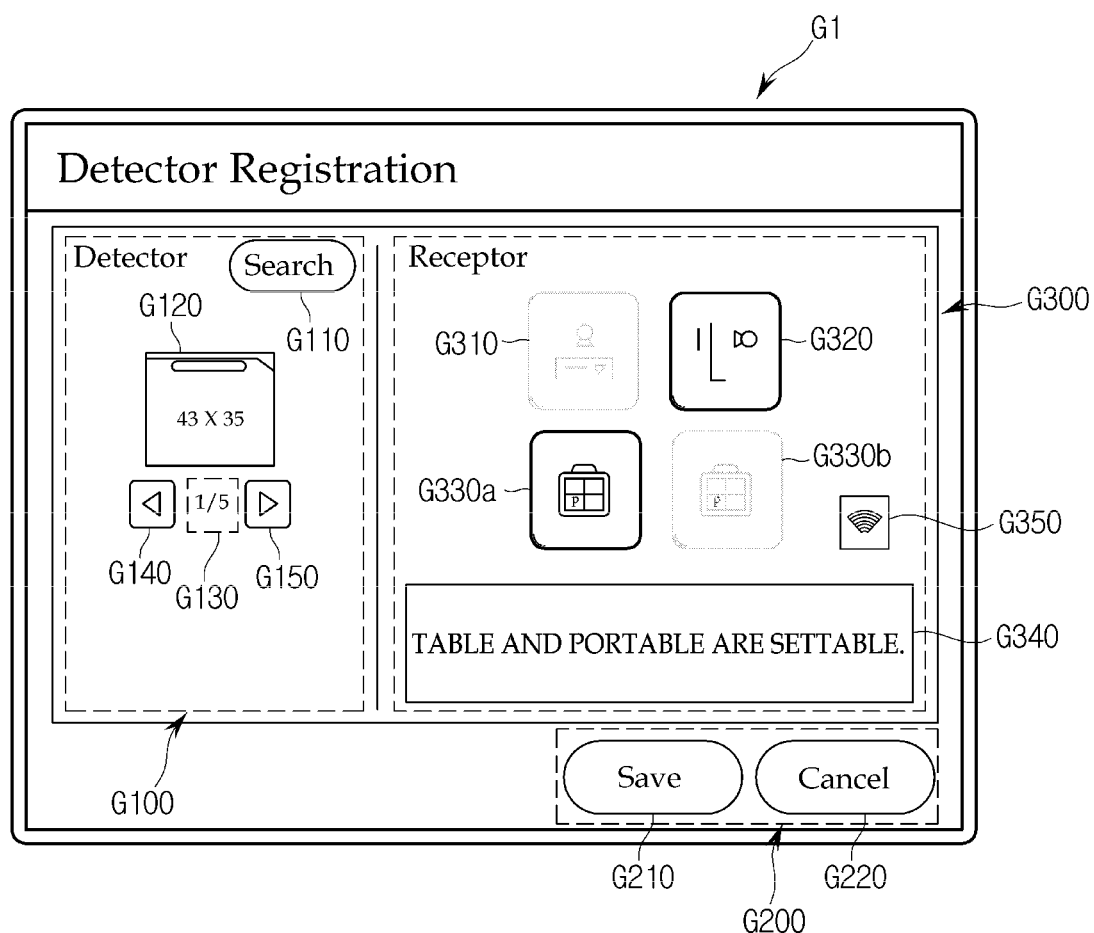
FIG. 34 is a view of a graphic user interface after searching for a detector according to an exemplary embodiment.

FIG. 34 is a view of a graphic user interface after searching for a detector according to an exemplary embodiment.

Also, the graphic user interface G1 may classify the plurality of searched x-ray detectors 100 according to a color and may display a color of the x-ray detector 100 presently selected.

For example, when the user selects the first x-ray detector having the size of 43×35 cm, the graphic user interface G1 may display a text "Green" which indicates green in a middle of a selected detector environment screen G120a as shown in FIG. 34 to display that the first x-ray detector presently selected is green.

Figure 35:
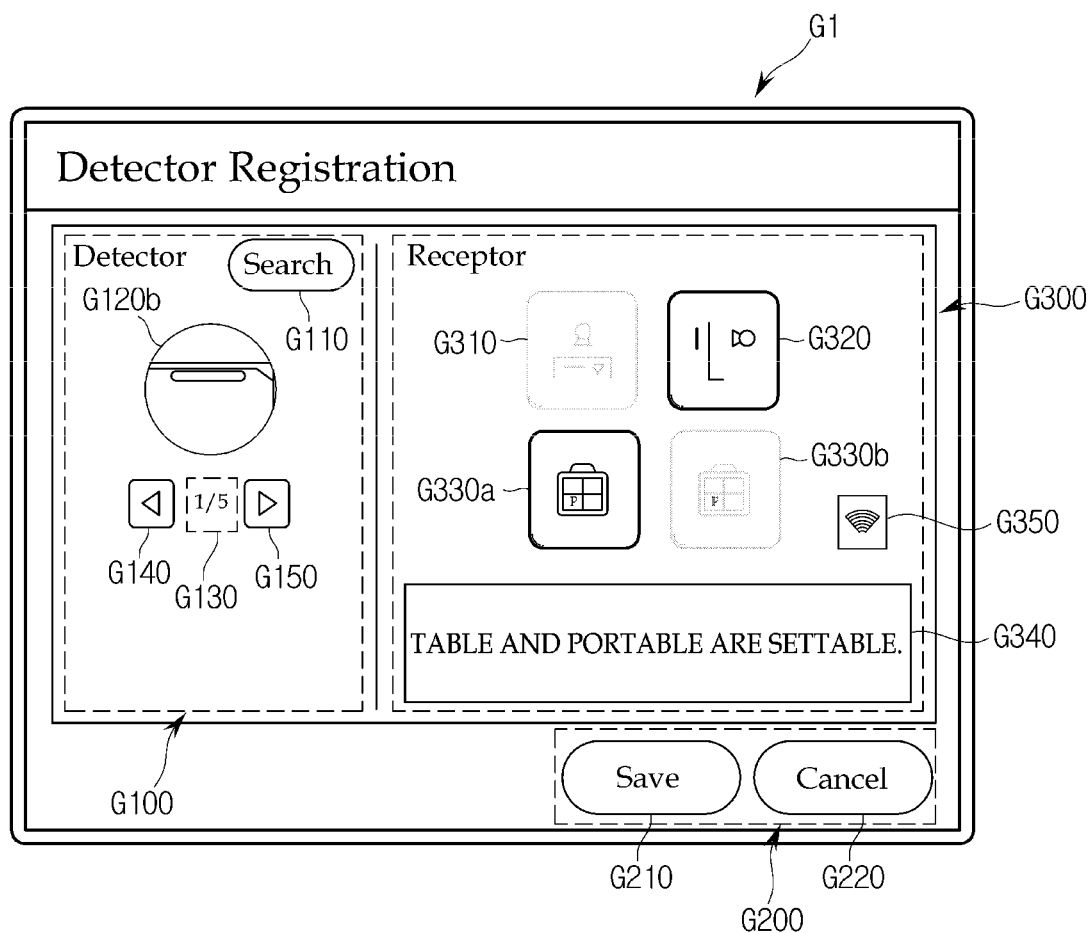
FIG. 35 is a view of a graphic user interface after searching for a detector according to an exemplary embodiment.

FIG. 35 is a view of a graphic user interface after searching for a detector according to an exemplary embodiment.

Also, the graphic user interface G1 may classify the plurality of searched x-ray detectors 100 according to shapes thereof and may display a shape of the x-ray detector 100 presently selected.

For example, when the user selects the first x-ray detector having the size of 43×35 cm, the graphic user interface G1 may display a selected detector environment screen G120b as a circle as shown in FIG. 35 to display that the first x-ray detector presently selected has a circular shape.

Figure 36:
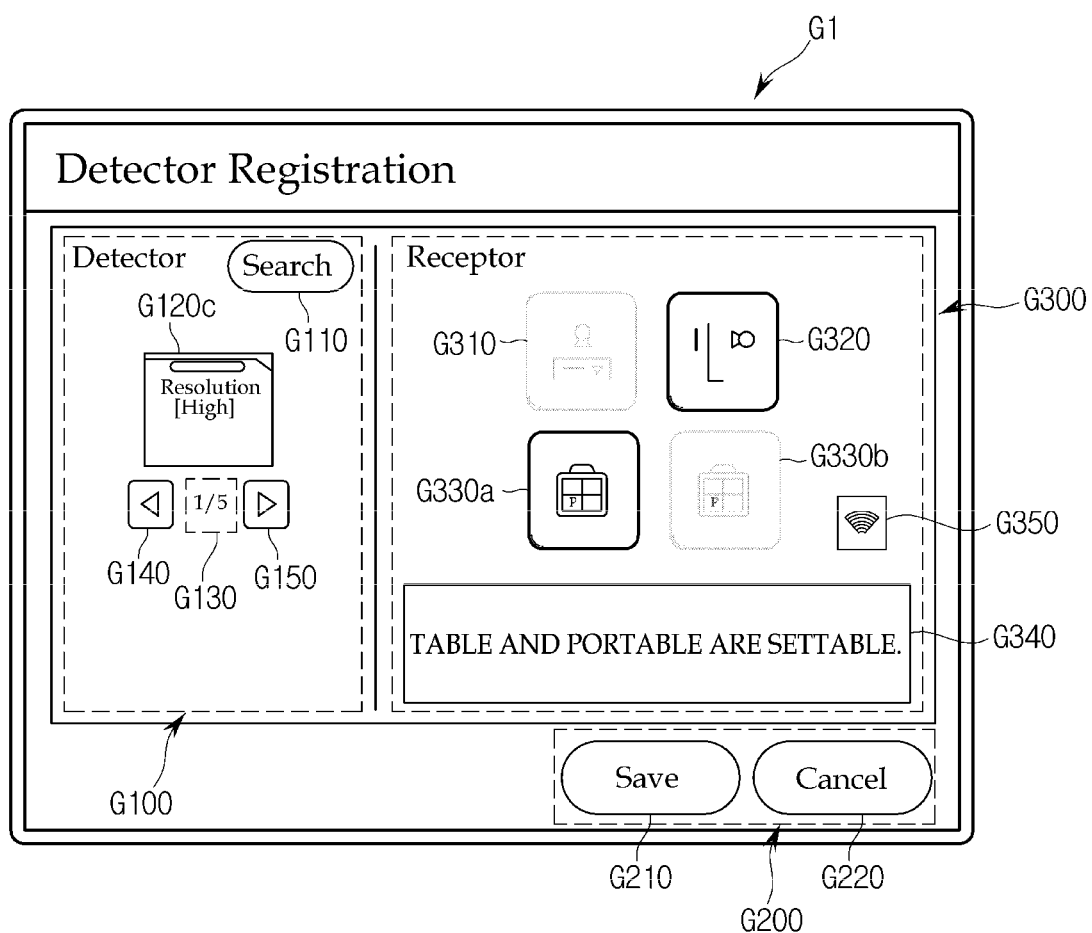
FIG. 36 is a view of a graphic user interface after searching for a detector according to an exemplary embodiment.

FIG. 36 is a view of a graphic user interface after searching for a detector according to an exemplary embodiment.

Also, the graphic user interface G1 may classify the plurality of searched x-ray detectors 100 according to resolution thereof and may display the resolution of the x-ray detector 100 presently selected.

For example, when the user selects the first x-ray detector having the size of 43×35 cm, the graphic user interface G1 may display a text "Resolution [High]" which indicates high resolution in a middle of a selected detector environment screen G120c as shown in FIG. 36 to display that the first x-ray detector presently selected has high resolution.

Figure 37:
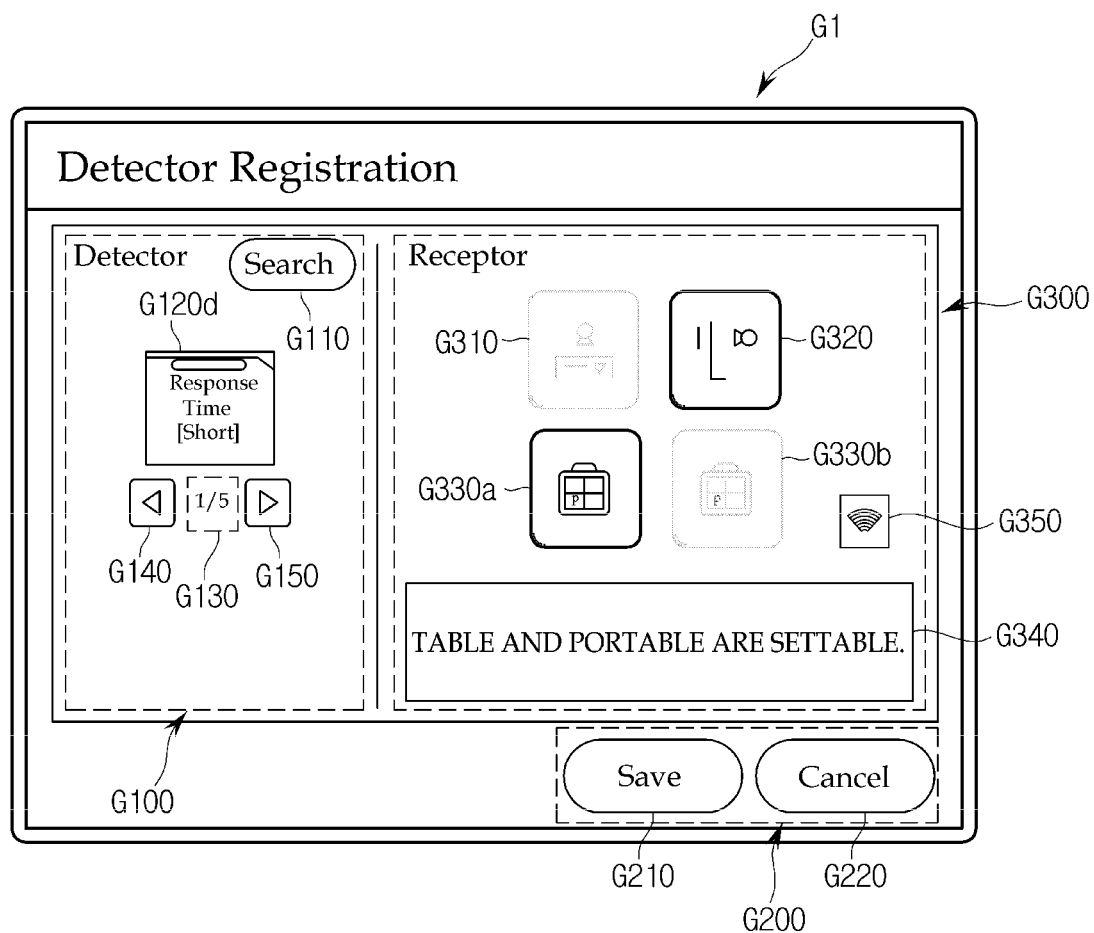
FIG. 37 is a view of a graphic user interface after searching for a detector according to an exemplary embodiment.

FIG. 37 is a view of a graphic user interface after searching for a detector according to an exemplary embodiment.

Also, the graphic user interface G1 may classify the plurality of searched x-ray detectors 100 according to response times thereof and may display a response time of the x-ray detector 100 presently selected.

For example, when the user selects the first x-ray detector having the size of 43×35 cm, the graphic user interface G1 may display a text "Response time [Short]" which indicates a short response time in a middle of a selected detector environment screen G120d as shown in FIG. 37 to display that the first x-ray detector presently selected has a short response time.

Figure 38:
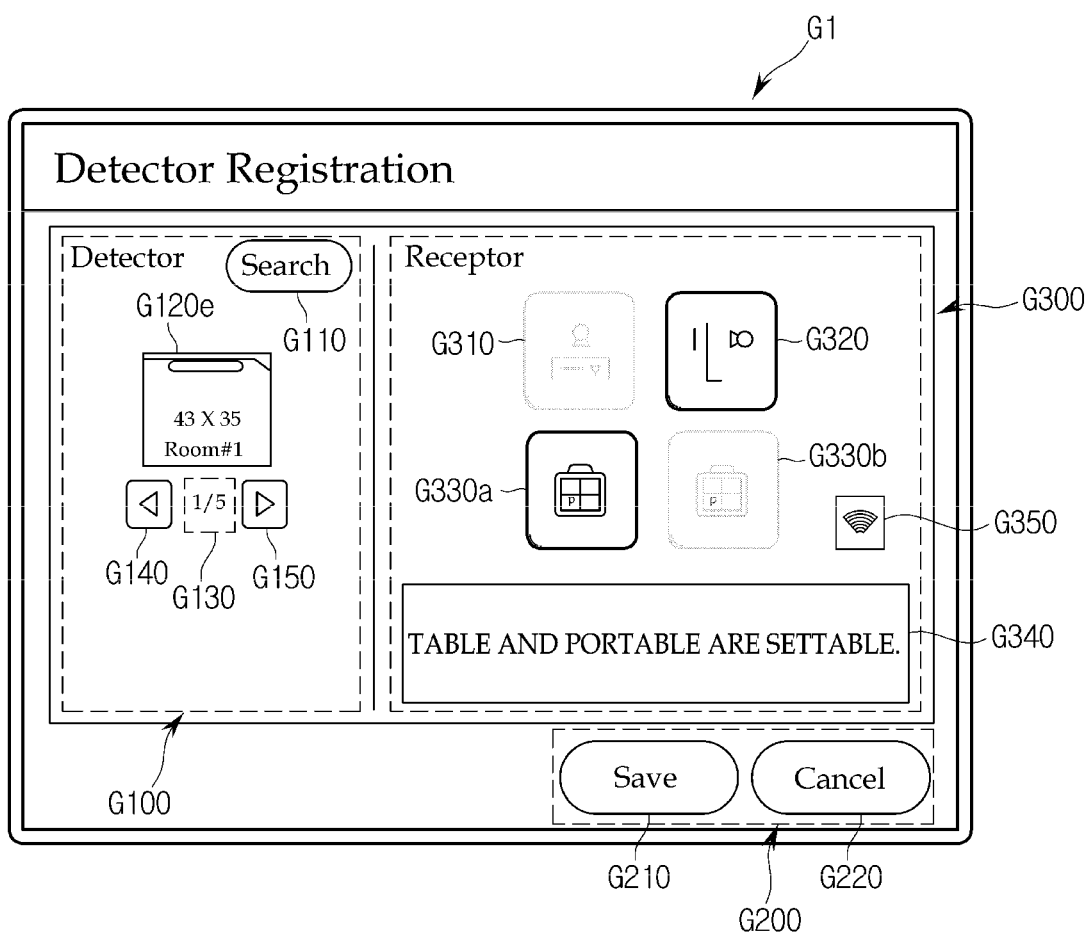
FIG. 38 is a view of a graphic user interface after searching for a detector according to an exemplary embodiment.

FIG. 38 is a view of a graphic user interface after searching for a detector according to an exemplary embodiment.

Also, the graphic user interface G1 may classify the plurality of searched x-ray detectors 100 according to diagnosis rooms and may display a diagnosis room of the x-ray detector 100 presently selected.

For example, when the user selects the first x-ray detector having the size of 43×35 cm, the graphic user interface G1 may display a text "Room #1" which indicates the first diagnosis room at the right bottom of a selected detector environment screen G120e as shown in FIG. 38 to display a method of communicating between the presently selected first x-ray detector and the communication interface 260 of the workstation 200.

Hereinafter, referring to FIGS. 39 to 47, an exemplary embodiment of inputting detector searching conditions and searching for an x-ray detector corresponding to the input searching conditions will be described.

Figure 39:
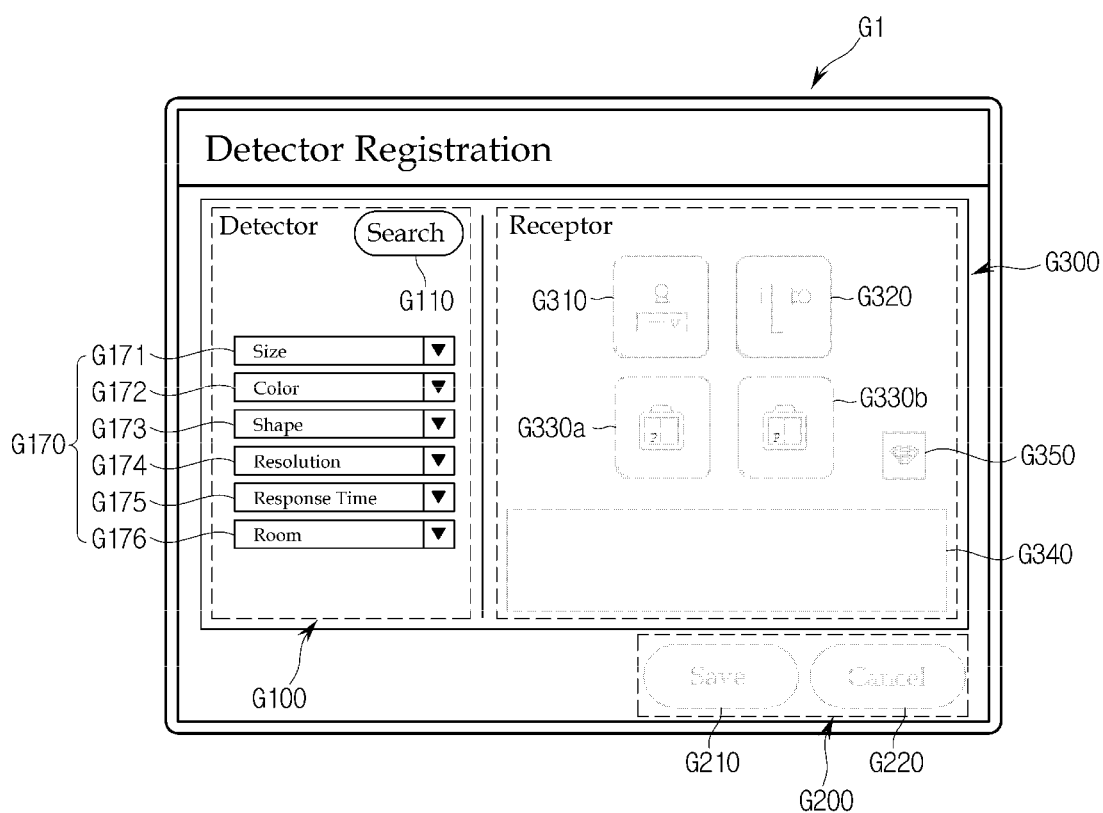
FIG. 39 is a view of a graphic user interface before inputting detector searching conditions according to an exemplary embodiment.

FIG. 39 is a view of a graphic user interface before inputting detector searching conditions.

The user may search all the x-ray detectors 100 presently connectable to the workstation 200 as in the exemplary embodiments described above. However, the user may input searching conditions for the x-ray detector 100 to search for the corresponding x-ray detector 100.

In detail, the graphic user interface G1 may include a searching condition selection list G170 in the detector screen G100. The searching condition selection list G170 may include a size selection item G171, a color selection item G172, a shape selection item G173, a resolution selection item G174, a response time selection item G175, and a diagnosis room selection item G176.

Here, the size selection item G171 is an item to allow the user to select the size of the x-ray detector 100. The graphic user interface G1 may display a selection icon which indicates that options may be unfoldable in the right together with a text "Size". Also, the searching condition may be set for each unit of the size of the x-ray detector 100. For example, the user may set the searching condition of the size of the x-ray detector 100 by the centimeter or by the inch. Also, the color selection item G172 is an item to allow the user to select the color of the x-ray detector 100. The graphic user interface G1 may display a selection icon which indicates that options may be unfoldable in the right together with a text "Color". Also, the shape selection item G173 may be an item to allow the user to select the shape of the x-ray detector 100. The graphic user interface G1 may display a selection icon which indicates that options may be unfoldable in the right together with a text "Shape". Also, the resolution selection item G174 is an item to allow the user to select the resolution of the x-ray detector 100. The graphic user interface G1 may display a selection icon which indicates that options may be unfoldable in the right together with a text "Resolution". Also, the response time selection item G175 is an item to allow the user to select the response time of the x-ray detector 100. The graphic user interface G1 may display a selection icon which indicates that options may be unfoldable in the right together with a text "Response Time". Also, the diagnosis room selection item G176 may be an item to allow the user to select the diagnosis room in which the x-ray detector 100 is presently located. The graphic user interface G1 may display a selection icon which indicates that options may be unfoldable in the right together with a text "Room".

As shown in FIG. 39, the searching condition selection list G170 may be arranged in an order of the size selection item G171, the color selection item G172, the shape selection item G173, the resolution selection item G174, the response time selection item G175, and the diagnosis room selection item G176 from the top but may be arranged in another order.

Figure 40:
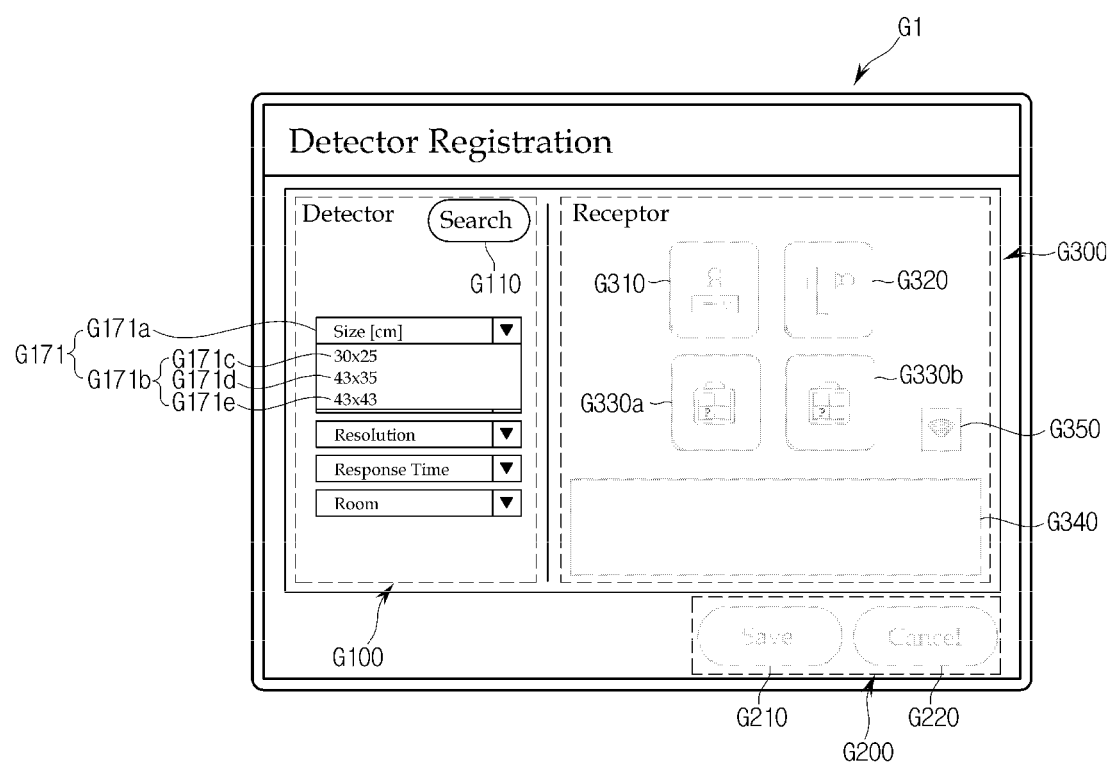
FIG. 40 is a view illustrating an example of the graphic user interface for inputting a searching condition with respect to a size of the detector according to an exemplary embodiment.

FIG. 40 is a view illustrating an example of a graphic user interface for inputting a searching condition with respect to a size of the detector.

The user may input the searching condition with respect to the size of the x-ray detector 100. The user may search while setting the size of the x-ray detector 100 by the centimeter.

In detail, when the user selects the size selection item G171, the graphic user interface G1 may arrange sizes of the x-ray detectors 100 connectable with the body 10. Also, the size selection item G171 may include a size selection title G171a and a size item G171b. The size item G171b may include a first size item G171c, a second size item G171d, and a third size item G171e.

The size selection title G171a may display a searching condition the user would like to set and may display a unit of the searching condition. For example, the size selection title G171a may display an icon which indicates that options are unfolded in the right together with a text "Size [cm]".

The size item G171b may display options of a size condition the user would like to set. For example, when there are three sizes of the x-ray detector 100 connectable with the body 10, the first size item G171c is an item for selecting 30×25 that is one of the sizes of the x-ray detector 100 connectable with the body 10 and may be displayed as a text "30×25". Also, the second size item G171d is an item for selecting 43×35 that is one of the sizes of the x-ray detector 100 connectable with the body 10 and may be displayed as a text "43×35". Also, the third size item G171e is an item for selecting 43×43 that is one of the sizes of the x-ray detector 100 connectable with the body 10 and may be displayed as a text "43×43".

Figure 41:
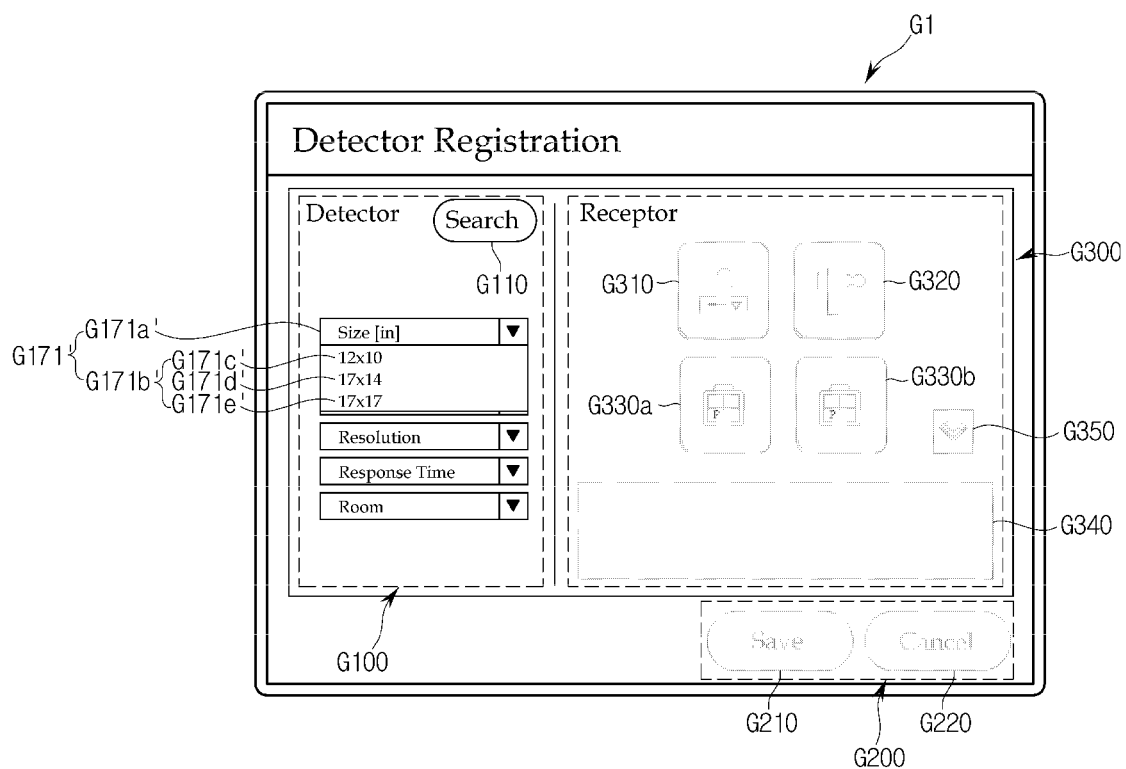
FIG. 41 is a view illustrating another example of the graphic user interface for inputting a searching condition with respect to a size of the detector according to an exemplary embodiment.

FIG. 41 is a view illustrating another example of the graphic user interface for inputting a searching condition with respect to a size of the detector.

The user may input the searching condition with respect to the size of the x-ray detector 100. The user may search while setting the size of the x-ray detector 100 by the inch.

In detail, when the user selects a size selection item G171', the graphic user interface G1 may arrange sizes of the x-ray detectors 100 connectable with the body 10. Also, the size selection item G171' may include a size selection title G171a' and a size item G171b'. The size item G171b' may include a first size item G171c', a second size item G171d', and a third size item G171e'.

The size selection title G171a' may display a searching condition the user would like to set and may display a unit of the searching condition. For example, the size selection title G171a' may display an icon which indicates that options are unfolded in the right together with a text "Size [in]".

The size item G171b' may display options of a size condition the user would like to set. For example, when there are three sizes of the x-ray detector 100 connectable with the body 10, the first size item G171c' is an item for selecting 12×10 that is one of the sizes of the x-ray detector 100 connectable with the body 10 and may be displayed as a text "12×10". Also, the second size item G171d' is an item for selecting 17×14 that is one of the sizes of the x-ray detector 100 connectable with the body 10 and may be displayed as a text "17×14". Also, the third size item G171e' is an item for selecting 17×17 that is one of the sizes of the x-ray detector 100 connectable with the body 10 and may be displayed as a text "17×17".

Figure 42:
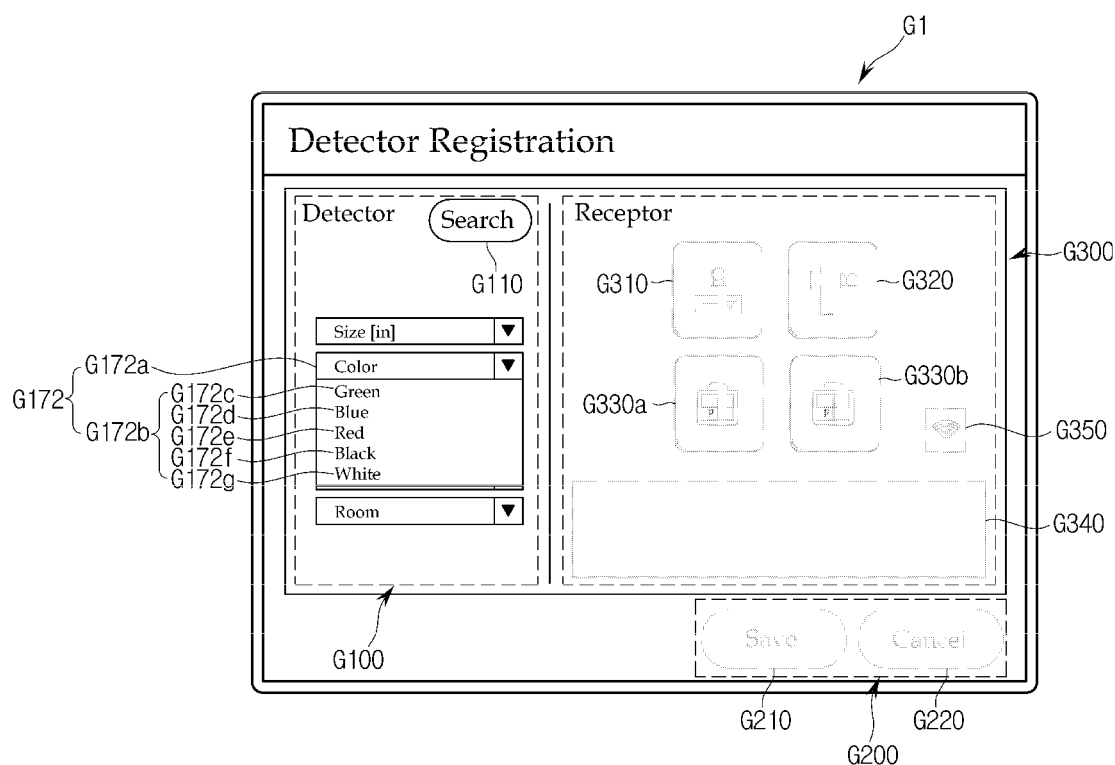
FIG. 42 is a view illustrating the graphic user interface for inputting a searching condition with respect to a color of the detector according to an exemplary embodiment.

FIG. 42 is a view of a graphic user interface for inputting a searching condition with respect to a color of a detector.

The user may input the searching condition with respect to the color of the x-ray detector 100.

In detail, when the user selects the color selection item G172, the graphic user interface G1 may arrange colors of the x-ray detectors 100 connectable with the body 10. Also, the color selection item G172 may include a color selection title G172a and a color item G172b. The color item G172b may include a first color item G172c, a second color item G172d, a third color item G172e, a fourth color item G172f, and a fifth color item G172g.

The color selection title G172a may display the searching condition the user would like to set. For example, the color selection title G172a may display an icon which indicates that options are unfolded in the right together with a text "Color".

The color item G172b may display options of a color condition the user would like to set. For example, when there are five colors of the x-ray detector 100 connectable with the body 10, the first color item G172c is an item for selecting green that is one of the colors of the x-ray detector 100 connectable with the body 10 and may be displayed as a text "Green". Also, the second color item G172d is an item for selecting blue that is one of the colors of the x-ray detector 100 connectable with the body 10 and may be displayed as a text "Blue". Also, the third color item G172e is an item for selecting red that is one of the colors of the x-ray detector 100 connectable with the body 10 and may be displayed as a text "Red". Also, the fourth color item G172f is an item for selecting black that is one of the colors of the x-ray detector 100 connectable with the body 10 and may be displayed as a text "Black". Also, the fifth color item G172g is an item for selecting white that is one of the colors of the x-ray detector 100 connectable with the body 10 and may be displayed as a text "White".

Figure 43:
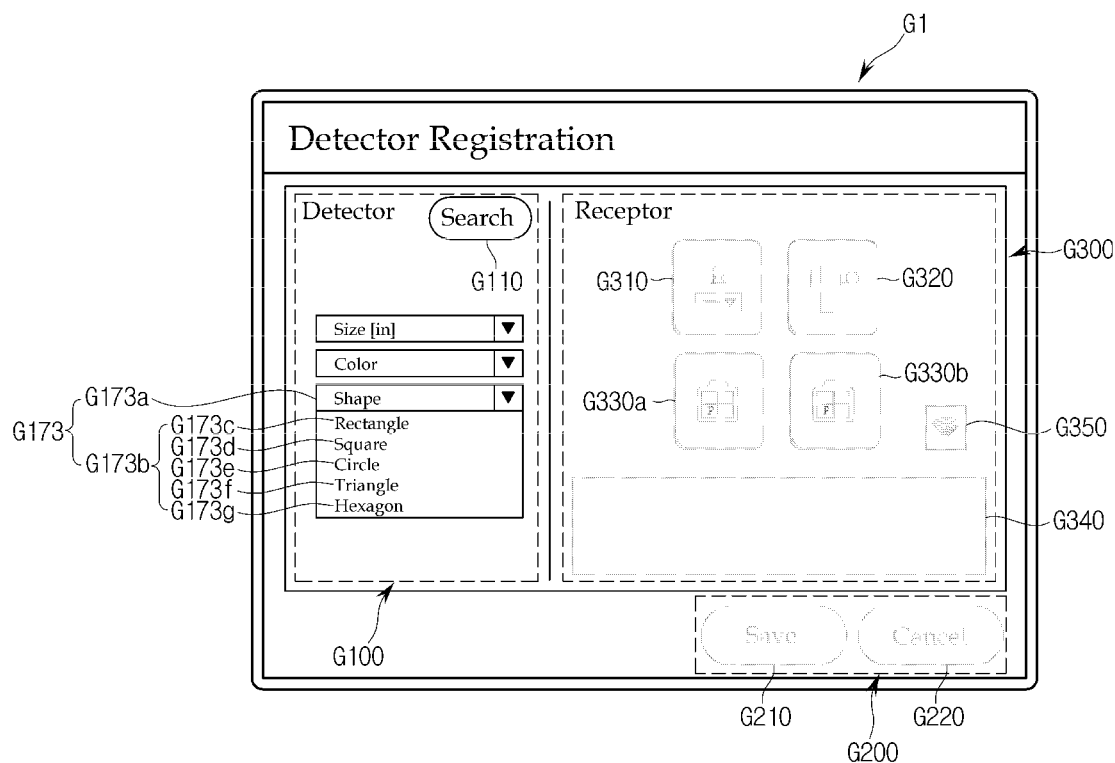
FIG. 43 is a view illustrating the graphic user interface for inputting a searching condition with respect to a shape of the detector according to an exemplary embodiment.

FIG. 43 is a view of a graphic user interface for inputting a searching condition with respect to a shape of a detector.

The user may input the searching condition with respect to the shape of the x-ray detector 100.

In detail, when the user selects the shape selection item G173, the graphic user interface G1 may arrange shapes of the x-ray detectors 100 connectable with the body 10. Also, the shape selection item G173 may include a shape selection title G173a and a shape item G173b. The shape item G173b may include a first shape item G173c, a second shape item G173d, a third shape item G173e, a fourth shape item G173f, and a fifth shape item G173g.

The shape selection title G173a may display the searching condition the user would like to set. For example, the shape selection title G173a may display an icon which indicates that options are unfolded in the right together with a text "Shape".

The shape item G173b may display options of a shape condition the user would like to set. For example, when there are five shapes of the x-ray detector 100 connectable with the body 10, the first shape item G173c is an item for selecting a rectangle that is one of the shapes of the x-ray detector 100 connectable with the body 10 and may be displayed as a text "Rectangle". Also, the second shape item G173d is an item for selecting a square that is one of the shapes of the x-ray detector 100 connectable with the body 10 and may be displayed as a text "Square". Also, the third shape item G173e is an item for selecting a circle that is one of the shapes of the x-ray detector 100 connectable with the body 10 and may be displayed as a text "Circle". Also, the fourth shape item G173f is an item for selecting a triangle that is one of the shapes of the x-ray detector 100 connectable with the body 10 and may be displayed as a text "Triangle". Also, the fifth shape item G173g is an item for selecting a hexagon that is one of the shapes of the x-ray detector 100 connectable with the body 10 and may be displayed as a text "Hexagon".

Figure 44:
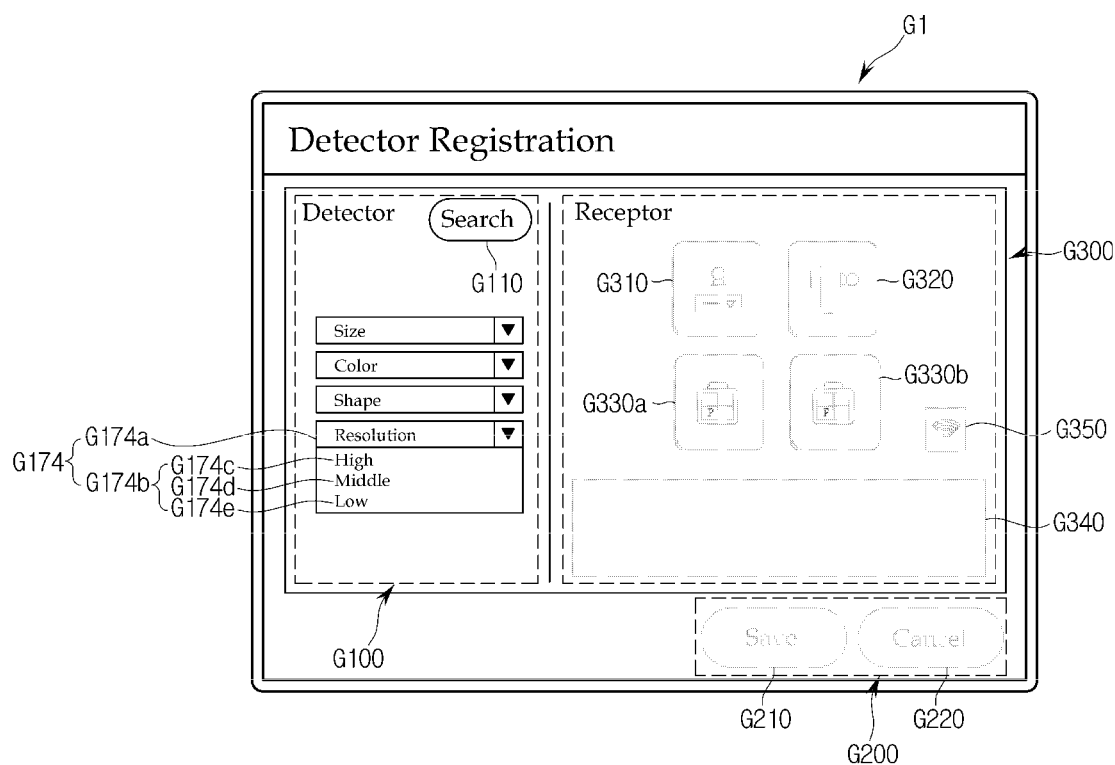
FIG. 44 is a view illustrating the graphic user interface for inputting a searching condition with respect to the resolution of the detector according to an exemplary embodiment.

FIG. 44 is a view of a graphic user interface for inputting a searching condition with respect to resolution of a detector.

The user may input the searching condition with respect to the resolution of the x-ray detector 100.

In detail, when the user selects the resolution selection item G174, the graphic user interface G1 may arrange resolution levels of the x-ray detectors 100 connectable with the body 10. Also, the resolution selection item G174 may include a resolution selection title G174a and a resolution item G174b. The resolution item G174b may include a first resolution item G174c, a second resolution item G174d, and a third resolution item G174e.

The resolution selection title G174a may display the searching condition the user would like to set. For example, the resolution selection title G174a may display an icon which indicates that options are unfolded in the right together with a text "Resolution".

The resolution item G174b may display options of a resolution condition the user would like to set. For example, when there are three resolution levels of the x-ray detector 100 connectable with the body 10, the first resolution item G174c is an item for selecting high resolution that is one of the resolution levels of the x-ray detector 100 connectable with the body 10 and may be displayed as a text "High". Also, the second resolution item G174d is an item for selecting middle resolution that is one of the resolution levels of the x-ray detector 100 connectable with the body 10 and may be displayed as a text "Middle". Also, the third resolution item G174e is an item for selecting low resolution that is one of the resolution levels of the x-ray detector 100 connectable with the body 10 and may be displayed as a text "Low".

Figure 45:
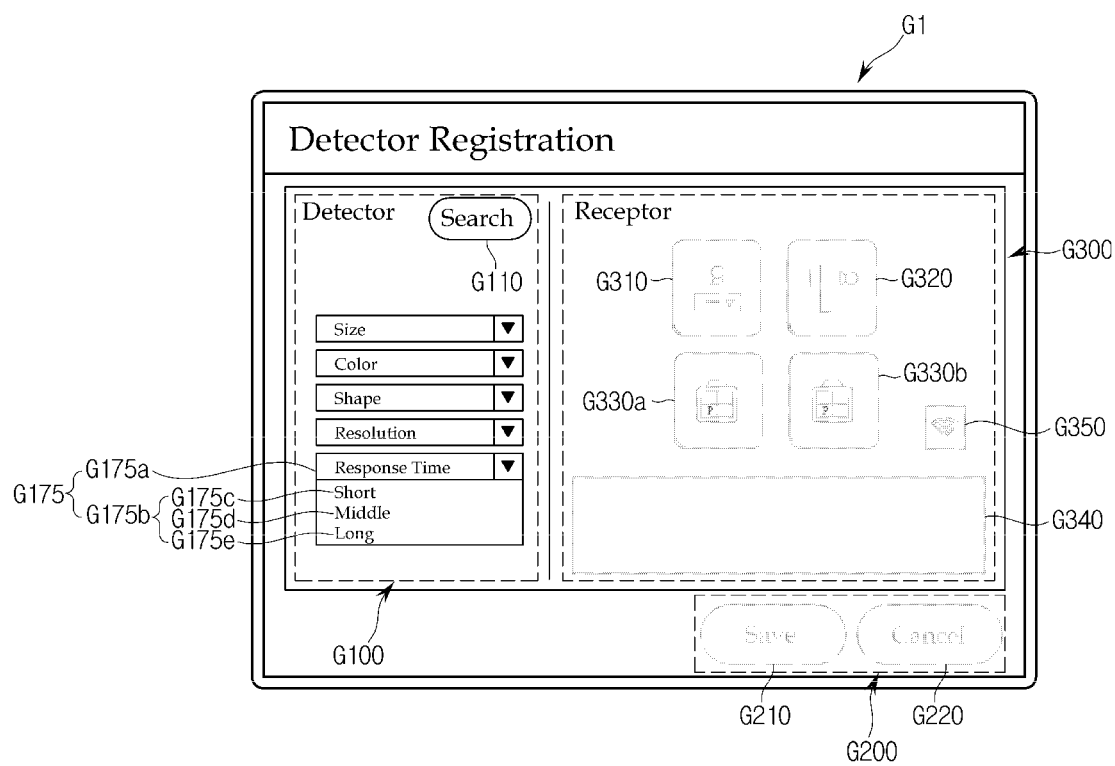
FIG. 45 is a view illustrating the graphic user interface for inputting a searching condition with respect to a response time of the detector according to an exemplary embodiment.

FIG. 45 is a view of a graphic user interface for inputting a searching condition with respect to a response time of a detector.

The user may input the searching condition with respect to the response time of the x-ray detector 100.

In detail, when the user selects the response time selection item G175, the graphic user interface G1 may arrange response times of the x-ray detectors 100 connectable with the body 10. Also, the response time selection item G175 may include a response time selection title G175a and a response time item G175b. The response time item G175b may include a first response time item G175c, a second response time item G175d, and a third response time item G175e.

The response time selection title G175a may display the searching condition the user would like to set. For example, the response time selection title G175a may display an icon which indicates that options are unfolded in the right together with a text "Response Time".

The response time item G175b may display options of a response time condition the user would like to set. For example, when there are three response times of the x-ray detector 100 connectable with the body 10, the first response time item G175c is an item for selecting a high speed that is one of the response times of the x-ray detector 100 connectable with the body 10 and may be displayed as a text "Short". Also, the second response time item G175d is an item for selecting a middle speed that is one of the response times of the x-ray detector 100 connectable with the body 10 and may be displayed as a text "Middle". Also, the third response time item G175e is an item for selecting a low speed that is one of the response times of the x-ray detector 100 connectable with the body 10 and may be displayed as a text "Long".

Figure 46:
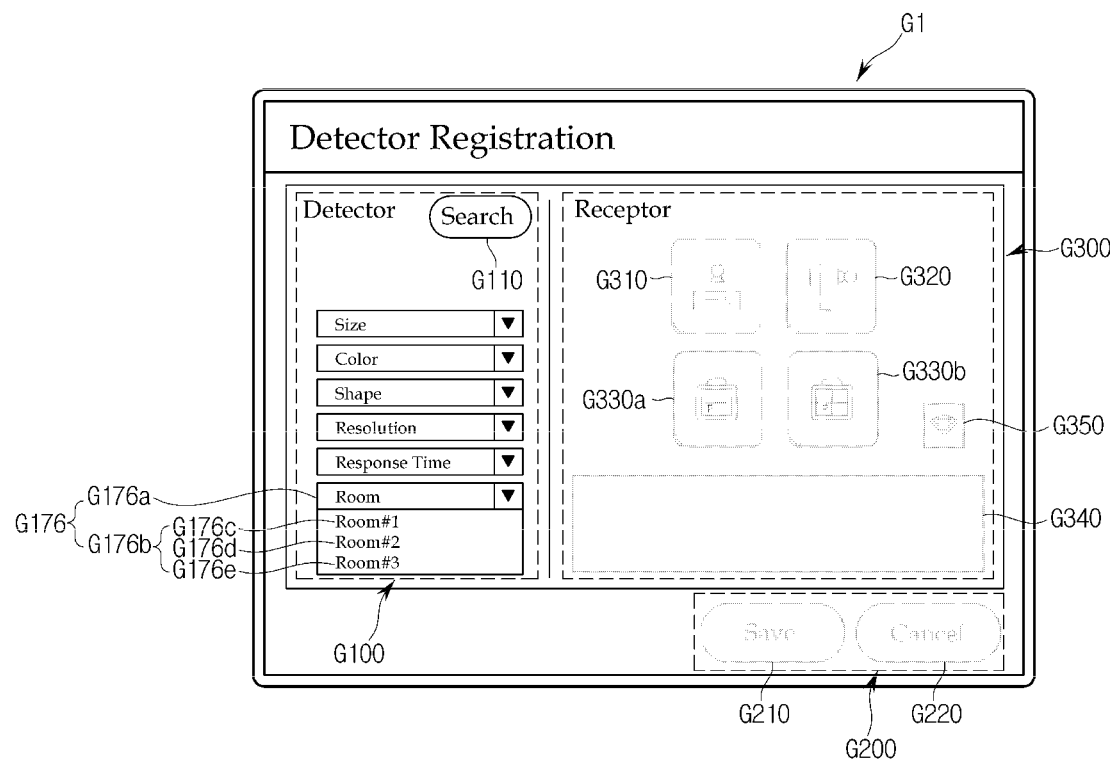
FIG. 46 is a view illustrating the graphic user interface for inputting a searching condition with respect to a diagnosis room in which the detector is located according to an exemplary embodiment.

FIG. 46 is a view of a graphic user interface for inputting a searching condition with respect to a diagnosis room in which a detector is located.

The user may input the searching condition with respect to the diagnosis room of the x-ray detector 100.

In detail, when the user selects the diagnosis room selection item G176, the graphic user interface G1 may arrange diagnosis rooms of the x-ray detectors 100 connectable with the body 10. Also, the diagnosis room selection item G176 may include a diagnosis room selection title G176a and a diagnosis room item G176b. The diagnosis room item G176b may include a first diagnosis room item G176c, a second diagnosis room item G176d, and a third diagnosis room item G176e.

The diagnosis room selection title G176a may display the searching condition the user would like to set. For example, the diagnosis room selection title G176a may display an icon which indicates that options are unfolded in the right together with a text "Room".

The diagnosis room item G176b may display options of a diagnosis room condition the user would like to set. For example, when there are three diagnosis rooms of the x-ray detector 100 connectable with the body 10, the first diagnosis room item G176c is an item for selecting a first diagnosis room that is one of the diagnosis rooms of the x-ray detector 100 connectable with the body 10 and may be displayed as a text "Room #1". Also, the second diagnosis room item G176d is an item for selecting a second diagnosis room that is one of the diagnosis rooms of the x-ray detector 100 connectable with the body 10 and may be displayed as a text "Room #2". Also, the third diagnosis room item G176e is an item for selecting a third diagnosis room that is one of the diagnosis rooms of the x-ray detector 100 connectable with the body 10 and may be displayed as a text "Room #3".

Figure 47:
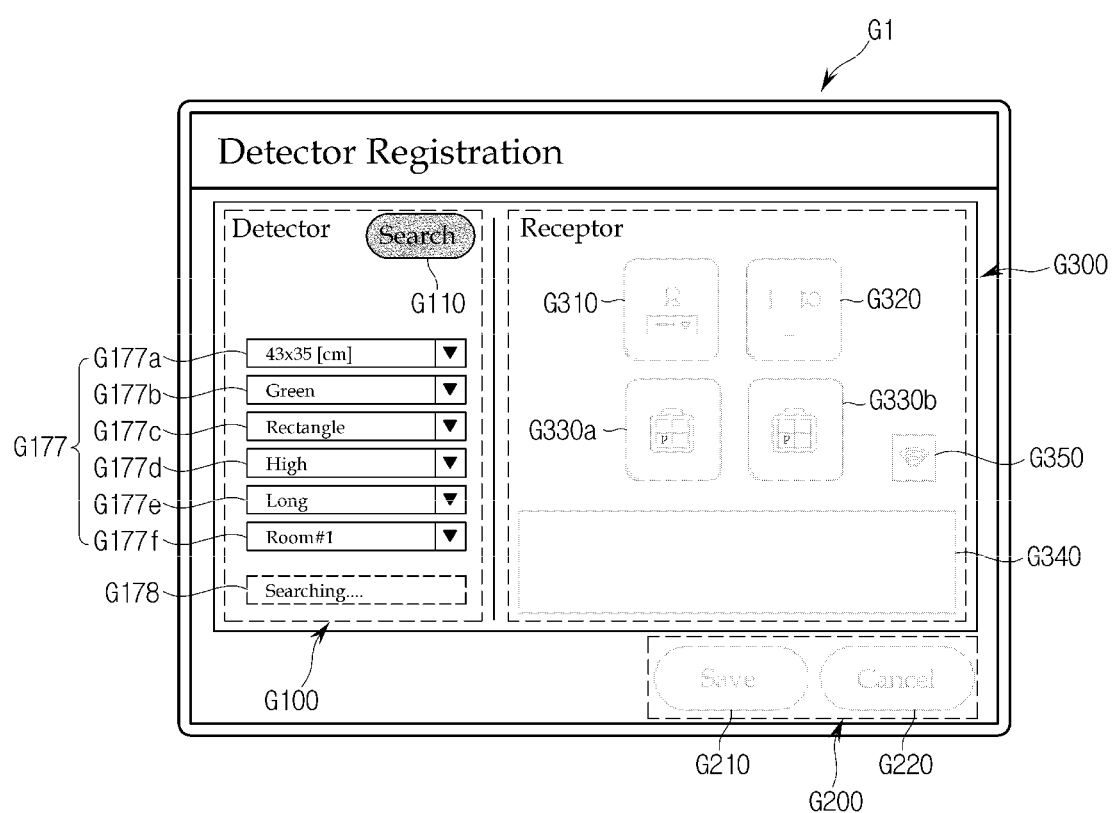
FIG. 47 is a view illustrating a graphic user interface while inputting detector searching conditions and searching for a detector according to an exemplary embodiment.

FIG. 47 is a view illustrating a graphic user interface while inputting detector searching conditions and searching for a detector.

When searching conditions selected by the user are set and the search button G110 is selected, the x-ray imaging apparatus 1 may search for the x-ray detector 100 connectable with the body 10 and corresponding to the set searching conditions and may display the searching through the graphic user interface G1.

In detail, the user may set the searching conditions through the graphic user interface G1 described above to search for the x-ray detector 100 which has a size of 43×35 cm, a green color, a rectangular shape, high resolution, and a long response time and is located in a first diagnosis room. Also, the graphic user interface G1 may display the searching conditions through a searching condition setting list G177 set by the user.

Here, the searching condition setting list G177 is an item for displaying searching conditions input by the user. The searching condition setting list G177 may include a size condition setting item G177a, a color condition setting item G177b, a shape condition setting item G177c, a resolution condition setting item G177d, a response time condition setting item G177e, and a diagnosis room condition setting item G177f.

The size condition setting item G177a may be an item for displaying a searching condition with respect to a size of the x-ray detector 100 set by the user. For example, when the user set a size of 43×35 cm as the searching condition to search for the x-ray detector 100 having a corresponding size, the size condition setting item G177a may display a text "43×35 [cm]" as shown in FIG. 47.

The color condition setting item G177b may be an item for displaying a searching condition with respect to a color of the x-ray detector 100 set by the user. For example, when the user set green as the searching condition to search for the x-ray detector 100 having a corresponding color, the color condition setting item G177b may display a text "Green" as shown in FIG. 47.

The shape condition setting item G177c may be an item for displaying a searching condition with respect to a shape of the x-ray detector 100 set by the user. For example, when the user set a rectangle as the searching condition to search for the x-ray detector 100 having a corresponding shape, the shape condition setting item G177c may display a text "Rectangle" as shown in FIG. 47.

The resolution condition setting item G177d may be an item for displaying a searching condition with respect to a resolution level of the x-ray detector 100 set by the user. For example, when the user set high resolution as the searching condition to search for the x-ray detector 100 having a corresponding resolution level, the resolution condition setting item G177d may display a text "High" as shown in FIG. 47.

The response time condition setting item G177e may be an item for displaying a searching condition with respect to a response time of the x-ray detector 100 set by the user. For example, when the user set low speed as the searching condition to search for the x-ray detector 100 having a corresponding response time, the response time condition setting item G177e may display a text "Long" as shown in FIG. 47.

The diagnosis room condition setting item G177f may be an item for displaying a searching condition with respect to a diagnosis room of the x-ray detector 100 set by the user. For example, when the user set a first diagnosis room as the searching condition to search for the x-ray detector 100 located in a corresponding diagnosis room, the diagnosis room condition setting item G177f may display a text "Room #1" as shown in FIG. 47.

Also, the graphic user interface G1 may allow the user to check the searching conditions set by the user and then may search for the x-ray detector 100 suitable for the searching conditions. When the user selects the search button G110 after checking the searching conditions, the graphic user interface G1 may display a text "Searching . . . " on a searching state screen G178 to allow the user to recognize that searching is being performed.

Also, the workstation 200 may search for the x-ray detector 100 suitable for the input searching conditions and may display the searched x-ray detector 100 on the graphic user interface G1.

Also, when the x-ray detector 100 suitable for the input searching conditions is not searched, the workstation 200 may search for and display the x-ray detector 100 having conditions similar to the searching conditions. Here, the similar conditions are previously set setting values at a point in time of designing, manufacturing, or using and may be options within a range similar to the searching conditions input by the user.

For example, among the x-ray detectors 100, the workstation 200 may display the x-ray detector 100 which corresponds to the size, color, shape, resolution, and response time among the searching conditions but is not located in the first diagnosis room. In detail, the communication interface 260 may communicate with the server 401 to check the x-ray detectors 100 located in other diagnosis rooms and may display the x-ray detector 100 which has a size of 43×35 cm, green color, rectangular shape, high resolution, and long response time and a diagnosis room in which the x-ray detector 100 is located, on the workstation 200. Also, the workstation 200 may display the x-ray detector 100 which has the size of 43×35 cm, green color, rectangular shape, high resolution, and long response time and an address of a clinic in which the corresponding x-ray detector 100 is located.

As described above, referring to FIGS. 37 to 47, the graphic user interface has been described mainly with setting the searching conditions of the x-ray detector 100. However, the same graphic user interface may be used when a plurality of detectors connectable with the body 10 are searched, recognized, and then classified.

In the exemplary embodiments described above, the graphic user interface G1 displays a plurality of searched detectors one by one. However, it is not limited thereto and it is possible to display the plurality of searched detectors at the same time. Hereinafter, referring to FIGS. 48 and 53, embodiment for displaying searched x-ray detectors at the same time will be described.

Figure 48:
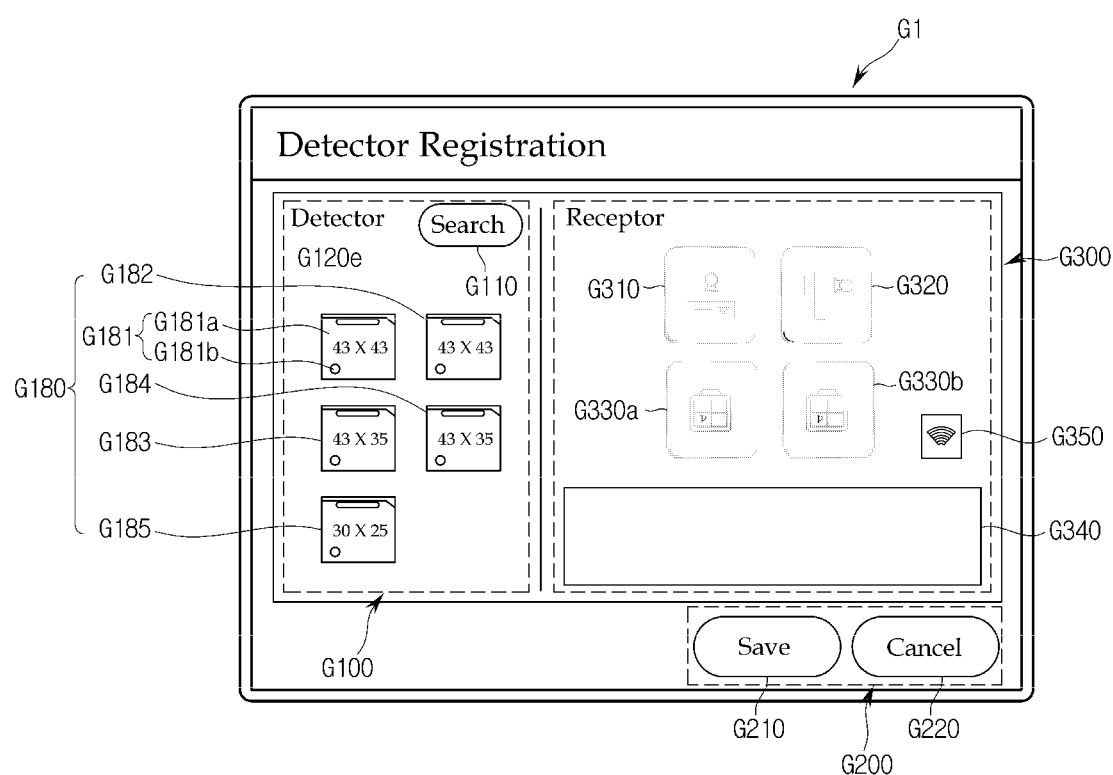
FIG. 48 is a view of a graphic user interface after searching for a detector and before selecting the detector according to an exemplary embodiment.
Figure 49:
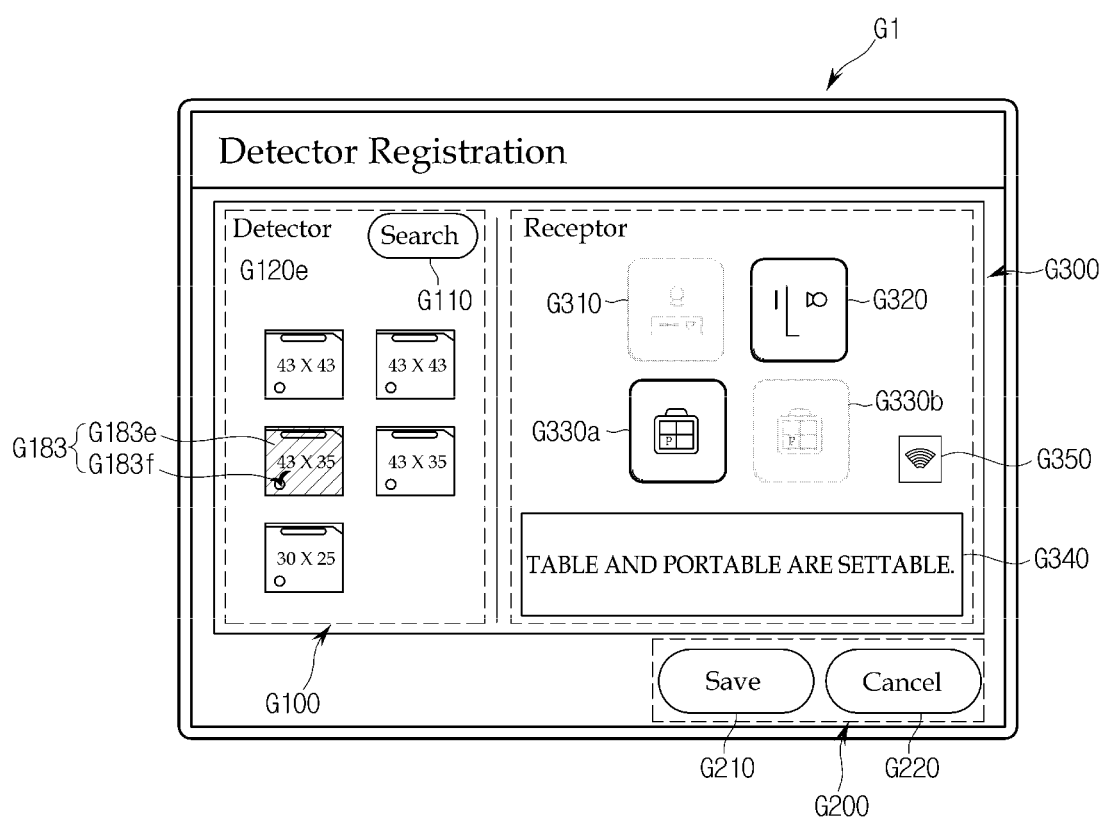
FIG. 49 is a view of a graphic user interface after searching for a detector and after selecting the detector according to an exemplary embodiment.
Figure 50:
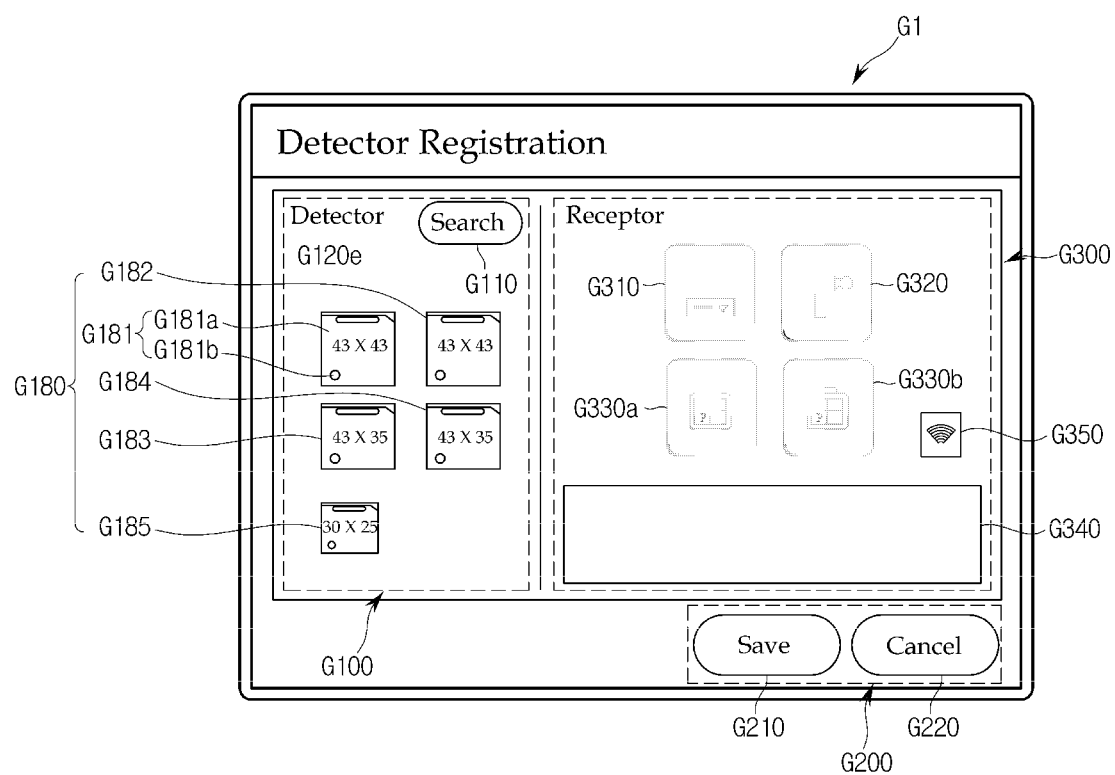
FIG. 50 is a view of a graphic user interface after searching for a detector and after selecting the detector according to an exemplary embodiment.
Figure 51:
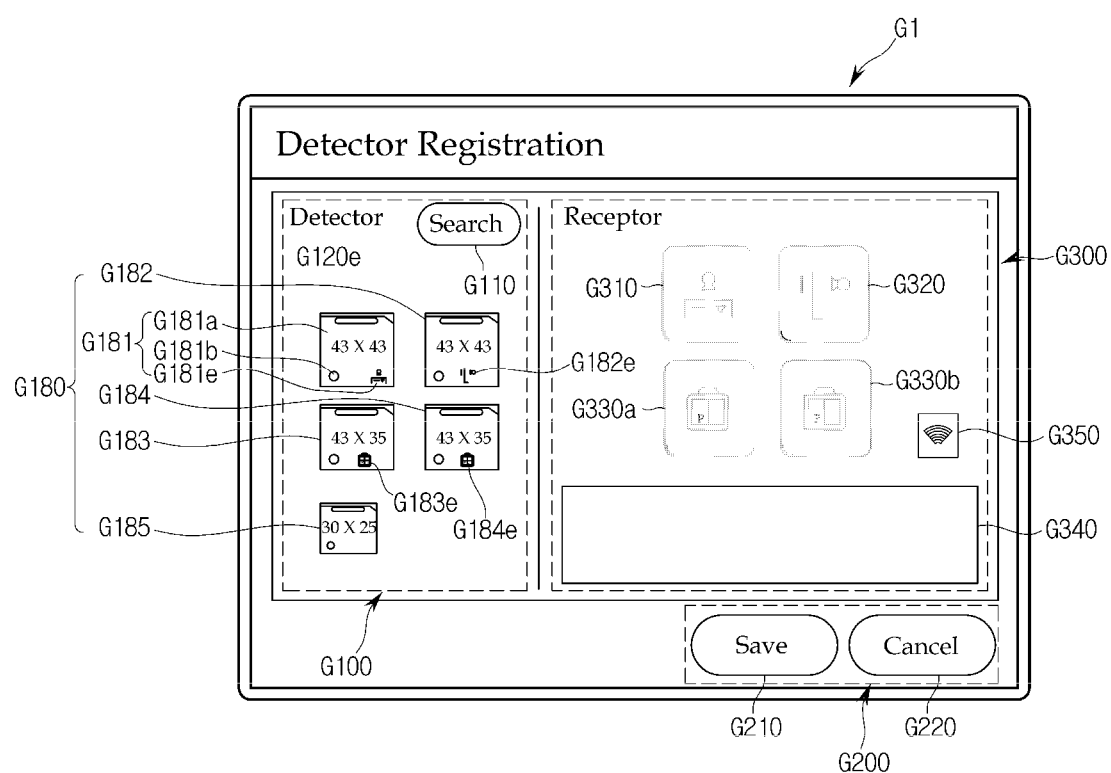
FIG. 51 is a view of a graphic user interface after searching for a detector and after selecting the detector according to an exemplary embodiment.
Figure 52:
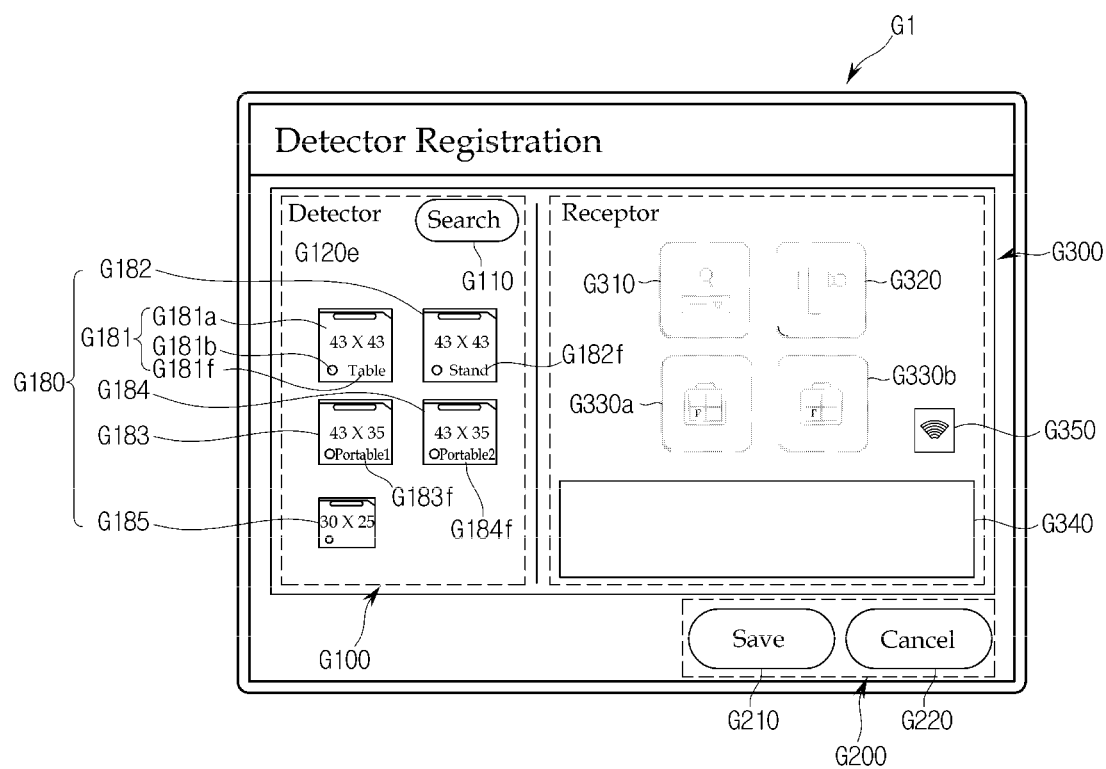
FIG. 52 is a view of a graphic user interface after searching for a detector and after selecting the detector according to an exemplary embodiment.
Figure 53:
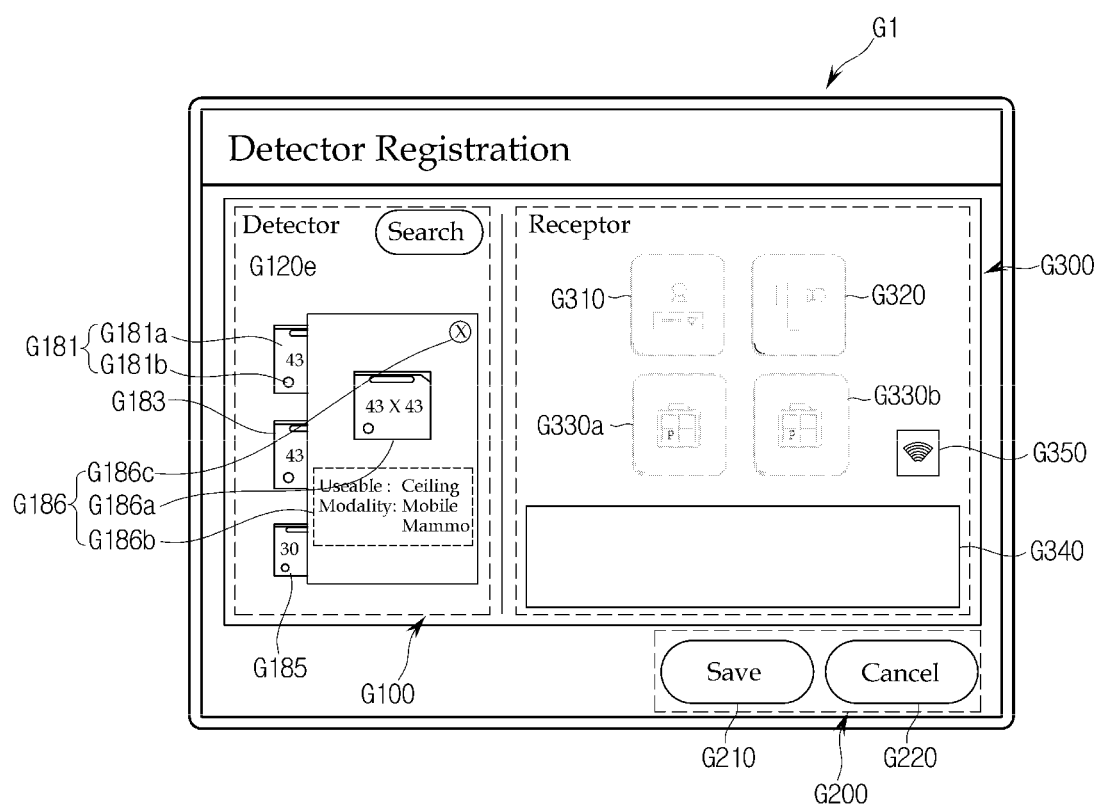
FIG. 53 is a view of a graphic user interface after searching for a detector and after selecting the detector according to an exemplary embodiment.

FIG. 48 is a view of a graphic user interface after searching for a detector and before selecting the detector. FIG. 49 is a view of a graphic user interface after searching for a detector and after selecting the detector. FIG. 50 is a view of a graphic user interface after searching for a detector and after selecting the detector according to an exemplary embodiment. FIG. 51 is a view of a graphic user interface after searching for a detector and after selecting the detector according to an exemplary embodiment. FIG. 52 is a view of a graphic user interface after searching for a detector and after selecting the detector according to an exemplary embodiment. FIG. 53 is a view of a graphic user interface after searching for a detector and after selecting the detector according to an exemplary embodiment.

When a plurality of x-ray detectors 100 connectable with the body 10 are searched, the graphic user interface G1 may display the plurality of x-ray detectors 100 in a plurality of icons together with sizes and shapes of the x-ray detectors 100.

In detail, the detector screen G100 of the graphic user interface G1 may include a detector icon G180. The detector icon G180 is an icon which displays the plurality of searched x-ray detectors 100 in one screen at the same time and receives a selection of the user to select. Also, the detector icon G180 may include a first detector icon G181, a second detector icon G182, a third detector icon G183, a fourth detector icon G184, and a fifth detector icon G185.

The first detector icon G181 is an icon that refers to a first x-ray detector. As shown in FIG. 48, the user may recognize that the first detector icon G181 indicates the x-ray detector 100 which has a size of 43×43 cm. Also, the first detector icon G181 may include a first detector size icon G181*a* and a first detector selection icon G181*b*. The first detector size icon G181*a* is an icon which displays a size of the first x-ray detector and may display a text "43×43". Also, the first detector selection icon G181*b* is an icon which displays whether the user selects the first x-ray detector and may be displayed as a circle at a left bottom of the first detector icon G181.

The second detector icon G182 is an icon which indicates a second x-ray detector. As shown in FIG. 48, the user may recognize that the second detector icon G182 is the x-ray detector 100 which has a size of 43×43 cm.

The third detector icon G183 is an icon which indicates a third x-ray detector. As shown in FIG. 48, the user may recognize that the third detector icon G183 is the x-ray detector 100 which has a size of 43×35 cm.

The fourth detector icon G184 is an icon which indicates a fourth x-ray detector. As shown in FIG. 48, the user may recognize that the fourth detector icon G184 is the x-ray detector 100 which has a size of 43×35 cm.

The fifth detector icon G185 is an icon which indicates a fifth x-ray detector. As shown in FIG. 48, the user may recognize that the fifth detector icon G185 is the x-ray detector 100 which has a size of 30×25 cm.

Also, the first detector icon G181, the second detector icon G182, the third detector icon G183, the fourth detector icon G184, and the fifth detector icon G185 may be distinguished in size of the x-ray detectors corresponding to the respective icons using sizes and shapes of the icons instead of texts.

For example, the x-ray detector 100 which has a square shape and a size of 43×43 cm may be shown as the first detector icon G181 and the second detector icon G182 shown in FIG. 50. For example, the x-ray detector 100 which has a rectangular shape and a size of 43×35 cm may be shown as the third detector icon G183 and the fourth detector icon G184 shown in FIG. 50. For example, the x-ray detector 100 which has a rectangular shape and a size of 30×25 cm may be shown as the fifth detector icon G185 shown in FIG. 50.

Also, the graphic user interface G1 may display mounting portions on which the x-ray detectors corresponding to the respective detector icons G180 are presently mounted.

For example, when the x-ray detector 100 corresponding to the first detector icon G181 is presently mounted on an imaging table, as shown in FIG. 51, the graphic user interface G1 may display a first mounting portion icon G181*e*. Also, as shown in FIG. 52, the graphic user interface G1 may display a text "table" through a first mounting portion text G181*f*.

When the x-ray detector 100 corresponding to the second detector icon G182 is presently mounted on an imaging table, as shown in FIG. 51, the graphic user interface G1 may display a second mounting portion icon G182*e*. Also, as shown in FIG. 52, the graphic user interface G1 may display a text "stand" through a second mounting portion text G182*f*.

When the x-ray detector 100 corresponding to the third detector icon G183 is presently mounted on a first portable mounting portion, as shown in FIG. 51, the graphic user interface G1 may display a third mounting portion icon G183*e*. Also, as shown in FIG. 52, the graphic user interface G1 may display a text "Portable1" through a third mounting portion text G183*f*.

When the x-ray detector 100 corresponding to the fourth detector icon G184 is presently mounted on a second portable mounting portion, as shown in FIG. 51, the graphic user interface G1 may display a fourth mounting portion icon G184*e*. Also, as shown in FIG. 52, the graphic user interface G1 may display a text "Portable2" through a fourth mounting portion text G184*f*.

When the x-ray detector 100 corresponding to the fifth detector icon G185 is not presently mounted on a mounting portion, as shown in FIGS. 51 and 52, a mounting portion icon and a mounting portion text may not be displayed.

Also, when the user would like to select the third x-ray detector among five x-ray detectors 100, the user may select the third detector icon G183.

In this case, as shown in FIG. 49, the third detector icon G183 in the graphic user interface G1 may include a third detector activating icon G183*f* and a third detector activating background G183*e*.

When the user selects the third x-ray detector, the third detector activating icon G183*c* may check a third detector selection icon G183*b* to indicate that the user selects the third x-ray detector. When the user selects the third x-ray detector, the third detector activating background G183*d* may change a background of the third detector icon 183 to be deep to indicate that the user selects the third x-ray detector.

Also, as shown in FIG. 53, when the user selects the third detector icon G183 to select the third x-ray detector, a selected detector information window G186 which is a separate window may be displayed.

The selected detector information window G186 may display a size, a shape, a mounting portion on which the selected detector is mounted, and an available modality of the selected detector.

In detail, the selected detector information window G186 may include a selected detector icon G186a which displays the size and shape of the selected detector, an available modality text G186b which displays the available modality for the selected detector, and a selected detector information window closing key G186c which can close the selected detector information window G186.

As described above, the graphic user interface G1 has been described as being used in a ceiling type x-ray imaging apparatus which includes a table mounting portion, a stand mounting portion, and a portable mounting portion. Hereinafter, referring to FIGS. 54 to 58, embodiment g with respect to a graphic user interface of a mobile type x-ray imaging apparatus which includes a portable mounting portion will be described.

Figure 54:
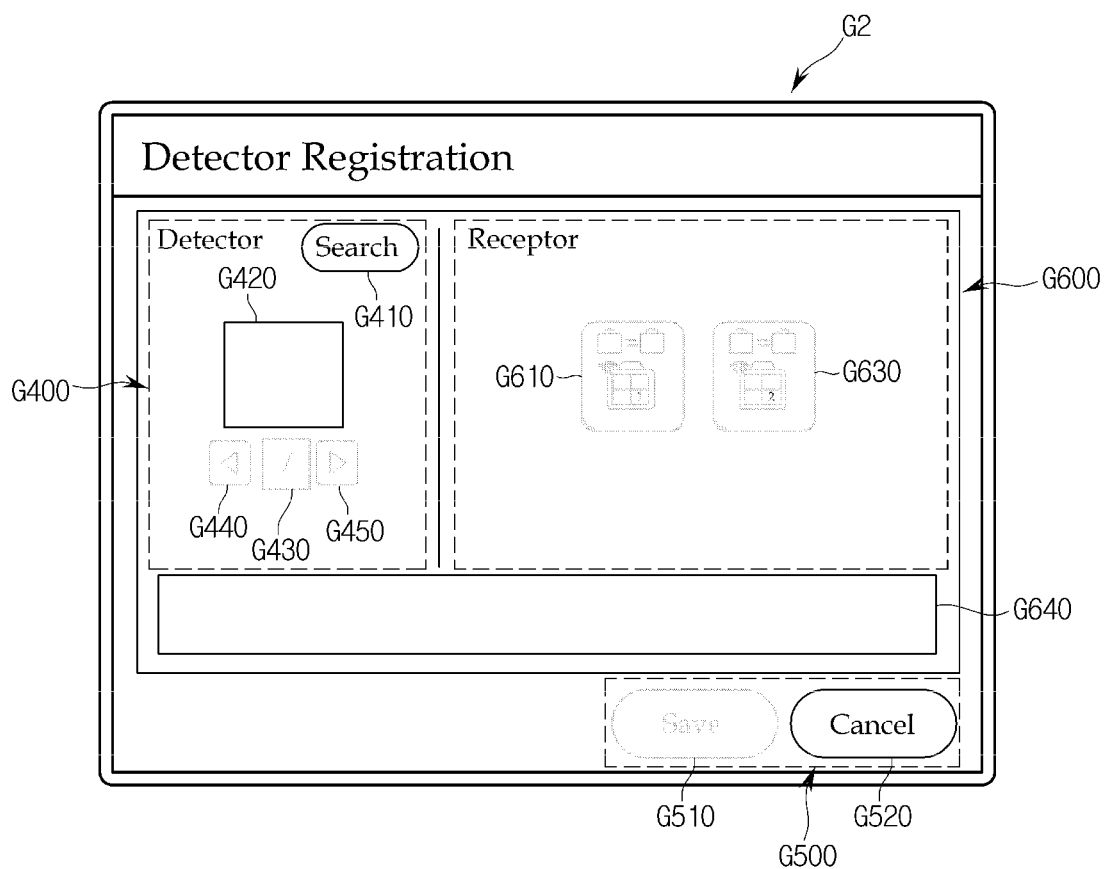
FIG. 54 is a view of a graphic user interface before searching for a detector according to an exemplary embodiment.
Figure 55:
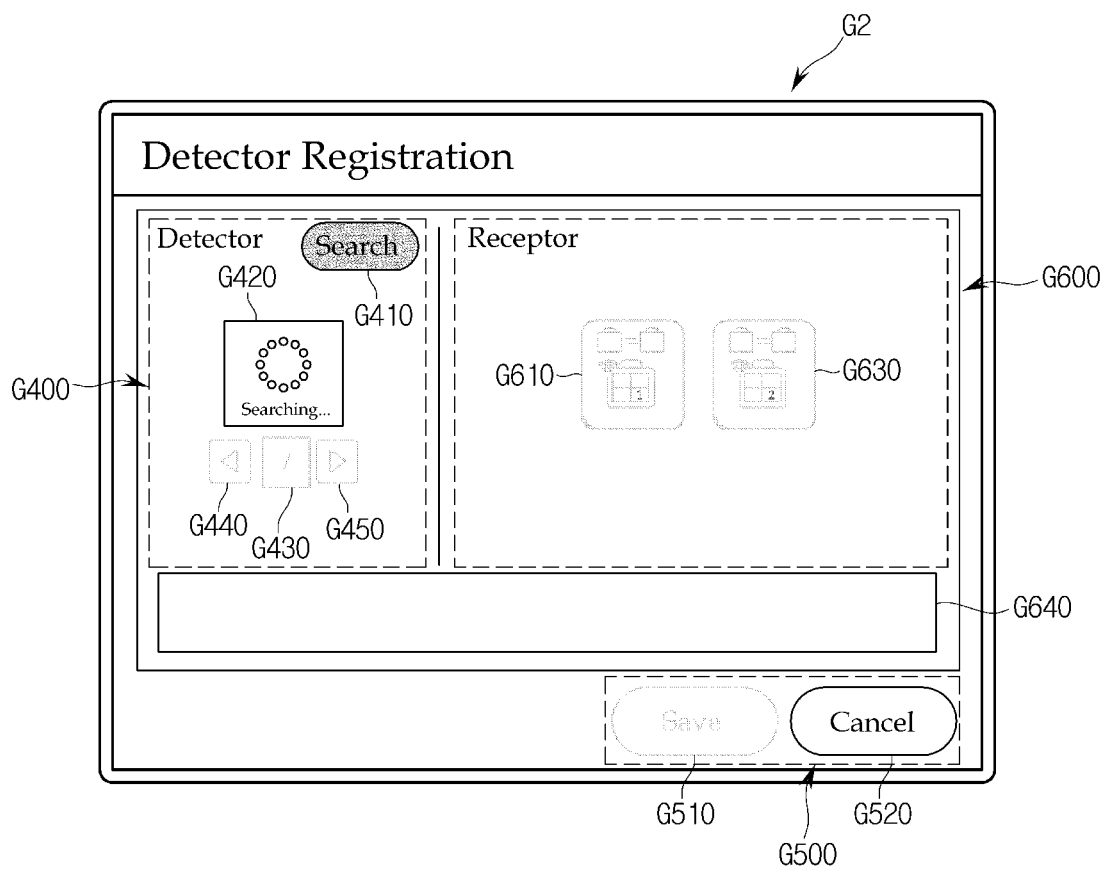
FIG. 55 is a view of the graphic user interface while searching for the detector according to an exemplary embodiment.

FIG. 54 is a view of a graphic user interface before searching for a detector. FIG. 55 is a view of a graphic user interface while searching for a detector.

When detector setting is selected, as shown in FIG. 54, a graphic user interface G2 is executed. The graphic user interface G2 is to set and save an environment for using the x-ray detector 100 and may include a detector screen G400, a mounting portion screen G600, and a setting saving screen G500.

The detector screen G400 is located in the left of the graphic user interface G2. Also, the detector screen G400 may provide a user interface for searching for the x-ray detector 100 presently usable in the x-ray imaging apparatus 1 and selecting the searched x-ray detector 100. Also, the detector screen G400 may include a search button G410 which gives a command for searching for the x-ray detector 100 usable in the x-ray imaging apparatus 1 on a right top end, a detector environment screen G420 which displays a type or size of the selected x-ray detector 100, a detector sequence screen G430 which displays a sequence of the presently selected x-ray detector 100 among a plurality of searched x-ray detectors 100, a previous ranking selection button G440 for selecting the x-ray detector 100 at a previous ranking among the plurality of searched x-ray detectors 100, and a next ranking selection button G450 for selecting the x-ray detector 100 at a next ranking among the plurality of searched x-ray detectors 100.

The mounting portion screen G600 is located in the right of the graphic user interface G2. Also, the mounting portion screen G600 may provide a user interface for displaying the mounting portion 300 on which the selected x-ray detector 100 is mountable and selecting the mounting portion 300 to mount. In detail, the mounting portion screen G600 may display the mountable mounting portion 300 based on the size of the selected x-ray detector 100 and a size of the mounting portion 300. Also, the mounting portion screen G600 may include a first portable selection button G610 selected to mount the selected x-ray detector 100 on the first portable mounting portion 330a, a second portable selection button G630 selected to mount the selected x-ray detector 100 on the second portable mounting portion 330b, and an available mounting portion text screen G640 which displays the mounting portion 300 on which the selected x-ray detector 100 is mountable as a text.

The setting saving screen G500 is located at a right bottom of the graphic user interface G2. Also, the setting saving screen G500 may provide a user interface for saving and transferring a communication state of the selected x-ray detector 100 and information on setting a type of the mounting portion 300 to mount to the x-ray detector 100. Also, the setting saving screen G500 may include a saving button G510 which saves and transfers setting information on the x-ray detector 100 and the mounting portion 300 to the x-ray detector 100 in the left and a cancel button G520 which cancels the setting on the x-ray detector 100 and the mounting portion 300 in the right.

First, when the detector setting is selected, the graphic user interface G2 is executed and displayed while all buttons and screens are being deactivated except the search button G410 of the detector screen G400 as shown in FIG. 54. Accordingly, the user may search for the x-ray detector 100 presently usable in the x-ray imaging apparatus 1 by selecting the search button G410.

Also, when the search button G410 is selected, the workstation 200 may identify the respective x-ray detectors 100 by comparing the previously stored detector pairing data 271 with the identification information of the x-ray detectors 100 and may search for the usable x-ray detector 100. In the case of performing such process described above, as shown in FIG. 55, the search button G410 of the detector screen G400 may be displayed while given with a shadow effect which indicates a selected state, and the detector environment screen G420 may display that the x-ray imaging apparatus 1 is presently searching for the usable x-ray detector 100. Also, all the buttons and screens may be deactivated except the search button G410 and the detector environment screen G420 of the detector screen G400.

After that, when the plurality of x-ray detectors 100 usable for the x-ray imaging apparatus 1 are searched, the graphic user interface G2 for selecting one of the searched x-ray detectors 100 and setting the communication state and the type of the mounting portion 300 to mount may be executed.

Figure 56:
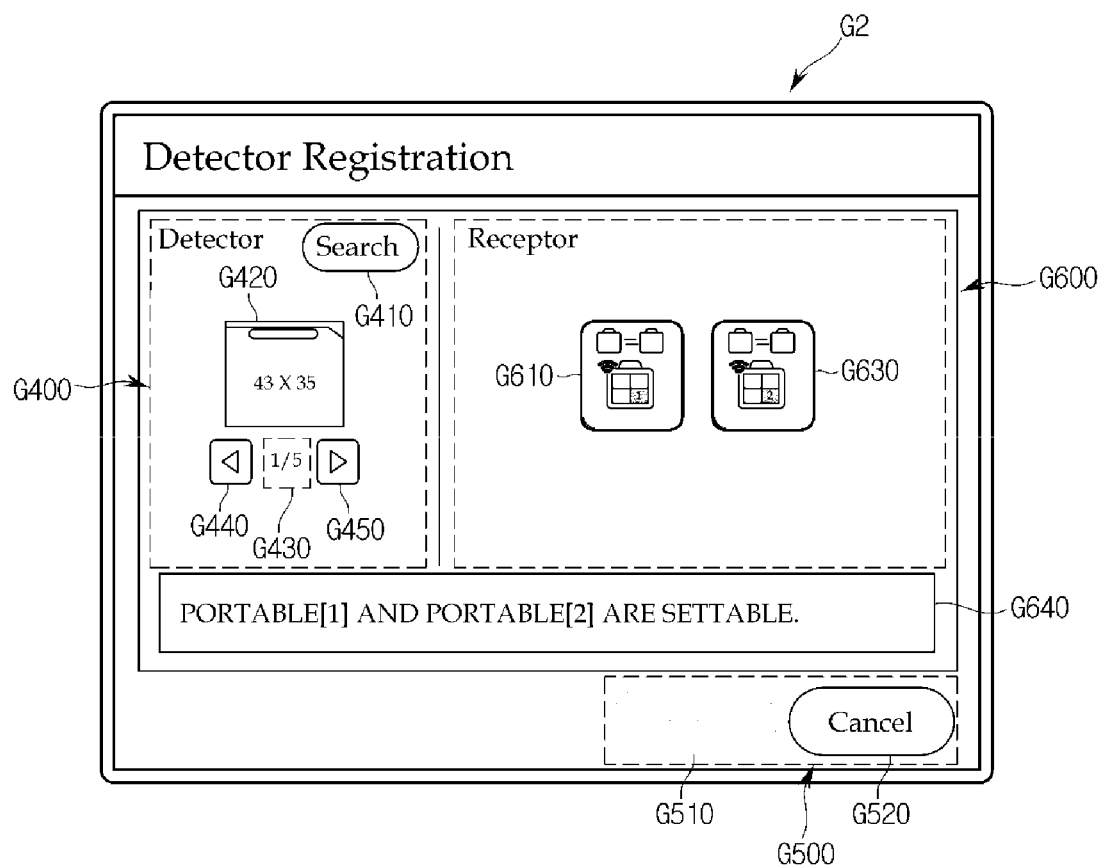
FIG. 56 is a view of the graphic user interface which displays a connectable mounting portion for a selected x-ray detector after detector-searching according to an exemplary embodiment.
Figure 57:
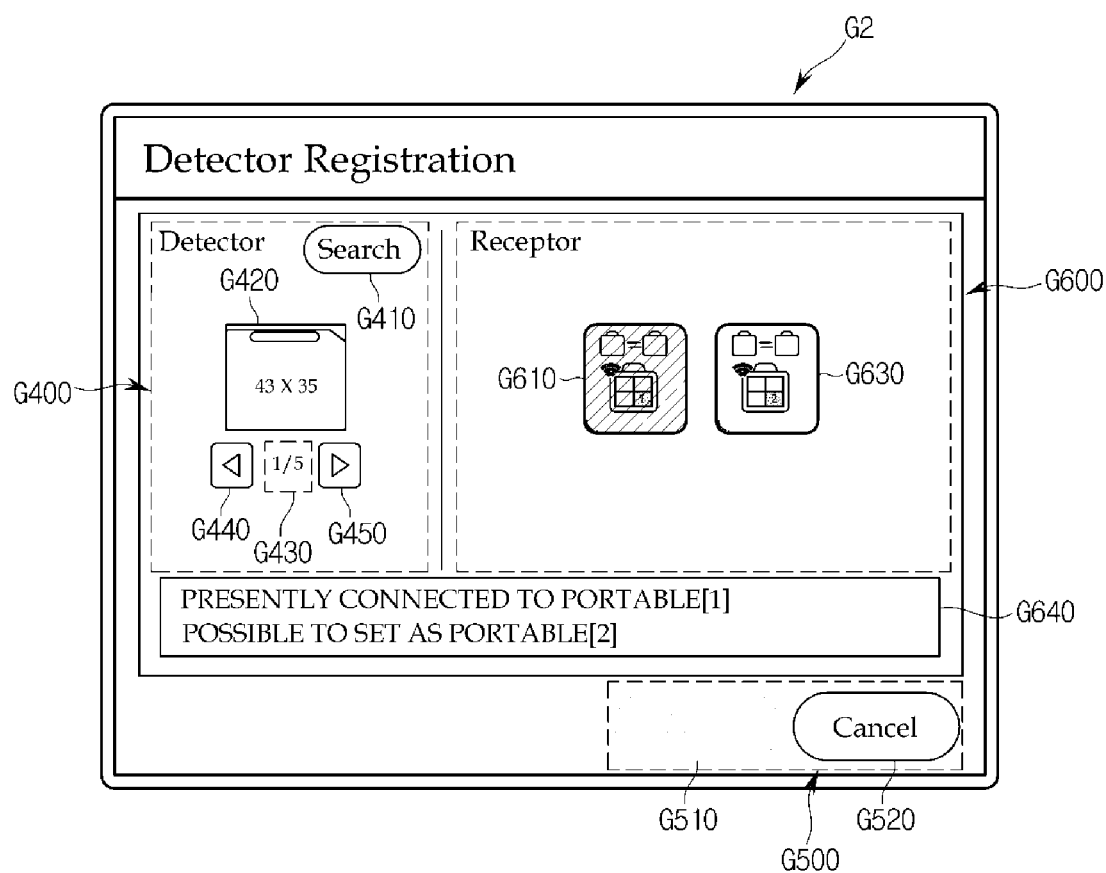
FIG. 57 is a view of the graphic user interface which displays the connectable mounting portion and a presently connected mounting portion of the selected x-ray detector after detector-searching according to an exemplary embodiment.
Figure 58:
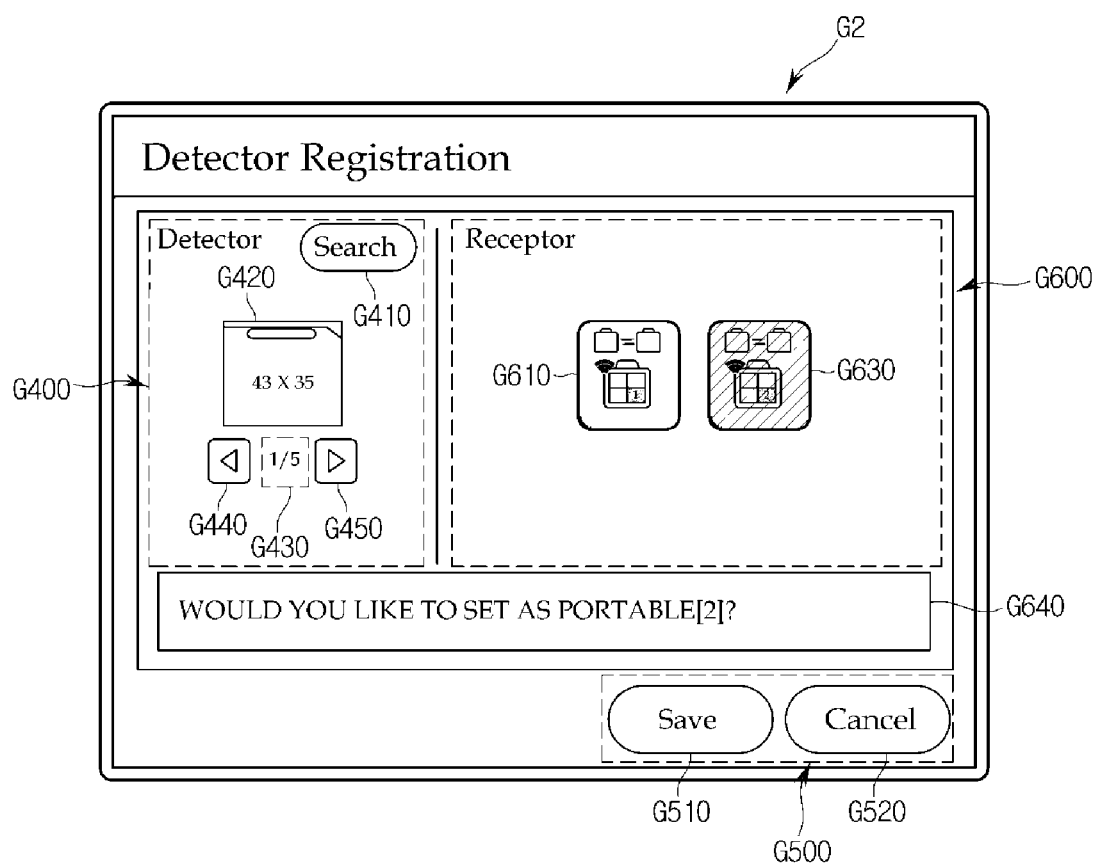
FIG. 58 is a view of the graphic user interface for changing a mounting portion to be connected to the selected x-ray detector after detector-searching according to an exemplary embodiment.

FIG. 56 is a view of a graphic user interface which displays a connectable mounting portion for a selected x-ray detector after detector-searching. FIG. 57 is a view of the graphic user interface which displays the connectable mounting portion and a presently connected mounting portion of the selected x-ray detector 100 after detector-searching. FIG. 58 is a view of a graphic user interface for changing a mounting portion to be connected to the selected x-ray detector after detector-searching.

As shown in FIG. 56, after searching for the x-ray detector 100 usable for the x-ray imaging apparatus 1, the graphic user interface G2 provides an interface for selecting one x-ray detector 100 among the plurality of x-ray detectors 100 and setting the selected x-ray detector 100.

In detail, a shadow of the search button G410 of the detector screen G400 disappears and the search button G410 returns to an activated state. Also, the selected detector environment screen G420 may display the presently selected detector to display that a size of the selected detector is 43×35 cm or may display a distinction sign displayed on the detector display 190 to distinguish the selected detector from other detectors. Also, the selected detector sequence screen G430 displays the number of the x-ray detectors 100 usable for the x-ray imaging apparatus 1 and a ranking of the presently selected x-ray detector 100. That is, the selected detector sequence screen G430 may display "1/5" which indicates that the number of the x-ray detectors 100 presently usable for the x-ray imaging apparatus 1 is 5 and the ranking of the presently selected x-ray detector 100 is the first. Also, the previous ranking selection button G440 and the next ranking selection button G450 may be activated to select one of the x-ray detectors 100 presently usable for the x-ray imaging apparatus 1.

Also, in the case of the first portable selection button G610 and the second portable selection button G630 in the mounting portion screen G600, only the selection button corresponding to the mounting portion 300 mountable based on the size of the selected x-ray detector 100 may be activated. For example, when the size of the selected x-ray detector 100 is 43×35 cm and the mounting portion 300 having a size to mount the selected x-ray detector 100 corresponds the first portable mounting portion 330*a* and the second portable mounting portion 330*b*, the graphic user interface G2 may activate the first portable selection button G610 and the second portable selection button G630. That is, the user may select one of the first portable selection button G610 and the second portable selection button G630 to determine the mounting portion 300 on which the selected x-ray detector 100 is to be mounted.

Also, the first portable selection button G610 and the second portable selection button G630 may each display a swap icon and a wireless setting icon to display whether the first portable mounting portion 330*a* and the second portable mounting portion 330*b* are swapped with each other and whether wireless communication is being performed.

The available mounting portion text screen G640 in the mounting portion screen G600 may display the mounting portion 300 on which the selected x-ray detector 100 is mountable as a text. For example, when the size of the selected x-ray detector 100 is 43×35 cm and the mounting portion 300 having a size to mount the selected x-ray detector 100 corresponds to the first portable mounting portion 330*a* and the second portable mounting portion 330*b*, the graphic user interface G2 may display a text "Portable[1] and Portable[2] are settable." on the available mounting portion text screen G640.

To use conditions such as the type of the mounting portion 300, etc. set with respect to the selected x-ray detector 100, the user may give a command of saving and transferring set information to the x-ray detector 100 by selecting the saving button G510 on the setting saving screen G500. On the contrary, when the user would not like to use the conditions such as the type of the mounting portion 300 set with respect to the selected x-ray detector 100, the user may give a command of cancellation by selecting the cancel button G520 on the setting saving screen G500.

Also, when one detector is selected from the five x-ray detectors 100, the graphic user interface G2 may display the mounting portion 300 on which the selected x-ray detector 100 is presently mounted.

In detail, as shown in FIG. 57, when a first x-ray detector presently selected by the user is mounted on the first portable mounting portion 330*a*, the graphic user interface G2 may change a background of the first portable selection button G610 on the mounting portion screen G600 to a deep color to allow the user to recognize that the first x-ray detector is mounted on the first portable mounting portion 330*a*. Also, the available mounting portion text screen G640 may display a text "Presently connected to Portable[1]. Possible to set as Portable[2]."

Through this, the user may recognize that the first x-ray detector is mounted on the first portable mounting portion 330*a* and able to be mounted on the second portable mounting portion 330*b* by changing settings and may input a command.

In detail, when the user would like to shift a location of the first x-ray detector from the first portable mounting portion 330*a* on which the first x-ray detector is presently mounted into the second portable mounting portion 330*b*, the user may select the second portable selection button G630 on the mounting portion screen G600 of the graphic user interface G2. In this case, as shown in FIG. 58, a deep color background of the first portable selection button G610 on the mounting portion screen G600 of the graphic user interface G2 is changed into an original color background and an original background of the second portable selection button G630 may be changed into a deep color background. Through this, the user may recognize that the mounting portion on which the first x-ray detector is to be mounted is changed from the first portable mounting portion 330*a* to the second portable mounting portion 330*b* according to the command of the user.

Also, the available mounting portion text screen G640 may change from the text "Presently connected to Portable[1]. Possible to set as Portable[2]." to a text "Would you like to set as Portable[2]?". Through this, the user may recognize that the mounting portion on which the first x-ray detector is to be mounted is changed from the first portable mounting portion 330*a* to the second portable mounting portion 330*b* according to the command of the user.

Also, when the user would like to change the mounting portion 300 on which the first x-ray detector is to be mounted to the second portable mounting portion 330*b*, the user may select the saving button G510 on the setting saving screen G500 to give a command for saving and transferring set information to the x-ray detector 100. On the contrary, when the user would not like to change the mounting portion on which the first x-ray detector is to be mounted to the second portable mounting portion 330*b* and to maintain the first portable mounting portion 330*a*, the user may give a command of cancellation by selecting the cancel button G520 on the setting saving screen G500.

As described above, the exemplary embodiments in which a graphic user interface displays only one modality have been described. Hereinafter, embodiments in which a graphic user interface displays a plurality of modalities will be described.

Figure 59:
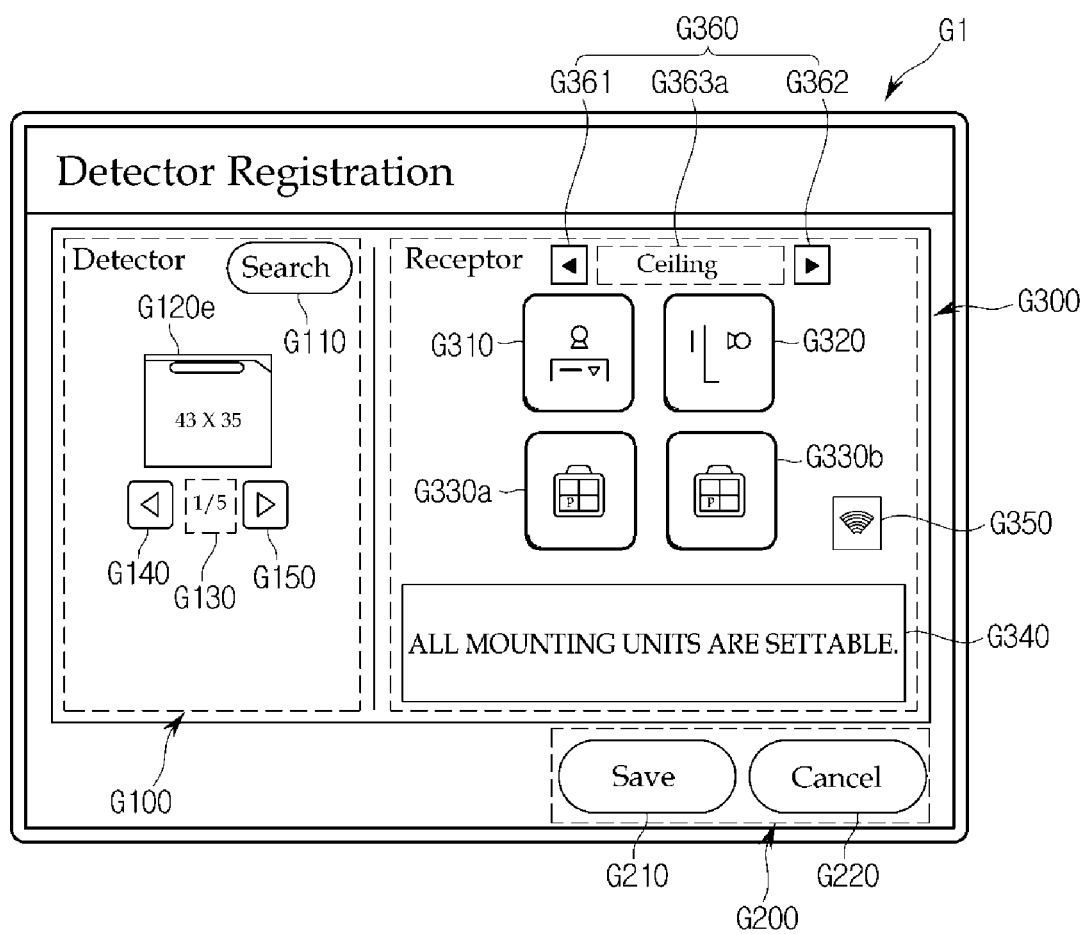
FIG. 59 is a view illustrating an example of a graphic user interface for selecting a modality and a mounting portion after detector-searching according to an exemplary embodiment.
Figure 60:
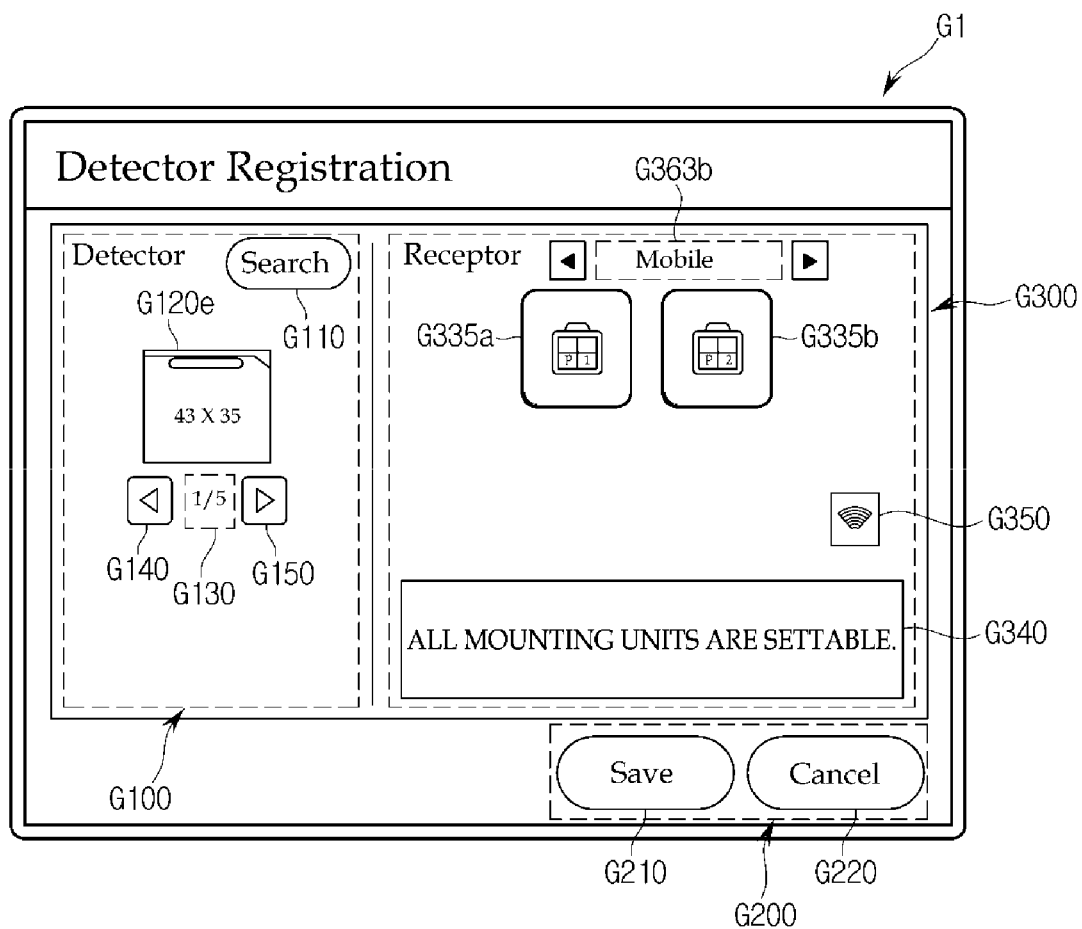
FIG. 60 is a view illustrating another example of the graphic user interface for selecting the modality and the mounting portion after detector-searching according to an exemplary embodiment.
Figure 61:
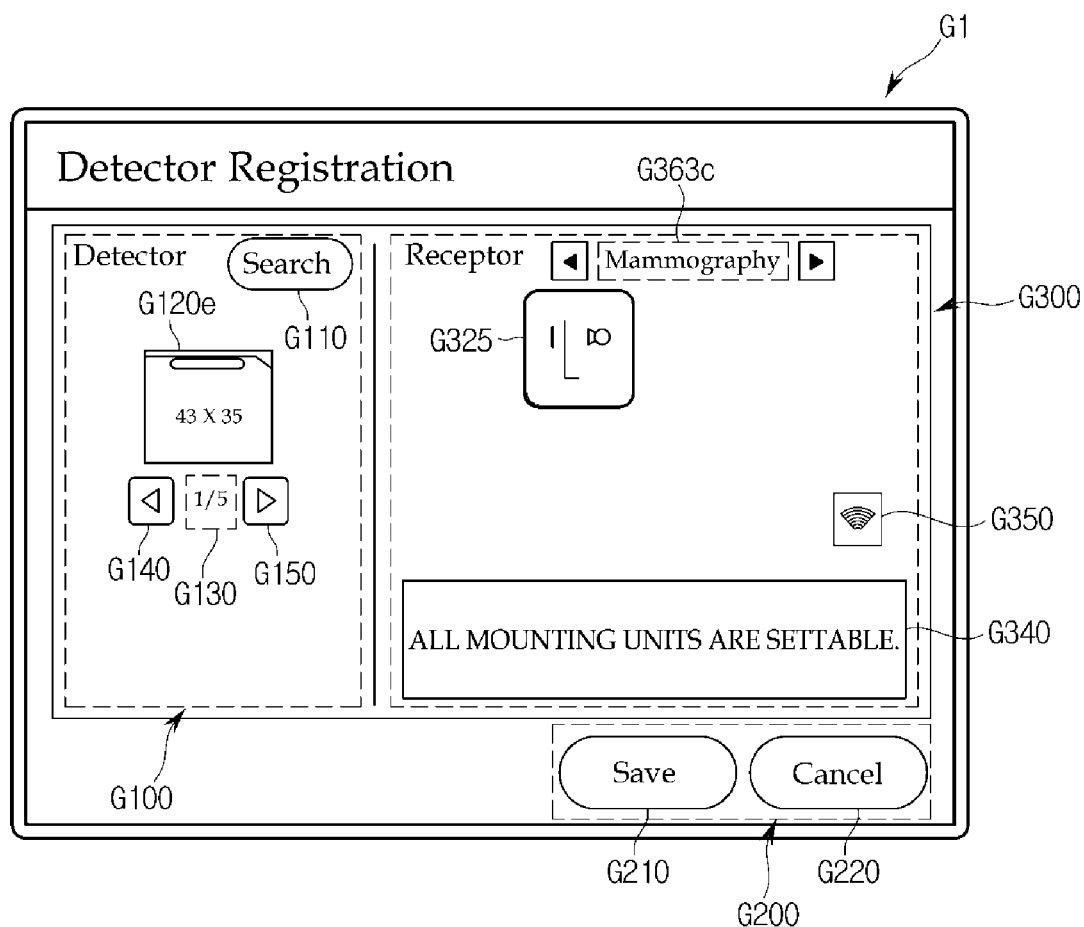
FIG. 61 is a view illustrating still another example of the graphic user interface for selecting the modality and the mounting portion after detector-searching according to an exemplary embodiment.
Figure 62:
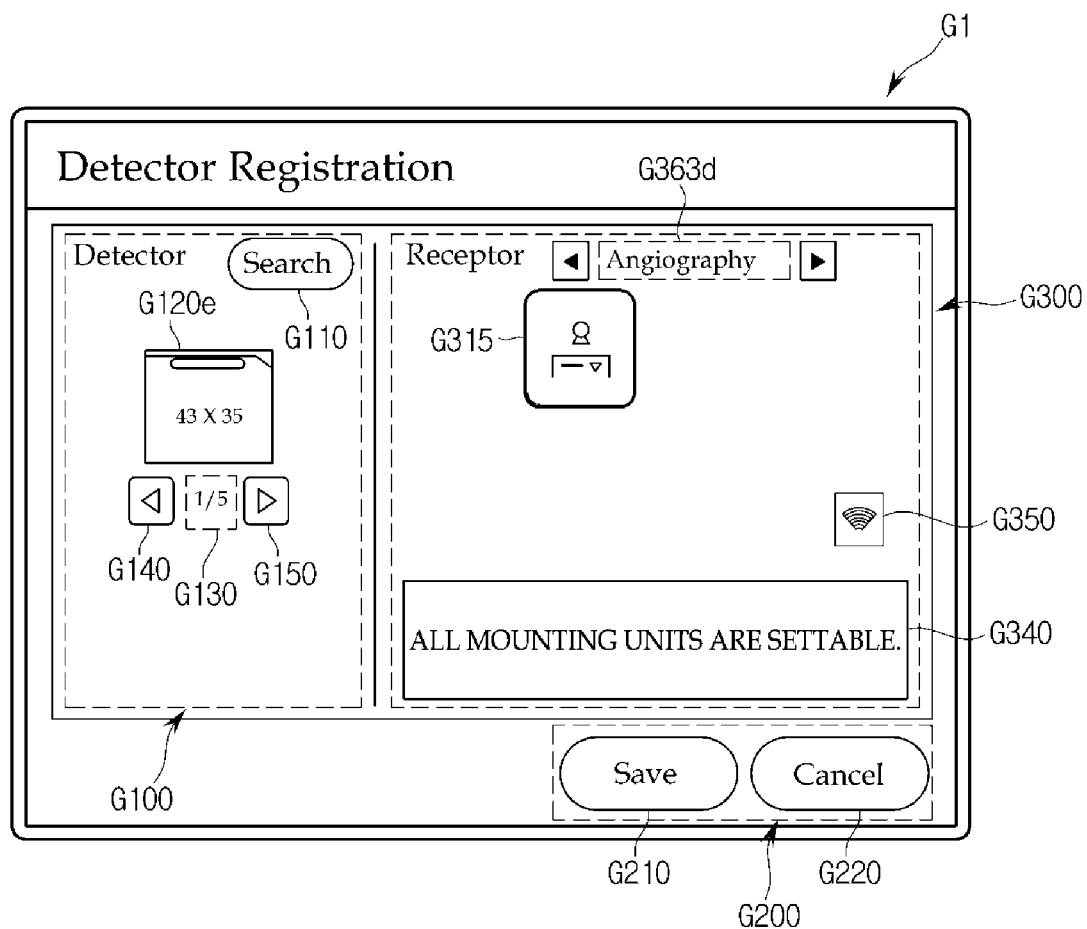
FIG. 62 is a view illustrating yet another example of the graphic user interface for selecting the modality and the mounting portion after detector-searching according to an exemplary embodiment.

FIG. 59 is a view illustrating an example of a graphic user interface for selecting a modality and a mounting portion after detector-searching according to an exemplary embodiment. FIG. 60 is a view illustrating another example of the graphic user interface for selecting the modality and the mounting portion after detector-searching according to an exemplary embodiment. FIG. 61 is a view illustrating still another example of the graphic user interface for selecting the modality and the mounting portion after detector-searching according to an exemplary embodiment. FIG. 62 is a view illustrating yet another example of the graphic user interface for selecting the modality and the mounting portion after detector-searching according to an exemplary embodiment.

The user may select and set not only the mounting portion 300 on which the x-ray detector 100 selected by the user is to be mounted but also a modality using the graphic user interface G1.

In detail, the mounting portion screen G300 may include a first modality selection screen G360. The first modality selection screen G360 is a user interface for allowing the user to select a modality on which the selected detector is to be mounted and may include a previous modality selection button G361, a next modality selection button G362, and a modality title screen G363.

Here, the previous modality selection button G361 is a button for allowing the user to select a previous modality, the next modality selection button G362 is a button for allowing the user to select a next modality, and the modality title screen G363 is a screen for specifying a type of a presently selected modality.

For example, when the user selects the first x-ray detector, the mounting portion screen G300 of the graphic user interface G1 may display a ceiling type mounting portion screen and a modality title screen G363a may display a text "Ceiling". Also, the mounting portion screen G300 of the graphic user interface G1 may display the table selection button G310, the stand selection button G320, the first portable selection button G330a, and the second portable selection button G330b and may activate one button corresponding to the mounting portion 300 mountable based on the size of the selected x-ray detector 100.

Referring to FIG. 60, when the user selects the next modality selection button G362 and selects a mobile type x-ray imaging apparatus, the mounting portion screen G300 of the graphic user interface G1 may display a mobile type mounting portion screen and a modality title screen G363b may display a text "Mobile". Also, the mounting portion screen G300 of the graphic user interface G1 may display a first portable selection button G335a and a second portable selection button G335b and may activate one button corresponding to the mounting portion 300 mountable based on the size of the selected x-ray detector 100.

Referring to FIG. 61, when the user selects the next modality selection button G362 and selects a mammography type x-ray imaging apparatus, the mounting portion screen G300 of the graphic user interface G1 may display a mammography type mounting portion screen and a modality title screen G363c may display a text "Mammography". Also, the mounting portion screen G300 of the graphic user interface G1 may display a stand selection button G325 and may activate a button corresponding to the mounting portion 300 mountable based on the size of the selected x-ray detector 100.

Referring to FIG. 62, when the user selects the next modality selection button G362 and selects an angiography type x-ray imaging apparatus, the mounting portion screen G300 of the graphic user interface G1 may display an angiography type mounting portion screen and a modality title screen G363d may display a text "Angiography". Also, the mounting portion screen G300 of the graphic user interface G1 may display a table selection button G315 and may activate a button corresponding to the mounting portion 300 mountable based on the size of the selected x-ray detector 100.

Hereinafter, referring to FIGS. 63 and 64, a graphic user interface which shifts from a separate modality selection screen to a mounting portion screen will be described.

Figure 63:
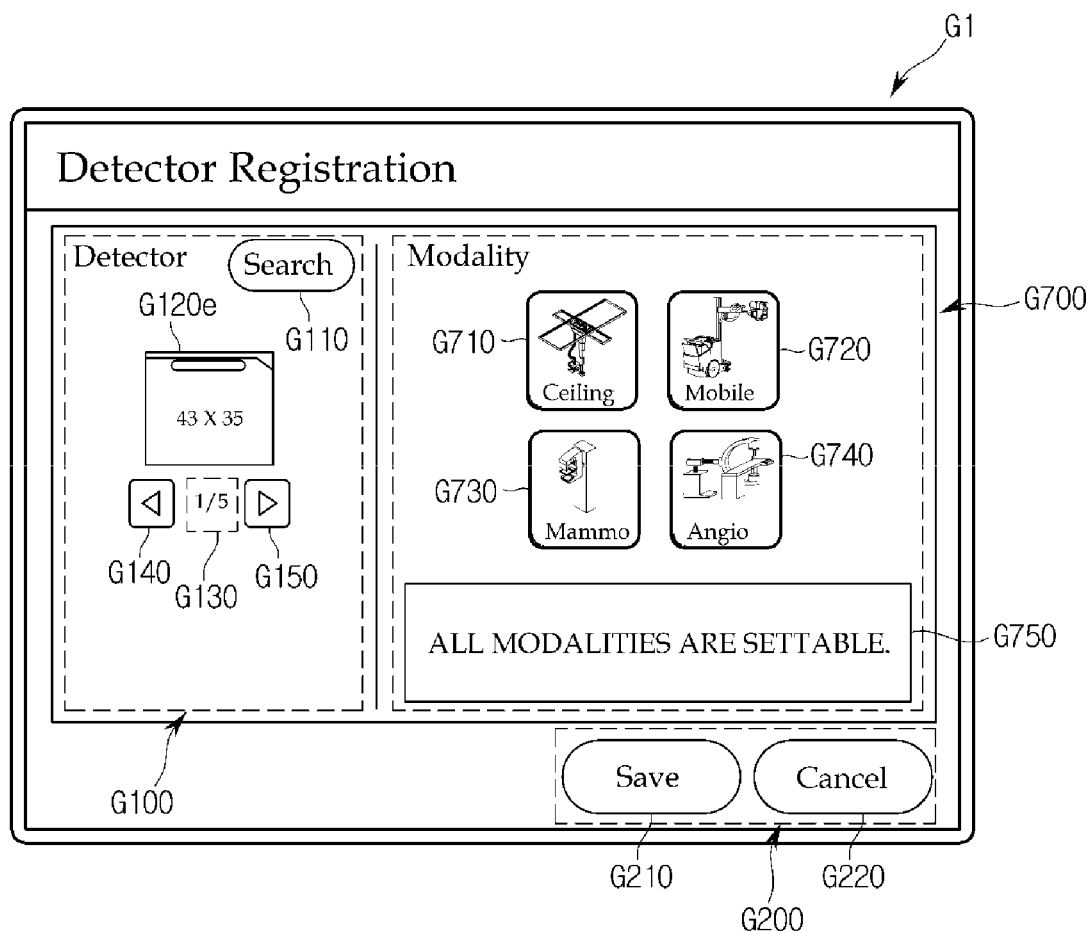
FIG. 63 is a view of a graphic user interface for selecting a modality after detector-searching according to an exemplary embodiment.

FIG. 63 is a view of a graphic user interface for selecting a modality after detector-searching according to an exemplary embodiment. FIG. 64 is a view of the graphic user interface for selecting a ceiling type modality after detector-searching according to an exemplary embodiment.

The user may select one of the plurality of x-ray detectors 100 searched as connectable with the body 10 and then may display and set a modality usable for the x-ray detector 100 or a modality preferred by the user.

In detail, as shown in FIG. 63, the graphic user interface G1 may include a second modality selection screen G700.

The second modality selection screen G700 is located in the right of the graphic user interface G1 and is a user interface for displaying a modality usable for by the selected x-ray detector 100 and selecting a modality to be set. The second modality selection screen G700 may activate a button of the modality usable for the selected x-ray detector 100 and may deactivate a button of an unusable modality.

Also, the second modality selection screen G700 may include a ceiling selection button G710, a mobile selection button G720, a mammography selection button G730, an angiography selection button G740, and an available modality text screen G750.

Here, the ceiling selection button G710 is a button for selecting a ceiling type x-ray imaging apparatus as a modality in which the selected x-ray detector 100 will be used, and the mobile selection button G720 is a button for selecting a mobile type x-ray imaging apparatus as a modality in which the selected x-ray detector 100 will be used. Also, the mammography selection button G730 is a button for selecting a mammography type x-ray imaging apparatus as a modality in which the selected x-ray detector 100 will be used, and the angiography selection button G740 is a button for selecting an angiography type x-ray imaging apparatus as a modality in which the selected x-ray detector 100 will be used. Also, the available modality text screen G750 is a screen which displays a type of a modality usable for the selected x-ray detector 100 as a text.

For example, when a modality usable for the first x-ray detector selected by the user corresponds to a ceiling type, a mobile type, a mammography type, and an angiography type, the graphic user interface G1 may activate the ceiling selection button G710, the mobile selection button G720, the mammography selection button G730, and the angiography selection button G740 and may display a text "All modalities are settable." on the available modality text screen G750.

Figure 64:
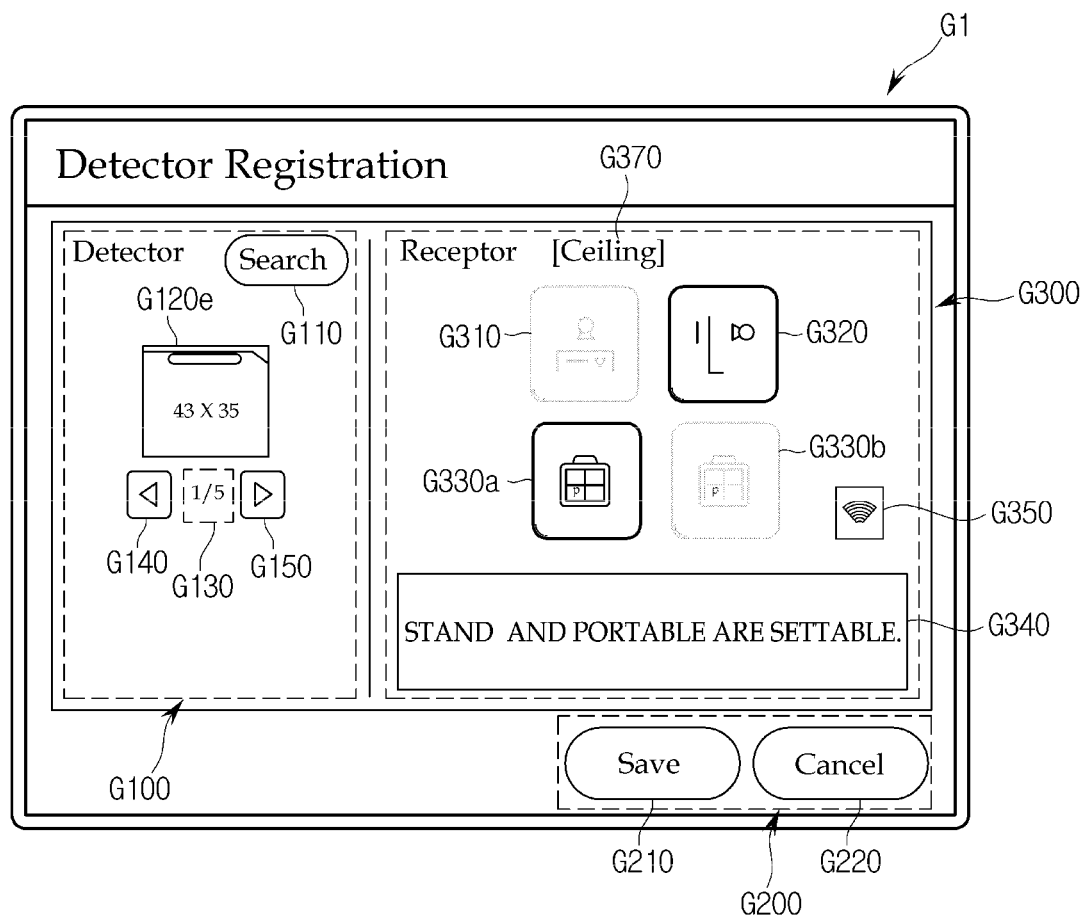
FIG. 64 is a view of the graphic user interface for selecting a ceiling type modality after detector-searching according to an exemplary embodiment.

Also, when the user determines a modality in which the selected first x-ray detector is usable to be the ceiling type, selects the ceiling selection button G710, and pushes the saving button G210, the graphic user interface G1 may be switched from FIG. 63 into FIG. 64.

When the graphic user interface G1 is switched into FIG. 64, the user may select the mounting portion 300 of a ceiling type modality. In this case, like before, a button corresponding to the mounting portion 300 mountable for 43×35 cm that is the size of the selected first x-ray detector may be activated. That is, the graphic user interface G1 may activate the stand selection button G320 and the first portable selection button G330a and may display a text "Stand and Portable are settable." on the available mounting portion text screen G340.

Also, a selected modality text screen G370 may be displayed on top of the mounting portion screen G300 to allow the user to recognize that a presently selected modality is the ceiling type modality. That is, on the selected modality text screen G370, a text "[Ceiling]" may be displayed.

Hereinafter, referring to FIG. 65, an exemplary embodiment for a graphic user interface which displays both a usable modality and mounting portion on one screen will be described.

Figure 65:
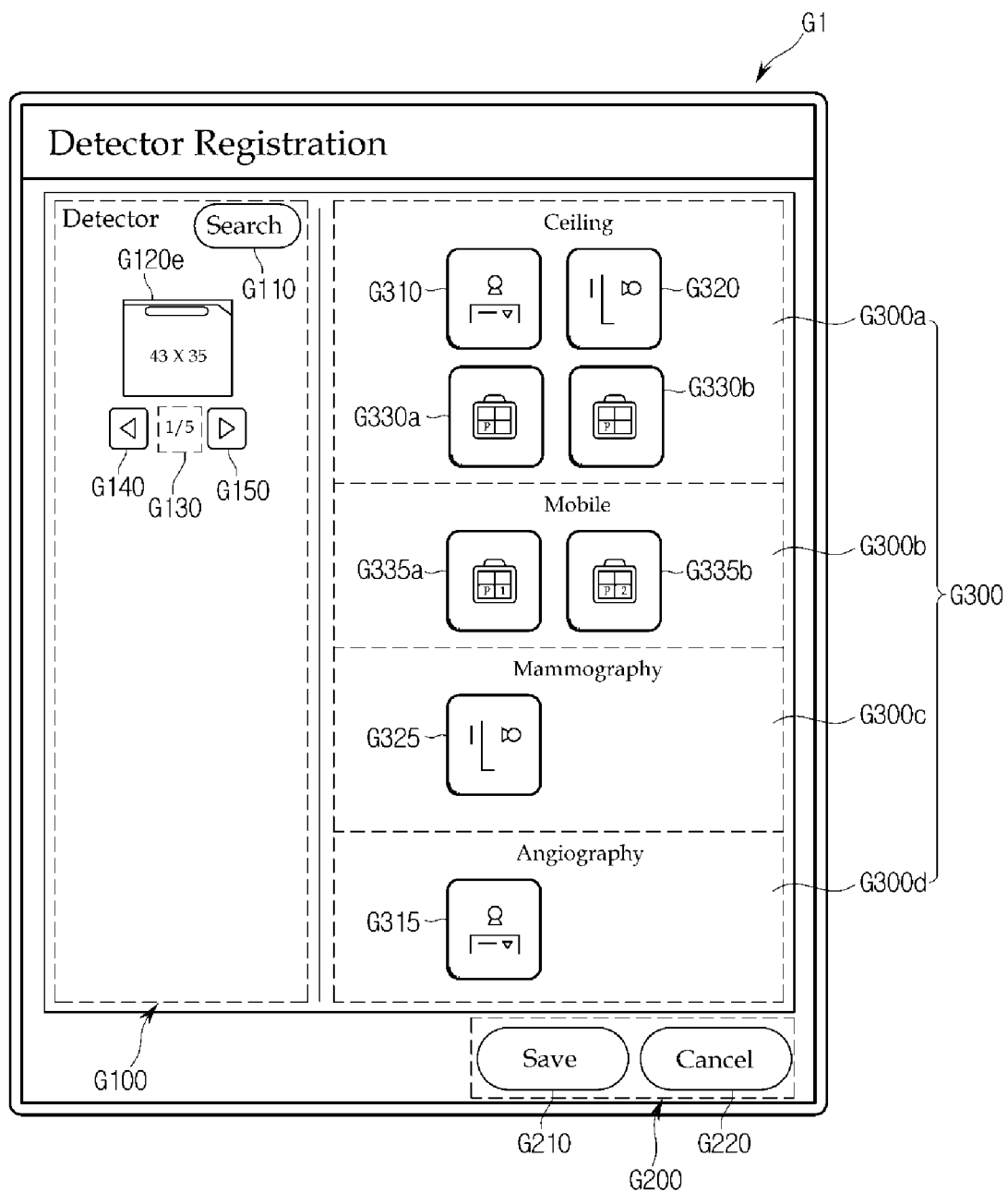
FIG. 65 is a view of a graphic user interface which displays connectable mounting portions for all respective modalities after detector-searching according to an exemplary embodiment.

FIG. 65 is a view of a graphic user interface which displays connectable mounting portions for all respective modalities after detector-searching according to an exemplary embodiment.

The user may use the graphic user interface G1 which displays all modalities usable for the selected x-ray detector 100 and the mountable mounting portions 300.

In detail, the mounting portion screen G300 may include a ceiling type screen G300a, a mobile type screen G300b, a mammography type screen G300c, and an angiography type screen G300d.

The ceiling type screen G300a is a user interface for displaying and setting the mounting portion 300 capable of mounting the selected x-ray detector 100 on the ceiling type x-ray imaging apparatus. The ceiling type screen G300a may display a text "Ceiling" which indicates a ceiling type modality on top, may display the table selection button G310, the stand selection button G320, the first portable selection button G330a, and the second portable selection button G330b, may activate a button corresponding to the mountable mounting portion 300, and may deactivate a button corresponding to the mounting portion 300 incapable of mounting.

The mobile type screen G300b is a user interface for displaying and setting the mounting portion 300 capable of mounting the selected x-ray detector 100 on the mobile type x-ray imaging apparatus. The mobile type screen G300b may display a text "Mobile" which indicates a mobile type modality on top, may display the first portable selection button G335a and the second portable selection button G335b, may activate a button corresponding to the mountable mounting portion 300, and may deactivate a button corresponding to the mounting portion 300 incapable of mounting.

The mammography type screen G300c is a user interface for displaying and setting the mounting portion 300 capable of mounting the selected x-ray detector 100 on the mammography type x-ray imaging apparatus. The mammography type screen G300c may display a text "Mammography" which indicates a mammography type modality on top, may display the stand selection button G325, may activate a button corresponding to the mountable mounting portion 300, and may deactivate a button corresponding to the mounting portion 300 incapable of mounting.

The angiography type screen G300d is a user interface for displaying and setting the mounting portion 300 which can mount the selected x-ray detector 100 on the angiography type x-ray imaging apparatus. The angiography type screen G300d may display a text "Angiography" which indicates an angiography type modality on top, may display the table selection button G315, may activate a button corresponding to the mountable mounting portion 300, and may deactivate a button corresponding to the mounting portion 300 incapable of mounting.

The graphic user interfaces described above are examples described with reference to FIGS. 17 to 65. Icons, screen arrangement, sizes and ratios of screens, contents of texts, and shapes of images are not limited to FIGS. 17 to 65. The graphic user interface may provide functions described above.

Figure 66:
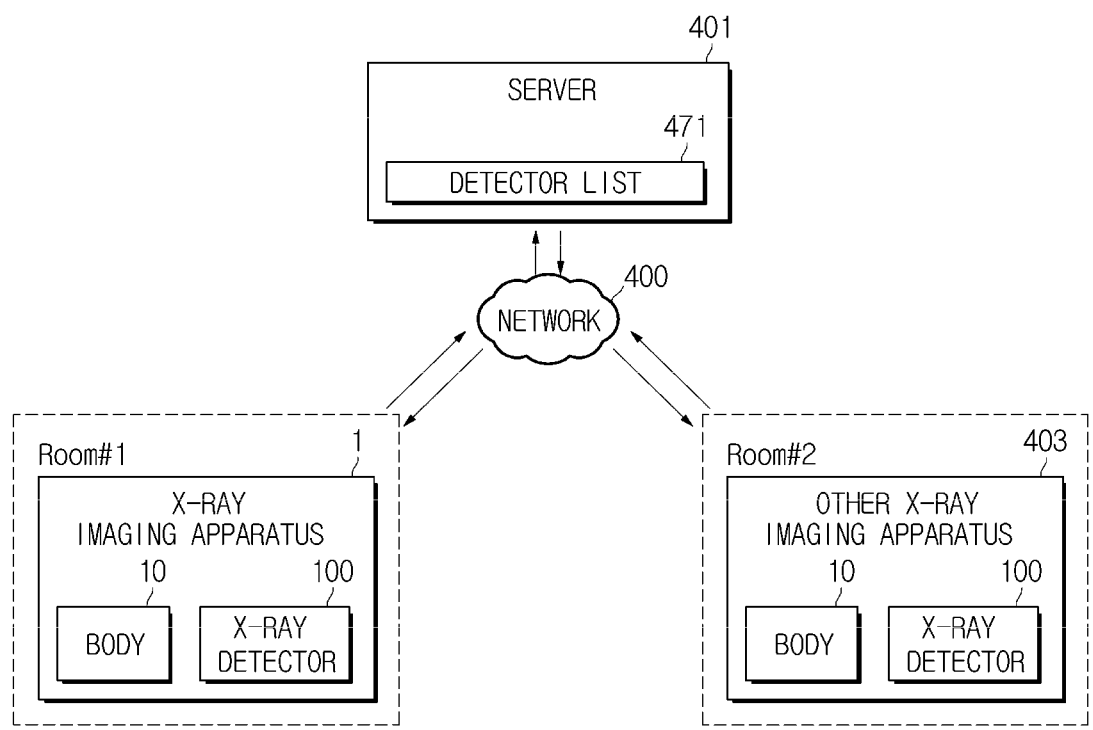
FIG. 66 is a conceptual view illustrating that communication is performed between a plurality of diagnosis rooms and a server according to an exemplary embodiment.

FIG. 66 is a conceptual view illustrating that communication is performed between a plurality of diagnosis rooms and a server according to an exemplary embodiment.

In an x-ray imaging system, communication may be performed between the x-ray imaging apparatus 1 and the server 401 or image information, state information, and setting information may be transmitted and received between the x-ray imaging apparatuses 1 located in different diagnosis rooms. Also, the x-ray imaging system may include the server 401, the x-ray imaging apparatus 1, the other x-ray imaging apparatus 403, and the network 400.

The server 401 is a computer in which information used in common is stored or programs which use a lot of computer resources such as a memory are collected in one computer on a communication network which connects several computers through communication lines. The server 401 may store detector sharing data 471.

The detector sharing data 471 may be identical to or differ from the detector pairing data 271 described above with reference to FIG. 3.

Here, the detector sharing data 471 is information on an x-ray detector usable in an x-ray imaging apparatus connected to a network and may include detector identification data, data for detector-setting, feature information on the x-ray detector, etc. Also, the detector sharing data 471 may be data obtained by receiving and combining x-ray pairing data stored in x-ray imaging apparatuses located in respective diagnosis rooms. Also, the detector sharing data 471 may include information on diagnosis rooms in which respective x-ray detectors are presently located.

The x-ray imaging apparatus 1 may include the body 10 and the x-ray detector 100 and may be located in the first diagnosis room ROOM #1. Also, the other x-ray imaging apparatus 403 may include the body 10 and the x-ray detector 100 and may be located in the second diagnosis room ROOM #2.

The network may function as a bridge which connects the server 401, the x-ray imaging apparatus 1, and the other x-ray imaging apparatus 403 described above and may transmit and receive the image information, state information, and setting information.

The x-ray imaging apparatus 1, the other x-ray imaging apparatus 403, and the server 401 may be identical to or differ from the x-ray imaging apparatus 1, the other x-ray imaging apparatus 403, and the server 401 described above with reference to FIG. 2.

The x-ray imaging apparatus 1 may download and use the detector sharing data 471 stored in the server 401 to identify and set the x-ray detector 100.

In detail, a communication interface included in a workstation may receive the detector sharing data 471 from the server 401 and may receive detector identification data from the x-ray detector 100. A controller may recognize the x-ray detector 100 connectable with the body 10 based on information in the received detector sharing data 471, corresponding to the detector identification data.

Here, operations after that the communication interface receives the detector sharing data 471 from the server 401 and transmits the detector sharing data 471 to the controller may be identical to or differ from operations of using the detector pairing data 271 stored in a storage described above.

Also, the x-ray imaging system may allow the state information and setting information to be transferred between the x-ray imaging apparatus 1 of the first diagnosis room ROOM #1 and the other x-ray imaging apparatus 403 of the second diagnosis room ROOM #2.

In detail, the x-ray imaging apparatus 1 located in the first diagnosis room ROOM #1 may transmit a state information request signal to the other x-ray imaging apparatus 403 located in the second diagnosis room ROOM #2 and may receive a state information signal from the other x-ray imaging apparatus 403. Here, the state information request signal may be a signal for requesting that the other x-ray imaging apparatus 403 transmits a using state and a reservation state of the x-ray detector 100 included in the other x-ray imaging apparatus 403, a location of a mounting portion on which the x-ray detector 100 is mounted, a size, shape, color, resolution, and response time of the detector, etc. to the x-ray imaging apparatus 1. Also, the state information signal may be information on the using state and reservation state of the x-ray detector 100 included in the other x-ray imaging apparatus 403, the location of the mounting portion on which the x-ray detector 100 is mounted, and the size, shape, color, resolution, and response time of the detector. Also, the state information signal may include information on diagnosis rooms in which the x-ray detector 100 included in the other x-ray imaging apparatus 403 is previously located and presently located.

Also, the x-ray imaging apparatus 1 located in the first diagnosis room ROOM #1 may transmit a setting information request signal to the other x-ray imaging apparatus 403 located in the second diagnosis room ROOM #2 and may receive an acknowledgement signal from the other x-ray imaging apparatus 403. Here, the setting information signal may be information for allowing the x-ray imaging apparatus 1 to select the x-ray detector 100 located in the second diagnosis room ROOM #2 and to set a modality and a mounting portion for the selected detector. Also, the setting information signal may include a signal for reserving the selected x-ray detector 100 located in the second diagnosis room ROOM #2. Also, the setting information signal may include a swap signal for swapping the x-ray detector 100 located in the second diagnosis room ROOM #2 to the first diagnosis room ROOM #1. Also, the acknowledgement signal (acknowledgement code, ACK) may be a signal transmitted by the other x-ray imaging apparatus 403 that is a receiving side to the x-ray imaging apparatus 1 that is a transmitting side, which indicates proper transmission of the setting information signal.

In the above, the configuration of the x-ray imaging apparatus and the graphic user interface have been described. The graphic user interface described above may be displayed on the display 212 provided in the workstation 200, may be displayed on the sub display 81 provided in the sub user interface 80, and may be displayed on a display provided in the mobile device 404.

Also, in the exemplary embodiments described above, an x-ray detector which has detector identification data stored in the storage 270 may be sold while being included in the x-ray imaging apparatus 1 as a component thereof or may be separately sold from the x-ray imaging apparatus 1 and then registered in the x-ray imaging apparatus 1.

When the x-ray detector separately sold from the x-ray imaging apparatus 1 is referred to as an external x-ray detector, the user interface 210 or the sub user interface 80 of the x-ray imaging apparatus 1 may provide a user interface for registering the external x-ray detector and may receive an input thereof.

For example, when the external x-ray detector is registered in the x-ray imaging apparatus 1, identification data of the registered x-ray detector may be stored in the storage 270, thereby updating the detector pairing data 271.

Hereinafter, referring to FIGS. 67 to 69, a detector setting method will be described.

Figure 67:
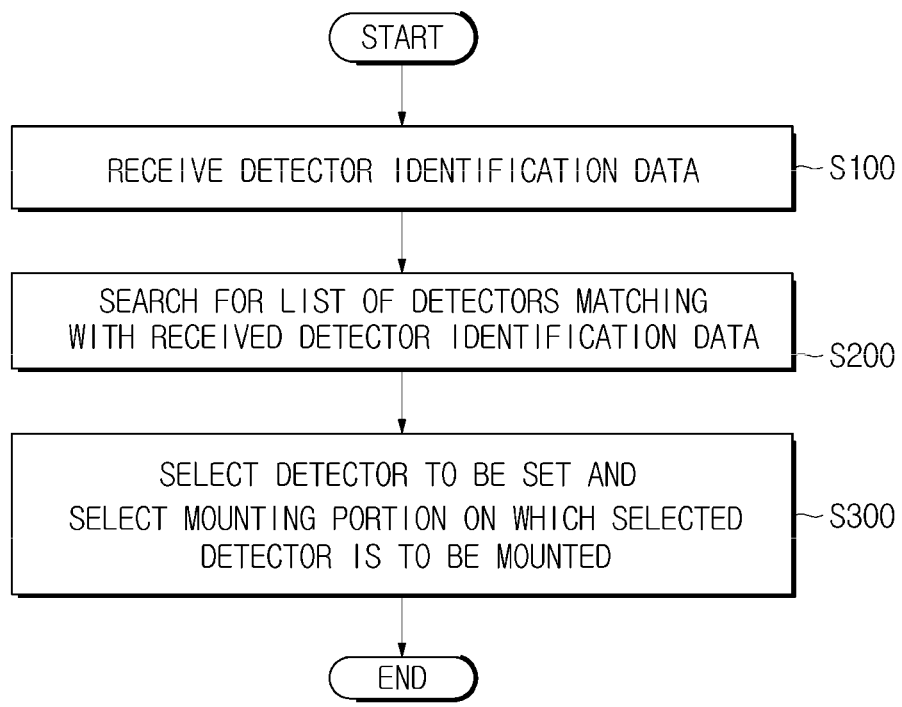
FIG. 67 is a flowchart illustrating a detector setting method according to an exemplary embodiment.

FIG. 67 is a flowchart illustrating a method of setting a detector according to an exemplary embodiment.

In operation S100, a workstation receives detector identification data previously stored in an x-ray detector.

In operation S200, the workstation searches for a list of detectors or previously stored detector pairing data matching with the detector identification data received from the x-ray detector. The searching for information in the previously stored detector pairing data matching with the detector identification data received from the x-ray detector will be described in detail with reference to following FIG. 68.

In operation S300, the workstation selects an x-ray detector to be set and selects a mounting portion on which the selected x-ray detector is to be mounted. The setting of an environment of the selected x-ray detector will be described below in detail with reference to FIG. 68.

Figure 68:
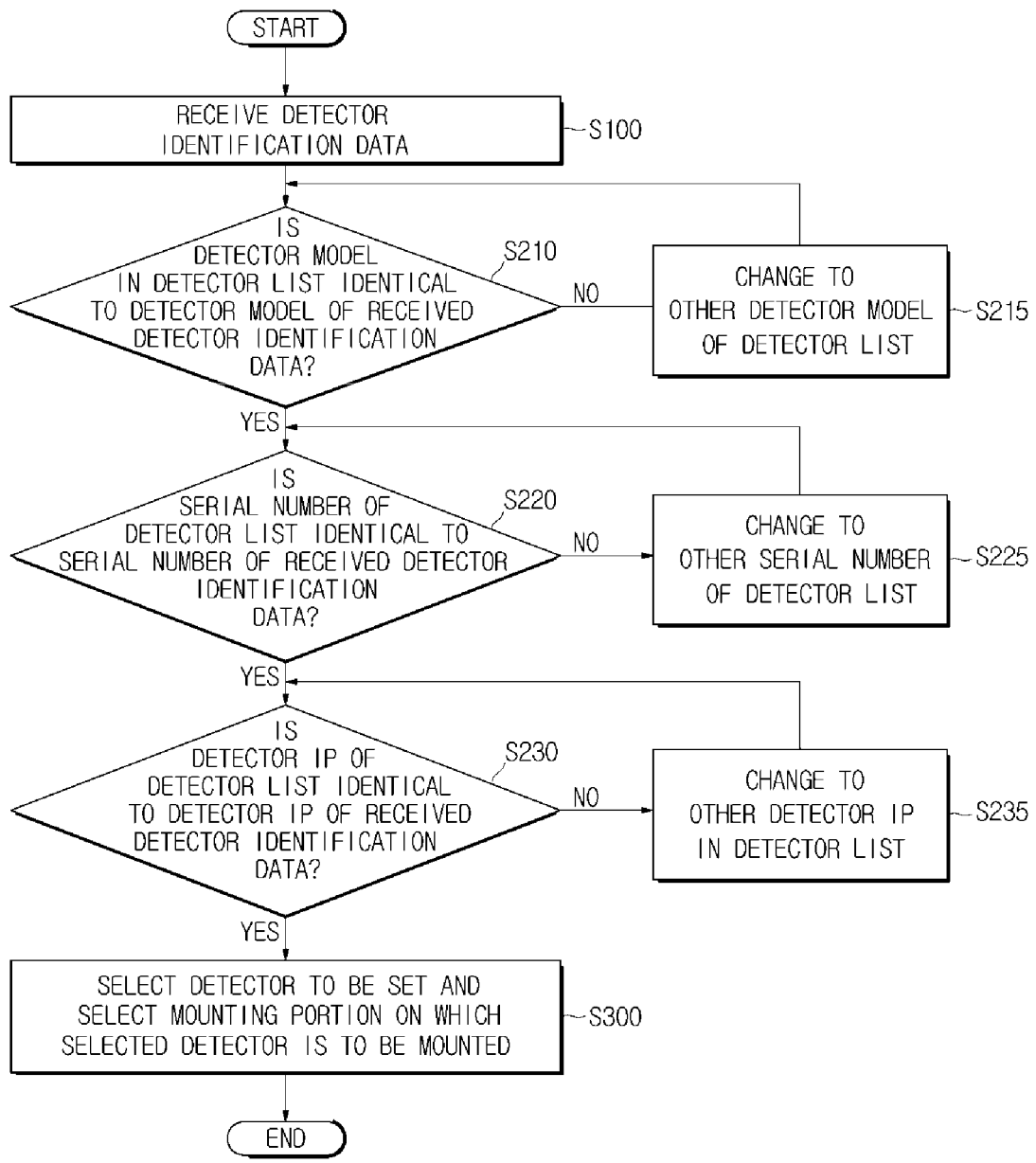
FIG. 68 is a flowchart illustrating a detector setting method according to an exemplary embodiment.

FIG. 68 is a flowchart illustrating a detector setting method according to an exemplary embodiment.

In operation S100, a workstation receives detector identification data previously stored in an x-ray detector.

In operation S210, the workstation determines whether a detector model in a detector list or detector pairing data is identical to a detector model of the received detector identification data. In response to the workstation determining that the detector model in the detector list is identical to the detector model in the received detector identification data, the workstation continues in operation S220. Otherwise, the workstation continues in operation S215.

In operation S215, the workstation changes to another detector model of the detector list or in the detector pairing data and returns to operation S210 to determine again whether the detector model in the detector pairing data is identical to the detector model in the received detector identification data.

In operation S220, the workstation determines whether a detector serial number of the detector list or in the detector pairing data is identical to a detector serial number of the received detector identification data. In response to the workstation determining that the detector serial number of the detector list is identical to the detector serial number of the received detector identification data, the workstation continues in operation S230. Otherwise, the workstation continues in operation S225.

In operation S225, the workstation changes to another detector serial number of the detector list or in the detector pairing data and returns to operation S220 to determine again whether the detector serial number in the detector pairing data is identical to the detector serial number of the received detector identification data.

In operation S230, the workstation determines whether a detector IP of the detector list or in the detector pairing data is identical to a detector IP of the received detector identification data. In response to the workstation determining that the detector IP of the detector list is identical to the detector IP of the received detector identification data, the workstation continues in operation S300. Otherwise, the workstation continues in operation S235.

In operation S235, the workstation changes to another detector IP in the detector list or the detector pairing data and returns to operation S230 to determine again whether the detector IP in the detector pairing data is identical to the detector IP of the received detector identification data.

In operation S300, the workstation selects the x-ray detector to be set and selects a mounting portion on which the selected x-ray detector is to be mounted.

Figure 69:
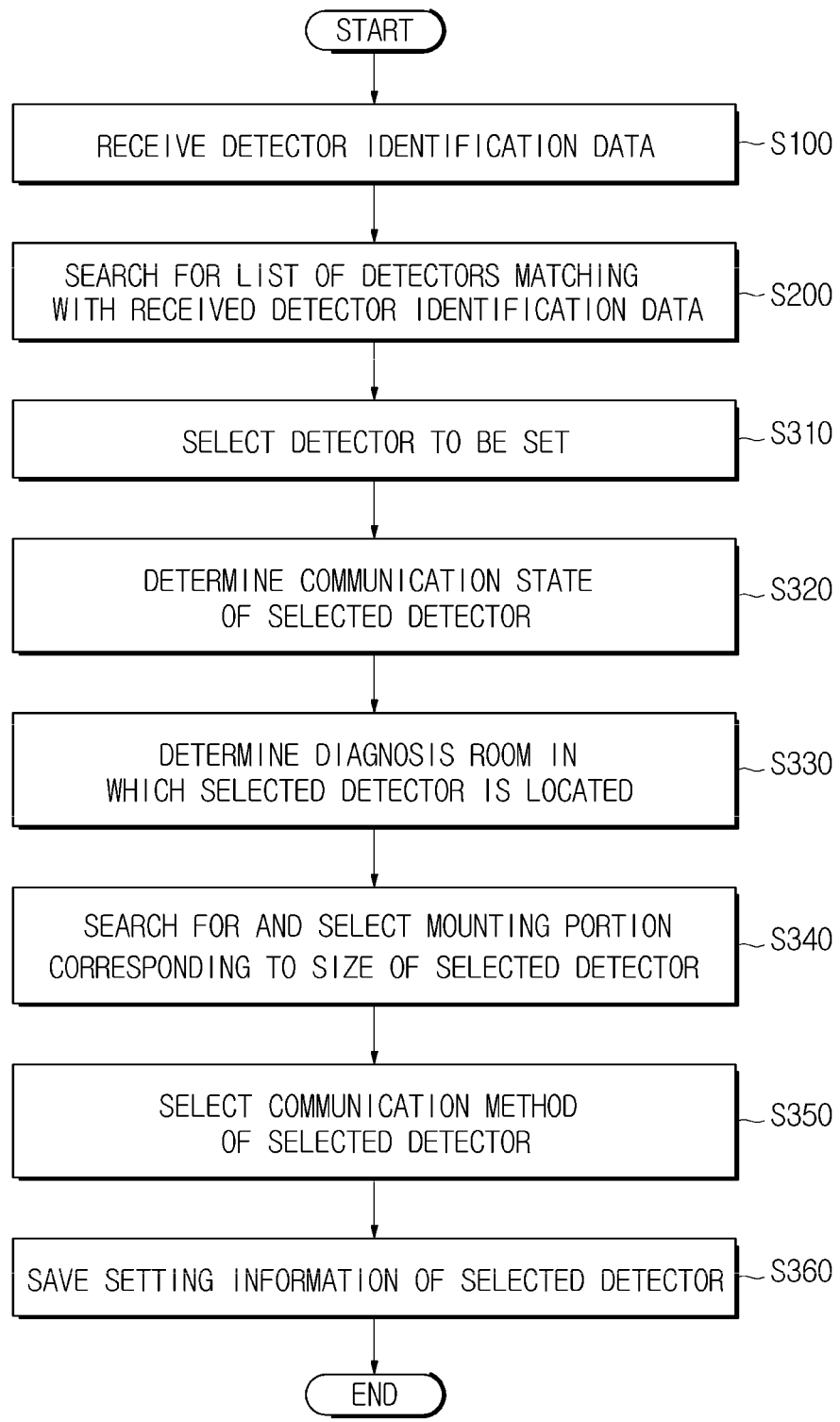
FIG. 69 is a flowchart illustrating a detector setting method according to an exemplary embodiment.

FIG. 69 is a flowchart illustrating a detector setting method according to an exemplary embodiment.

In operation S100, a workstation receives detector identification data previously stored in an x-ray detector.

In operation S200, the workstation searches for a list of detectors or previously stored detector pairing data matching with the detector identification data received from the x-ray detector.

In operations S310 to S360, the workstation selects an x-ray detector and sets the selected x-ray detector. In detail, in operation S310, the workstation allows a user to select a detector to be set through a graphic user interface, and in operation S320, the workstation determines a communication state of the selected detector. In operation S330, the workstation determines a diagnosis room in which the selected detector is located through a mounting sensor or a detector sensor. In operation S340, the workstation searches for a mounting portion corresponding to a size of the selected detector, and a mounting portion on which the selected detector is mountable is displayed to allow the user to select a mounting portion to mount the detector. In operation S350, the workstation selects a communication method between the selected detector and the workstation. In operation S360, the workstation saves setting information of the selected x-ray detector and transfers the setting information to the x-ray detector.

In addition, the exemplary embodiments may also be implemented through computer-readable code and/or instructions on a medium, e.g., a computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

As is apparent from the above description, an x-ray imaging apparatus, a method of controlling the same, and an x-ray imaging system according to an exemplary embodiment may set a detector that is not set yet using detector pairing data previously stored in a workstation or a server, or make a change in settings of a previously set detector.

Also, according to at least one of a size, color, shape, resolution, and response time of an x-ray detector, one of a plurality of x-ray detectors may be selected.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An x-ray imaging apparatus comprising:
a display;
an input device; and
a controller configured to:
control the display to display a first icon indicating a first mounting portion and a second icon indicating a second mounting portion;
receive, via the input device, a user selection of one of the first icon and the second icon that are displayed; and
based on the user selection of the first icon being received:
control the display to distinguish the first icon that is displayed, from the second icon that is displayed, by displaying the first icon in a first color different than a second color of the second icon,
receive, via the input device, a user selection of an x-ray detector among a plurality of x-ray detectors and that is mountable in the first mounting portion, and
control the display to display an icon corresponding to the selected x-ray detector.

2. The x-ray imaging apparatus of claim 1, wherein, based on the user selection of the first icon being received, the controller is further configured to control the display to display an icon indicating a color corresponding to the selected x-ray detector.

3. The x-ray imaging apparatus of claim 1, wherein, based on the user selection of the first icon being received, the controller is further configured to control the display to display an icon indicating at least one of a shape, resolution and a response time of the selected x-ray detector.

4. The x-ray imaging apparatus of claim 1, wherein, based on the user selection of the first icon being received, the controller is further configured to control the display to display state information corresponding to the selected x-ray detector.

5. The x-ray imaging apparatus of claim 1, wherein, based on the user selection of the first icon being received, the controller is further configured to control the display to display information about a color of the selected x-ray detector.

6. The x-ray imaging apparatus of claim 1, wherein, based on the user selection of the first icon being received, the controller is further configured to control the display to display information about a shape of the selected x-ray detector.

7. The x-ray imaging apparatus of claim 1, wherein, based on the user selection of the first icon being received, the controller is further configured to control the display to display information about a resolution of the selected x-ray detector.

8. The x-ray imaging apparatus of claim 1, wherein, based on the user selection of the first icon being received, the controller is further configured to control the display to display information about a response time of the selected x-ray detector.

9. The x-ray imaging apparatus of claim 1, wherein, based on the user selection of the first icon being received, the controller is further configured to control the display to display information about a diagnosis room of the selected x-ray detector.

10. The x-ray imaging apparatus of claim 1, wherein, based on the user selection of the first icon being received, the controller is further configured to control the display to display information about a color, a shape, a resolution and a response time of the selected x-ray detector.

11. The x-ray imaging apparatus of claim 1, wherein, based on the user selection of the first icon being received, the controller is further configured to control the display to display information about a color, a shape, a resolution, a response time and a diagnosis room of the selected x-ray detector.

12. An x-ray imaging apparatus comprising:
a display;
an input device; and
a controller configured to control the display to display colors of a plurality of x-ray detectors, wherein
the input device is configured to receive a user selection of one of the colors of the plurality of x-ray detectors that are displayed, and the controller is further configured to, in response to the first user selection being received, control the display to, while the color of the user selection is displayed, display a first icon indicating a first mounting portion in which an x-ray detector having the color of the user selection, among the plurality of x-ray detectors, is mountable, wherein the first icon is selectable to select the first mounting portion to indicate that the x-ray detector having the color of the user selection is to be mounted in the first mounting portion, and display a second icon indicating a second mounting portion in which the x-ray detector having the color of the user selection is not mountable, wherein the second icon is not selectable.

13. An x-ray imaging apparatus comprising:

a display;

an input device; and a controller configured to control the display to display any one or any combination of shapes, resolutions, and response times of a plurality of x-ray detectors, wherein the input device is configured to receive a user selection of one of the shapes, the resolutions, and the response times of the plurality of x-ray detectors that are displayed, and the controller is further configured to, in response to the user selection being received, control the display to, while the one of the shapes, the resolutions, and the response times of the plurality of x-ray detectors that was selected, is displayed, display a first icon indicating a first mounting portion in which an x-ray detector, among the plurality of x-ray detectors, is mountable, the x-ray detector corresponding to the one of the shapes, the resolutions, and the response times of the plurality of x-ray detectors that was selected, and display a second icon indicating a second mounting portion in which the x-ray detector is not mountable.

14. A method of controlling an x-ray imaging apparatus, the method comprising:

displaying a GUI (Graphing User Interface) to receive a first condition from a user to search for one or more x-ray detectors among a plurality of x-ray detectors, the first condition comprising any one or any combination a size, a color, a shape, a resolution, a response time, and a first diagnosis room of the one or more x-ray detectors;

receiving, via the GUI, the first condition from the user;

in response to there being a x-ray detector, among the plurality of x-ray detectors, corresponding to the first condition that was received, displaying, via the GUI, a first icon indicating a first mounting portion in which the x-ray detector is mountable, wherein the first icon is selectable to indicate that the x-ray detector is to be mounted in the first mounting portion, and displaying, via the GUI, a second icon indicating a second mounting portion in which the x-ray detector is not mountable, wherein the second icon is not selectable.

15. The method of claim 14, further comprising, in response to there being no x-ray detector, among the plurality of x-ray detectors, corresponding to the first condition that was received:

displaying, via the GUI, information indicating a second detector, among the plurality of x-ray detectors, corresponding to a second condition similar to the first condition.

16. The method of claim 14, wherein the first condition includes a first diagnosis room, and the method further comprising, in response to there being no x-ray detector, among the plurality of x-ray detectors, corresponding to the first condition that was received:

receiving, from a server, information of a second diagnosis room in which an x-ray detector corresponding to a second condition is positioned;

displaying, via the GUI, the information of the second diagnosis room.

17. The method of claim 14, further comprising, in response to there being the x-ray detector corresponding to the first condition that was received:

displaying, via the GUI, at least one modality in which the x-ray detector is usable.

18. The method of claim 17, further comprising:

receiving, via the GUI, a user selection of at least one modality of the at least one modality that is displayed.

19. The method of claim 17, further comprising:

displaying a respective mounting portion in which the x-ray detector is mountable, for each modality of the at least one modality.

\* \* \* \* \*

UNITED STATES PATENT AND TRADEMARK OFFICE
CERTIFICATE OF CORRECTION

PATENT NO. : 10,610,178 B2
APPLICATION NO. : 16/257821
DATED : April 7, 2020
INVENTOR(S) : Jong Seo Park et al.

Page 1 of 1

It is certified that error appears in the above-identified patent and that said Letters Patent is hereby corrected as shown below:

In the Claims

Column 55, Line 2, In Claim 12, before "user" delete "first".

Column 55, Line 29, In Claim 13, after "detectors" insert -- , --.

Column 56, Line 5, In Claim 14, before "x-ray" insert -- first --.

Column 56, Line 9, In Claim 14, before "x-ray" insert -- first --.

Column 56, Line 11, In Claim 14, before "x-ray" insert -- first --.

Column 56, Line 14, In Claim 14, before "x-ray" insert -- first --.

Column 56, Line 36, In Claim 17, before "x-ray" insert -- first --.

Column 56, Line 39, In Claim 17, before "x-ray" insert -- first --.

Column 56, Line 45, In Claim 19, before "x-ray" insert -- first --.

Signed and Sealed this
Second Day of June, 2020

Andrei Iancu
*Director of the United States Patent and Trademark Office*